(12) United States Patent
Biondo et al.

(10) Patent No.: US 7,343,916 B2
(45) Date of Patent: Mar. 18, 2008

(54) PULMONARY THERAPY APPARATUS

(75) Inventors: John P. Biondo, Aurora, IN (US);
Kenneth L. Kramer, St. Paul, IN (US);
Carl W. Riley, Milan, IN (US);
Gregory W. Branson, Batesville, IN (US); Richard W. Chance, Greenwood, IN (US); Tatiana Leblanc, Columbus, OH (US); Barry P. Markwick, Columbus, OH (US); Peter A. Koloski, Columbus, OH (US); Troy D. Acton, Saint Paul, IN (US); Michael E. Cerimele, Indianapolis, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 370 days.

(21) Appl. No.: 10/919,652

(22) Filed: Aug. 17, 2004

(65) Prior Publication Data

US 2005/0011518 A1    Jan. 20, 2005

Related U.S. Application Data

(62) Division of application No. 09/906,561, filed on Jul. 16, 2001, now Pat. No. 6,817,363.

(60) Provisional application No. 60/218,923, filed on Jul. 14, 2000.

(51) Int. Cl.
*A61G 16/00* (2006.01)
(52) U.S. Cl. .................... 128/204.18; 602/13
(58) Field of Classification Search ............ 602/13, 602/12; 601/41, 43, 48–49, 55–56, 77, 148, 601/149–152; 128/DIG. 20
See application file for complete search history.

(56) References Cited

U.S. PATENT DOCUMENTS

| | | |
|---|---|---|
| 1,021,335 A | 3/1912 | Robinson |
| 1,573,571 A | 2/1926 | Pohl |
| 1,667,982 A | 5/1928 | Pearson |
| 1,799,692 A | 4/1931 | Knott |
| 2,076,675 A | 4/1937 | Sharp |
| 2,141,100 A | 12/1938 | Warden |
| 2,239,821 A | 4/1941 | Knox |
| 2,311,542 A | 2/1943 | Holme |
| 2,391,928 A | 1/1946 | Seib |
| 2,417,378 A | 3/1947 | Robinson |
| 2,499,101 A | 2/1950 | Kluglein |
| 2,503,314 A | 4/1950 | Atwood |
| 2,607,103 A | 8/1952 | Davidson |
| 2,613,371 A | 10/1952 | Keyes, Jr. |
| 2,639,206 A | 5/1953 | Butler |
| 2,667,169 A | 1/1954 | Kambourakis |

(Continued)

FOREIGN PATENT DOCUMENTS

EP    0025701    3/1981

(Continued)

*Primary Examiner*—Michael A. Brown
(74) *Attorney, Agent, or Firm*—Barnes & Thornburg LLP

(57) ABSTRACT

A pulmonary therapy system includes a chest binding apparel apparatus including a plurality of air bladders. The chest binding apparel apparatus is configured to be supported proximate the chest of a patient.

15 Claims, 60 Drawing Sheets

U.S. PATENT DOCUMENTS

| | | |
|---|---|---|
| 2,673,987 A | 4/1954 | Upshaw et al. |
| 2,675,564 A | 4/1954 | Hughes |
| 2,715,737 A | 8/1955 | Sacks |
| 2,803,022 A | 8/1957 | Wynkoop |
| 2,880,720 A | 4/1959 | Houghtaling |
| 2,902,701 A | 9/1959 | Driskill |
| 2,947,007 A | 8/1960 | Oades |
| 2,984,842 A | 5/1961 | Richards |
| 3,049,726 A | 8/1962 | Getz |
| 3,110,912 A | 11/1963 | Propst |
| 3,111,687 A | 11/1963 | Sacks |
| 3,151,343 A | 10/1964 | McCormick |
| 3,200,416 A | 8/1965 | Warrick |
| 3,206,188 A | 9/1965 | Douglass, Jr. |
| 3,226,734 A | 1/1966 | Coventon |
| 3,238,539 A | 3/1966 | Koch |
| 3,286,707 A | 11/1966 | Shafer |
| 3,302,218 A | 2/1967 | Stryker |
| 3,344,445 A | 10/1967 | Crawford |
| 3,388,700 A | 6/1968 | Mountz |
| 3,434,165 A | 3/1969 | Keane |
| 3,449,776 A | 6/1969 | Brock |
| 3,451,070 A | 6/1969 | Danielson |
| 3,499,529 A | 3/1970 | Katzfey et al. |
| 3,574,871 A | 4/1971 | Greene |
| 3,584,321 A | 6/1971 | Buchanan |
| 3,609,778 A | 10/1971 | Zeiner |
| 3,648,305 A | 3/1972 | Ersek |
| 3,653,079 A | 4/1972 | Bourgraf et al. |
| 3,658,052 A | 4/1972 | Alter |
| 3,667,075 A | 6/1972 | Ballard et al. |
| 3,689,945 A | 9/1972 | Laerdal |
| 3,700,229 A | 10/1972 | Kurokawa et al. |
| 3,707,734 A | 1/1973 | Matthews |
| 3,737,924 A | 6/1973 | Davis |
| 3,739,406 A | 6/1973 | Koetter |
| 3,748,666 A | 7/1973 | Seng |
| 3,752,153 A | 8/1973 | Copeland |
| 3,765,406 A | 10/1973 | Toole et al. |
| 3,783,863 A | 1/1974 | Kliever |
| 3,814,414 A | 6/1974 | Chapa |
| 3,820,176 A | 6/1974 | Feiertag |
| 3,827,089 A | 8/1974 | Grow |
| 3,828,377 A | 8/1974 | Eary, Sr. |
| 3,832,742 A | 9/1974 | Stryker |
| 3,851,644 A | 12/1974 | Slagle |
| 3,868,103 A | 2/1975 | Pageot et al. |
| 3,874,010 A | 4/1975 | Geary |
| 3,884,225 A | 5/1975 | Witter |
| 3,890,659 A | 6/1975 | Staubs |
| 3,902,204 A | 9/1975 | Lee |
| 3,905,591 A | 9/1975 | Schorr et al. |
| 3,926,181 A | 12/1975 | Eischen |
| 3,940,808 A | 3/1976 | Petrini |
| 3,941,365 A | 3/1976 | Frymoyer |
| 4,024,861 A | 5/1977 | Vincent |
| 4,030,719 A | 6/1977 | Gabriele et al. |
| 4,033,000 A | 7/1977 | Bonifay |
| 4,054,960 A | 10/1977 | Pettit et al. |
| 4,071,916 A | 2/1978 | Nelson |
| 4,080,673 A | 3/1978 | Weisler |
| 4,084,274 A | 4/1978 | Willis et al. |
| 4,109,329 A | 8/1978 | Tupper |
| 4,152,795 A | 5/1979 | Rodosta et al. |
| 4,156,815 A | 5/1979 | Hogan |
| 4,175,550 A | 11/1979 | Leininger et al. |
| 4,183,110 A | 1/1980 | Kidd et al. |
| 4,194,732 A | 3/1980 | Liebman |
| 4,195,829 A | 4/1980 | Reser |
| 4,244,358 A | 1/1981 | Pyers |
| 4,252,594 A | 2/1981 | Cooper |
| 4,259,950 A | 4/1981 | Klippel |
| 4,274,167 A | 6/1981 | Immel |
| 4,277,857 A | 7/1981 | Svehaug |
| 4,301,791 A | 11/1981 | Franco, III |
| 4,347,635 A | 9/1982 | Eisenhauer |
| 4,356,577 A | 11/1982 | Taylor et al. |
| 4,369,982 A | 1/1983 | Hein et al. |
| 4,384,378 A | 5/1983 | Getz et al. |
| 4,395,786 A | 8/1983 | Casey et al. |
| 4,432,353 A | 2/1984 | Vrzalik |
| 4,473,912 A | 10/1984 | Scheidel et al. |
| 4,480,345 A | 11/1984 | Dunn |
| 4,490,867 A | 1/1985 | Gabrielsson |
| 4,506,664 A | 3/1985 | Brault |
| 4,535,762 A | 8/1985 | Natchev |
| 4,557,471 A | 12/1985 | Pazzini |
| 4,558,857 A | 12/1985 | Heller |
| 4,566,445 A | 1/1986 | Jelsma et al. |
| 4,572,493 A | 2/1986 | Hubert |
| 4,578,833 A | 4/1986 | Vrzalik |
| 4,579,111 A | 4/1986 | Ledesma |
| 4,584,729 A | 4/1986 | Roberts et al. |
| 4,584,989 A | 4/1986 | Stith |
| 4,586,492 A | 5/1986 | Manahan |
| 4,596,384 A | 6/1986 | Blosser |
| 4,601,075 A | 7/1986 | Smith |
| 4,612,678 A | 9/1986 | Fitsch |
| 4,619,270 A | 10/1986 | Margolis et al. |
| 4,638,516 A | 1/1987 | Vrzalik |
| 4,655,206 A | 4/1987 | Moody |
| 4,658,450 A | 4/1987 | Thompson |
| 4,676,232 A * | 6/1987 | Olsson et al. ................. 601/41 |
| 4,685,159 A | 8/1987 | Oetiker |
| 4,763,643 A | 8/1988 | Vrzalik |
| 4,769,584 A | 9/1988 | Irigoyen et al. |
| 4,779,858 A | 10/1988 | Saussereau |
| 4,827,541 A | 5/1989 | Vollman et al. |
| 4,838,263 A | 6/1989 | Warwick et al. |
| 4,840,362 A | 6/1989 | Bremer et al. |
| 4,841,585 A | 6/1989 | Masuzawa |
| 4,847,929 A | 7/1989 | Pupovic |
| 4,852,193 A | 8/1989 | Alsip et al. |
| 4,856,128 A | 8/1989 | Alsip et al. |
| 4,866,796 A | 9/1989 | Robinson et al. |
| 4,868,937 A | 9/1989 | Connolly |
| 4,872,657 A | 10/1989 | Lussi |
| 4,873,710 A | 10/1989 | Lotman |
| 4,873,731 A | 10/1989 | Williamson |
| 4,895,173 A | 1/1990 | Brault et al. |
| 4,912,754 A | 3/1990 | Van Steenburg |
| 4,920,589 A | 5/1990 | LaVelle et al. |
| 4,924,537 A | 5/1990 | Alsip et al. |
| 4,939,801 A | 7/1990 | Schaal et al. |
| 4,941,221 A | 7/1990 | Kanzler |
| 4,944,054 A | 7/1990 | Bossert |
| 4,947,418 A | 8/1990 | Barr et al. |
| 4,947,496 A | 8/1990 | Connolly |
| 4,958,817 A | 9/1990 | Heller et al. |
| 4,960,271 A | 10/1990 | Sebring |
| 4,970,739 A | 11/1990 | Bradford |
| 4,977,889 A | 12/1990 | Budd |
| 4,987,622 A | 1/1991 | Shockey |
| 4,988,062 A | 1/1991 | London |
| 5,005,233 A | 4/1991 | Toivio et al. |
| 5,014,374 A | 5/1991 | Williams |
| 5,016,268 A | 5/1991 | Lotman |
| 5,018,712 A | 5/1991 | Schaefer |
| 5,020,170 A | 6/1991 | Ruf |
| 5,023,968 A | 6/1991 | Diehl et al. |
| 5,048,071 A | 9/1991 | Van Steenburg |
| 5,048,134 A | 9/1991 | Dennill et al. |
| 5,056,505 A | 10/1991 | Warwick et al. |
| 5,058,176 A | 10/1991 | Shimazaki et al. |

| | | | | | | |
|---|---|---|---|---|---|---|
| 5,058,272 A | 10/1991 | Workman et al. | | 5,621,932 A | 4/1997 | Strachan |
| 5,060,324 A | 10/1991 | Marinberg et al. | | 5,621,933 A | 4/1997 | Knapp et al. |
| 5,062,171 A | 11/1991 | Vrzalik | | 5,626,150 A | 5/1997 | Johnson et al. |
| 5,073,999 A | 12/1991 | Thomas et al. | | 5,664,270 A | 9/1997 | Beall et al. |
| 5,083,574 A | 1/1992 | Schlutow | | 5,699,568 A | 12/1997 | Couldridge |
| 5,088,137 A | 2/1992 | Rose | | 5,740,571 A | 4/1998 | Tyra |
| 5,088,706 A | 2/1992 | Jackson | | 5,769,797 A | 6/1998 | Van Brunt et al. |
| 5,092,007 A | 3/1992 | Hasty | | 5,790,996 A | 8/1998 | Narfstrom |
| 5,103,511 A | 4/1992 | Sequin | | 5,860,899 A | 1/1999 | Rassman |
| 5,121,514 A | 6/1992 | Rosane | | 5,864,901 A | 2/1999 | Blumel |
| 5,121,756 A | 6/1992 | Koledin | | 5,950,628 A * | 9/1999 | Dunfee ...................... 128/874 |
| 5,127,422 A | 7/1992 | Colon | | 5,966,762 A | 10/1999 | Wu |
| 5,131,103 A | 7/1992 | Thomas et al. | | 6,012,183 A | 1/2000 | Brooke et al. |
| 5,131,105 A | 7/1992 | Harrawood et al. | | 6,030,353 A * | 2/2000 | Van Brunt .................. 601/150 |
| 5,131,106 A | 7/1992 | Jackson | | 6,036,662 A | 3/2000 | Van Brunt et al. |
| 5,148,815 A | 9/1992 | Britton | | 6,065,165 A | 5/2000 | Delk et al. |
| 5,152,024 A | 10/1992 | Chrones et al. | | 6,108,838 A | 8/2000 | Connolly et al. |
| 5,154,185 A | 10/1992 | Latimer et al. | | 6,112,349 A | 9/2000 | Connolly |
| 5,154,186 A | 10/1992 | Laurin et al. | | 6,119,292 A | 9/2000 | Haas |
| 5,179,746 A | 1/1993 | Rogers | | 6,141,806 A | 11/2000 | Bobey et al. |
| 5,181,288 A | 1/1993 | Heaton et al. | | 6,155,996 A | 12/2000 | Van Brunt et al. |
| 5,190,056 A | 3/1993 | Hull | | 6,210,345 B1 | 4/2001 | Van Brunt |
| 5,208,928 A | 5/1993 | Kuck et al. | | 6,240,584 B1 | 6/2001 | Perez et al. |
| 5,211,186 A | 5/1993 | Shoemaker et al. | | 6,260,220 B1 | 7/2001 | Lamb et al. |
| 5,230,112 A | 7/1993 | Harrawood et al. | | 6,282,736 B1 | 9/2001 | Hand et al. |
| 5,230,113 A | 7/1993 | Foster et al. | | 6,308,353 B1 | 10/2001 | Van Steenburg |
| 5,243,639 A | 9/1993 | Johnson | | 6,327,727 B1 | 12/2001 | Bocharnikov |
| 5,249,318 A | 10/1993 | Loadsman | | 6,340,025 B1 | 1/2002 | Van Brunt et al. |
| 5,255,303 A | 10/1993 | DiMaio et al. | | D453,560 S | 2/2002 | Van Brunt |
| 5,263,213 A | 11/1993 | Robertson et al. | | 6,353,949 B1 | 3/2002 | Falbo |
| 5,274,862 A | 1/1994 | Palmer, Jr. et al. | | 6,375,017 B1 | 4/2002 | Schattner et al. |
| 5,274,864 A | 1/1994 | Morgan | | 6,379,316 B1 | 4/2002 | Van Brunt et al. |
| 5,285,797 A | 2/1994 | Zeller | | 6,385,801 B1 | 5/2002 | Watanabe et al. |
| 5,299,334 A | 4/1994 | Gonzalez | | 6,415,791 B1 | 7/2002 | Van Brunt et al. |
| 5,319,817 A | 6/1994 | Hay et al. | | 6,471,663 B1 | 10/2002 | Van Brunt et al. |
| 5,334,186 A | 8/1994 | Alexander | | 6,499,160 B2 | 12/2002 | Hand et al. |
| 5,336,179 A | 8/1994 | Ryan | | 6,526,610 B1 | 3/2003 | Hand et al. |
| 5,345,630 A | 9/1994 | Healy | | 6,609,260 B2 | 8/2003 | Hand et al. |
| 5,398,356 A | 3/1995 | Pfleger | | 6,736,785 B1 | 5/2004 | Van Brunt |
| 5,404,603 A | 4/1995 | Fukai et al. | | 2004/0097842 A1 | 5/2004 | Van Brunt et al. |
| 5,412,823 A | 5/1995 | Sitta | | | | |
| 5,414,883 A | 5/1995 | Fangrow, Jr. | | FOREIGN PATENT DOCUMENTS | | |
| 5,418,990 A | 5/1995 | Risasen | | | | |
| 5,427,338 A | 6/1995 | Garrett et al. | | EP | 0 569 308 A1 | 11/1993 |
| 5,433,741 A | 7/1995 | Truglio | | FR | 2.034.679 | 12/1970 |
| 5,435,323 A | 7/1995 | Rudy | | FR | 2 247 194 | 5/1975 |
| 5,453,081 A | 9/1995 | Hansen | | FR | 2 549 366 | 1/1985 |
| 5,473,784 A | 12/1995 | Nixon et al. | | FR | 2 585 240 | 1/1987 |
| 5,481,770 A | 1/1996 | Ahlsten | | FR | 2 587 898 | 4/1987 |
| 5,494,051 A | 2/1996 | Schneider, Sr. | | FR | 2 749 503 | 12/1997 |
| 5,499,416 A | 3/1996 | Daouk | | GB | 1 306 353 | 2/1973 |
| 5,502,853 A | 4/1996 | Singleton et al. | | GB | 2 182 570 | 5/1987 |
| 5,502,854 A | 4/1996 | Daouk | | TW | 77886 | 11/1975 |
| 5,515,561 A | 5/1996 | Suggitt et al. | | WO | WO 93/05745 | 4/1993 |
| 5,515,869 A | 5/1996 | Powell et al. | | WO | WO 97/22323 | 6/1997 |
| 5,530,974 A | 7/1996 | Rains et al. | | WO | WO 98/39996 | 9/1998 |
| 5,560,059 A | 10/1996 | McQueen | | WO | WO 99/07320 | 2/1999 |
| 5,568,662 A | 10/1996 | Gougelet | | WO | WO 99/53997 | 10/1999 |
| 5,569,170 A * | 10/1996 | Hansen ...................... 601/150 | | WO | WO 00/00117 | 1/2000 |
| 5,577,281 A | 11/1996 | Mital et al. | | | | |
| 5,611,096 A | 3/1997 | Bartlett et al. | | * cited by examiner | | |

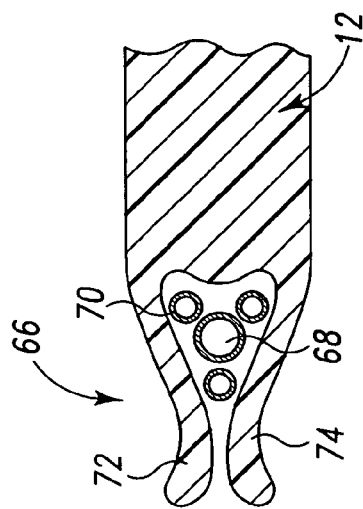
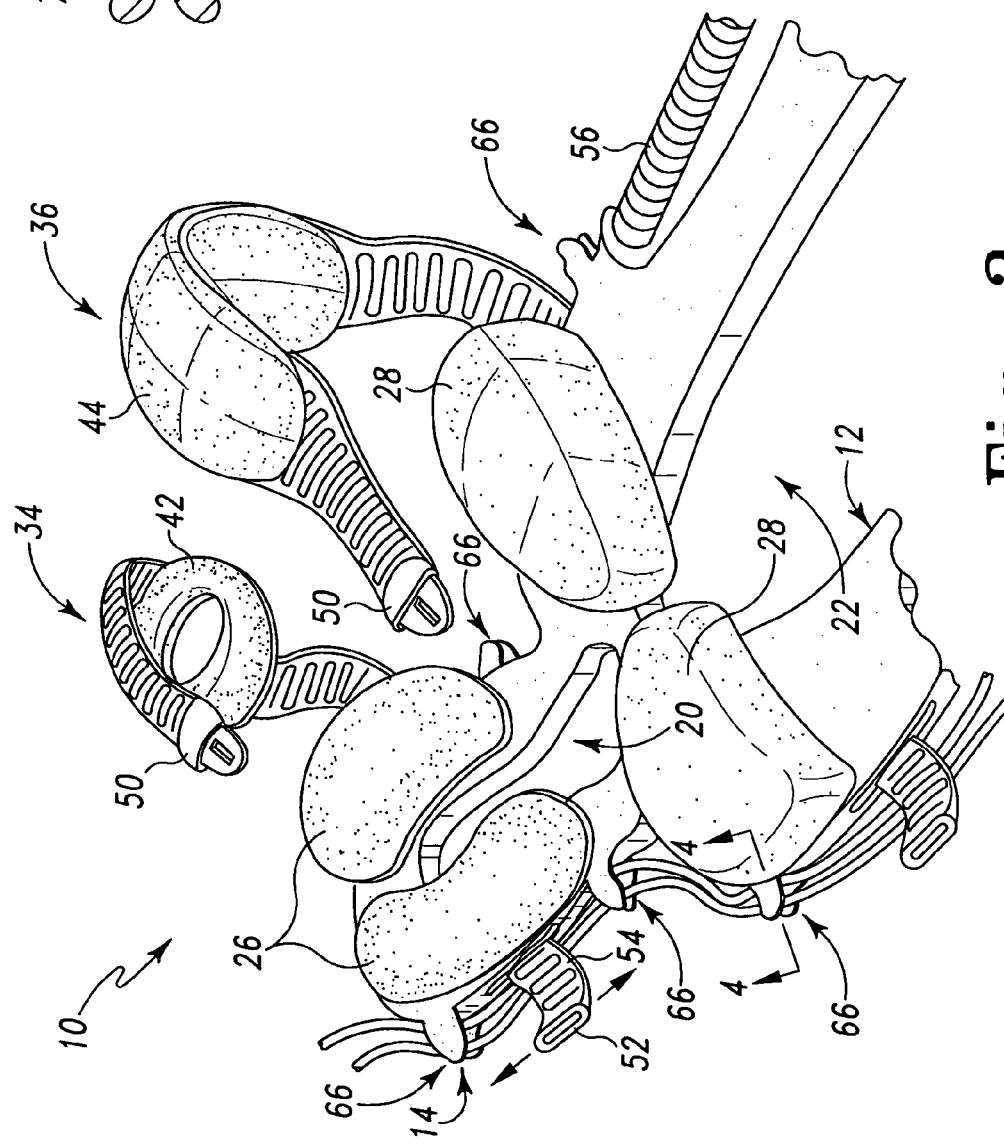
Fig. 4
Fig. 3

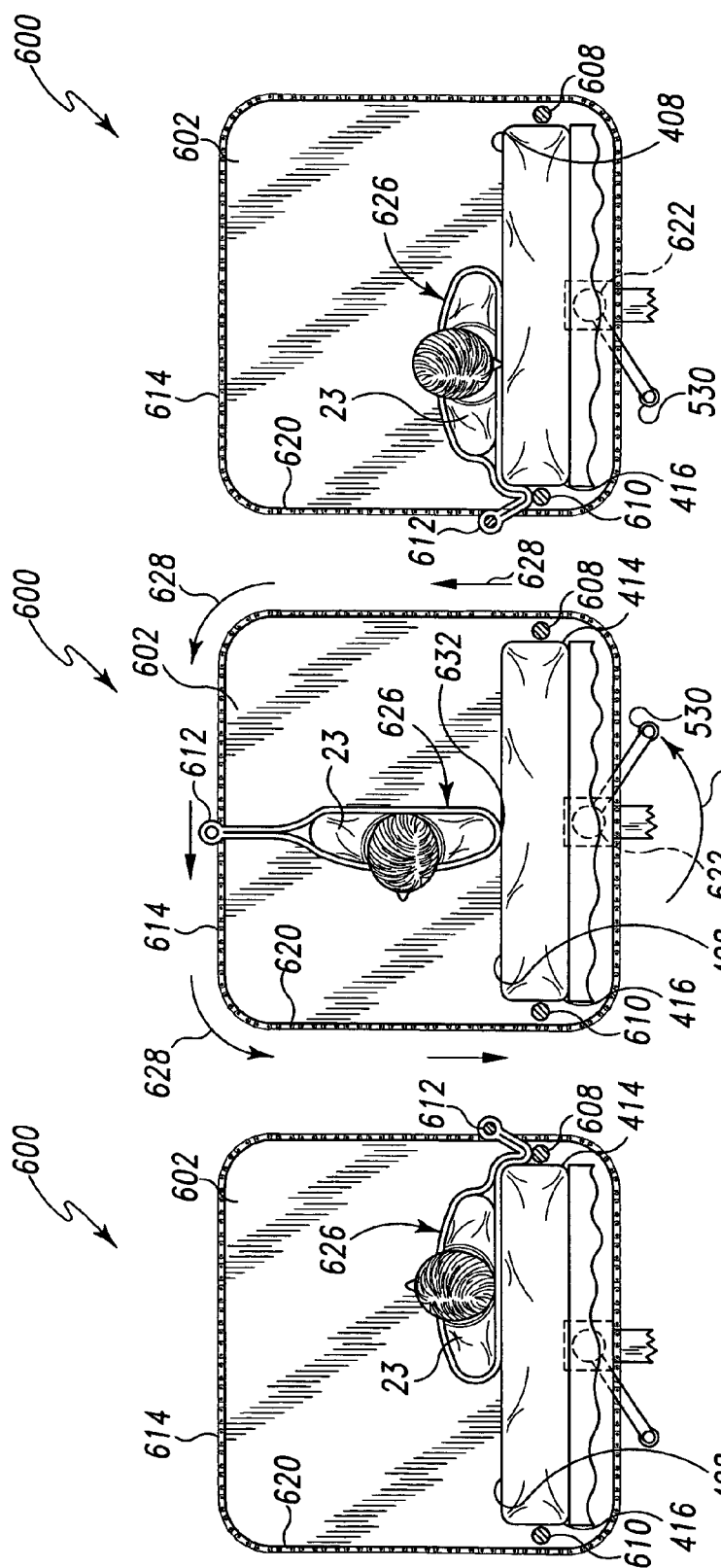

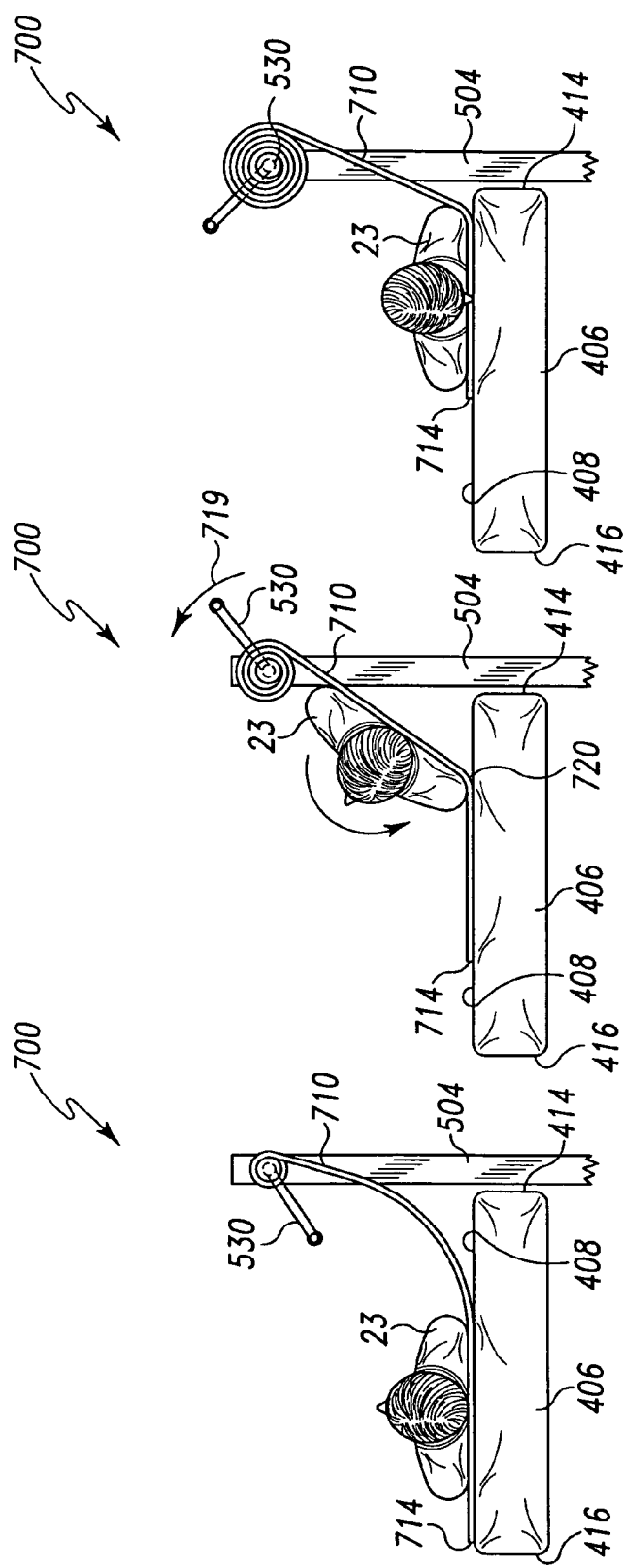

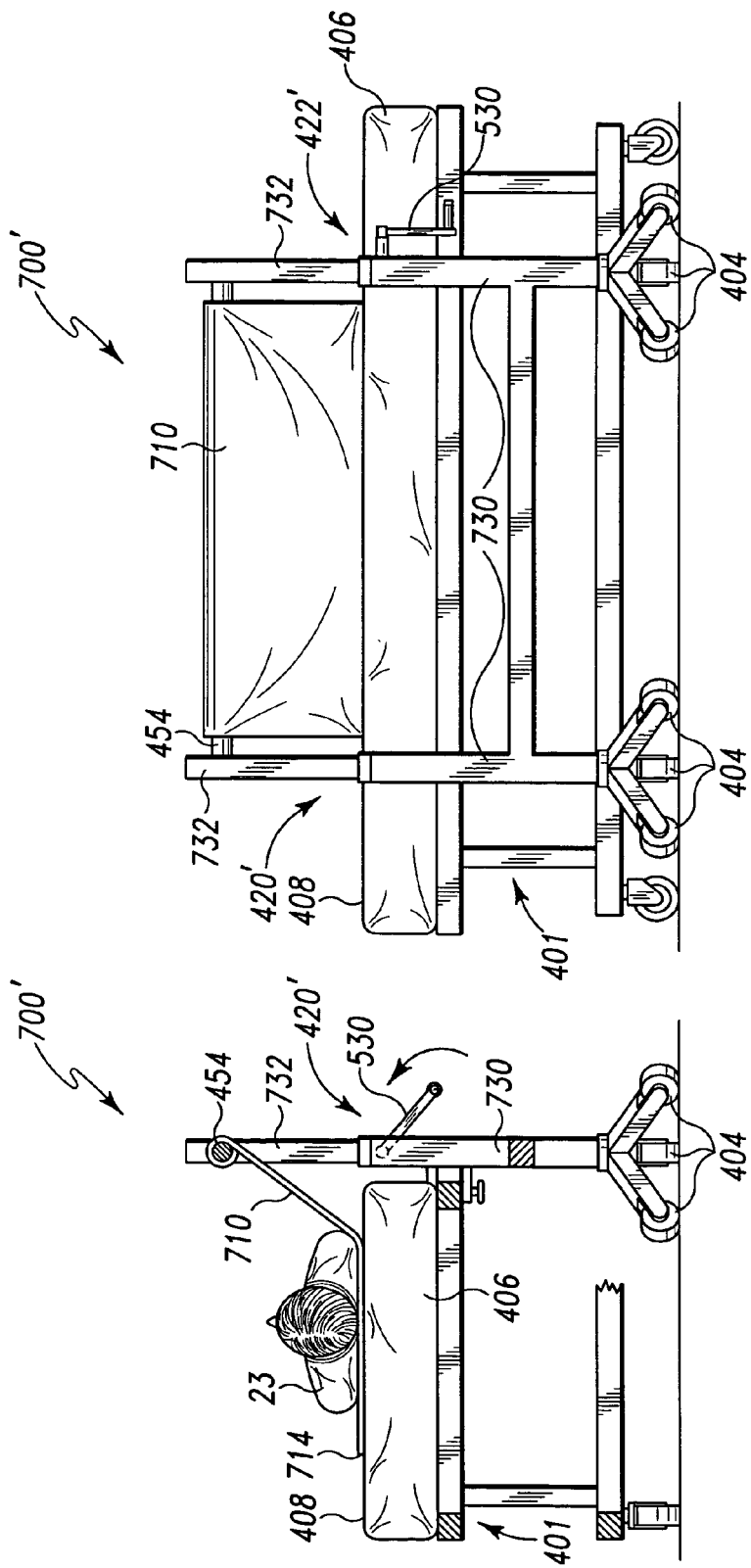

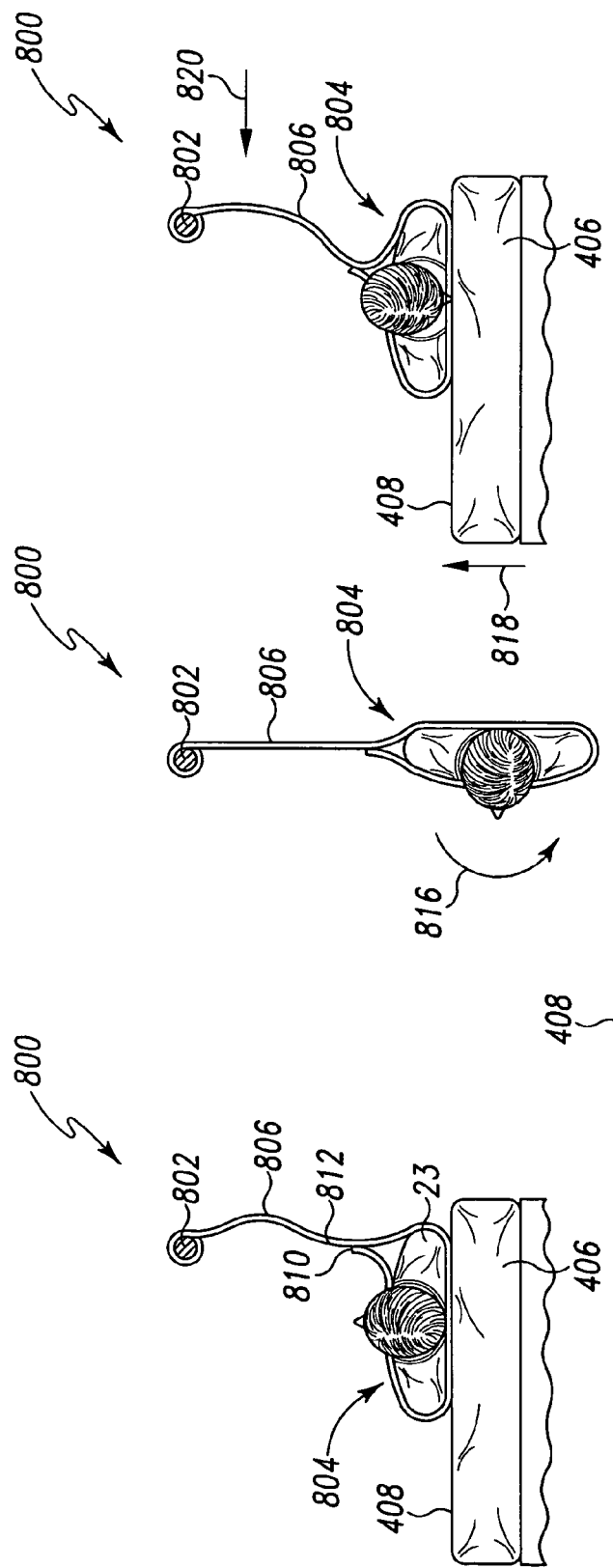

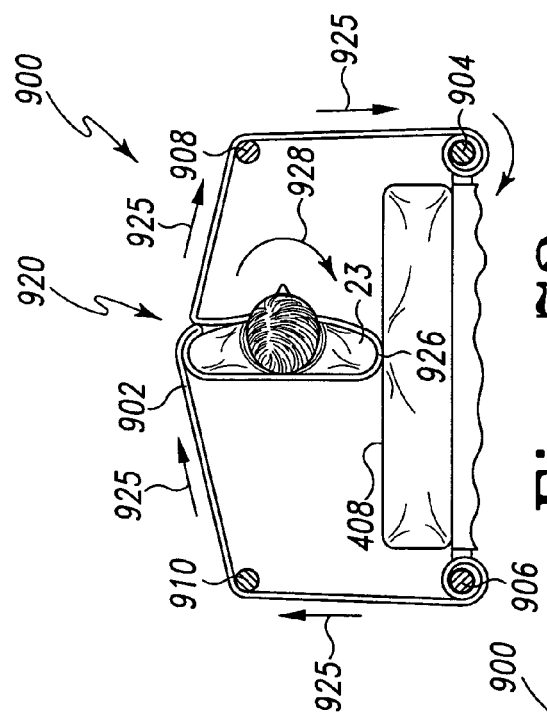
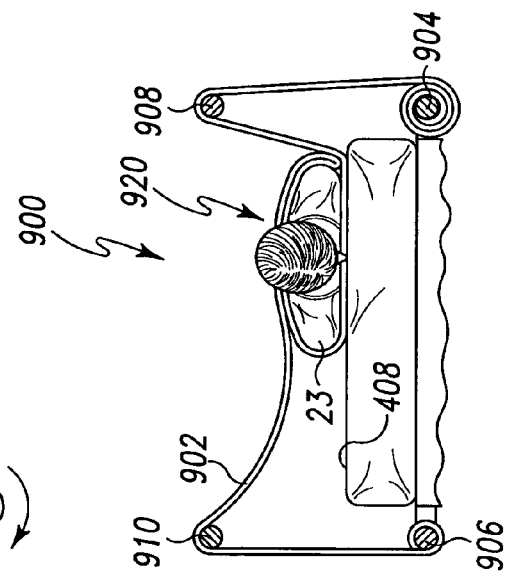
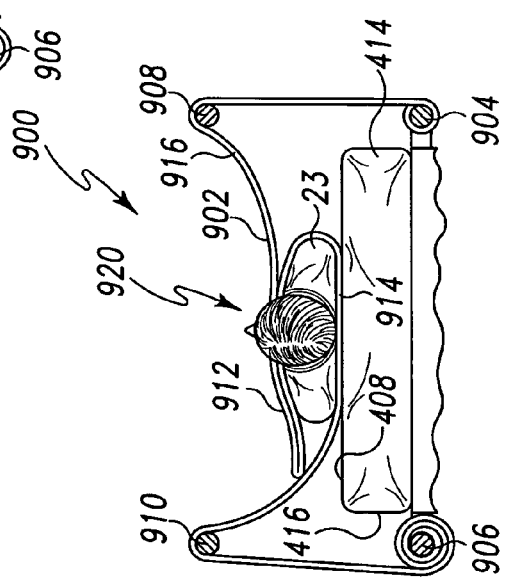
Fig. 72
Fig. 73
Fig. 71

PULMONARY THERAPY APPARATUS

CROSS REFERENCE TO RELATED APPLICATION

This application is a divisional of U.S. application Ser. No. 09/906,561, filed on Jul. 16, 2001, now U.S. Pat. No. 6,817,363 which claims the benefit of U.S. Provisional Application Ser. No. 60/218,923, filed Jul. 14, 2000, both of which are expressly incorporated herein by reference.

BACKGROUND OF THE INVENTION

The present invention relates to pulmonary therapy apparatus and, more particularly, to chest compression and proning devices which provide pulmonary therapy on a patient. Moreover, the present invention relates to a pulmonary therapy apparatus which incorporates one or more of the following components: a proning apparatus, a chest compression or binding apparatus, an oscillating motion therapy apparatus and a longitudinal rotation therapy apparatus.

The positioning of patients in a prone position (i.e., face down) typically results in improved oxygenation to the patient as opposed to a supine position (i.e., face up). More particularly, it is believed that prone positioning reduces the occurrence of acute respiratory distress syndrome (ARDS). ARDS historically has had a mortality rate often exceeding sixty percent. Additionally, bed ridden patients with diseases or infirmities not necessarily requiring improved oxygenation often require that they be rotated between supine and prone positions in order to avoid the formation of bed sores.

Traditionally, the re-positioning and, moreover, the turning of patients about their longitudinal axes, has been accomplished only with considerable effort. The turning of patients from a supine position to a prone position often requires assistance from at least three caregivers. Additionally, patients often have a plurality of tubes and lines connected to their bodies for a variety of medical reasons, including intravenous supply and ventilation. The turning process is often further complicated by intermingling or tangling of the tubes or lines.

In short, proning has proven to be an effective intervention to increase oxygenation in the ARDS patient. Ease in attaining the prone position obviously facilitates its utilization. As such, there remains a need for a prone positioning apparatus which reduces the manual labor required, increases caregiver efficiency, and improves line management.

It is also believed that chest binding or compression may prove to be an effective method of pulmonary therapy and, more particularly, alveolar recruitment. It is believed that chest binding through the application of force on the upper chest of a patient, who is supplied air through a conventional ventilator, will prevent over-extension of the upper portion of the lungs and force the ventilated air to the lower portion of the lungs. As such, a patient will receive more effective oxygenation through the ventilator. Therefore, there is a need for a chest binding device for facilitating ventilation of distant lung areas.

Another method of pulmonary therapy for improving oxygenation to a patient is through oscillating motion therapy and, moreover, through longitudinal rotation therapy. In essence, it is believed that oscillating rotational motion of a patient support surface for periodically moving a patient from a substantially upright position to a substantially horizontal position improves breathing and, therefore, oxygenation to the patient. It is further believed that placing the body in a weightless neutral body position, commonly referred to as a "zero gravity" position, optimizes such therapy. Therefore, there is a need for a longitudinal rotation apparatus which facilitates improved ventilation and lung drainage.

SUMMARY OF THE INVENTION

In an illustrated embodiment of the present invention, a proning apparatus comprises a base including a head portion, a leg portion, and a body portion positioned intermediate the head portion and the leg portion. The base further includes an opposing pair of longitudinal side edges, a patient support surface extending between the side edges, and a longitudinal axis. A face-receiving aperture is formed within the head portion and is adapted to receive a face of a patient therein. An abdomen-receiving aperture is formed within the body portion in longitudinally spaced relation to the face-receiving aperture, the abdomen-receiving aperture being adapted to expose the abdomen of a patient when the face is in the face-receiving aperture. A groin-receiving aperture is formed within the leg portion in longitudinally spaced relation to the abdomen-receiving aperture, wherein the groin-receiving aperture is adapted to expose the groin of the patient when the face is in the face-receiving aperture.

A plurality of supports are coupled to the patient surface of the base. The plurality of supports include at least one head support cushion coupled to the head portion, at least one shoulder support cushion coupled to the body portion, and at least one leg support cushion coupled to the leg portion. The plurality of supports further include at least one hip support cushion positioned intermediate the abdomen-receiving aperture and the groin-receiving aperture. A plurality of line management devices are supported by the base adjacent to the side edges, wherein the line management devices configured to releasably secure hoses and lines adjacent the base. A plurality of straps are coupled to the base adjacent one of the side edges, each of the straps including a padded section adapted for engaging the patient.

In another illustrated embodiment of the invention, a proning therapy sleeve comprises a bottom support portion including a head end and a foot end, the bottom support portion configured to be located on a mattress of a bed. A pair of opposing side portions extend outwardly from the bottom support portion. An aperture is formed in each of the pair of opposing side portions, wherein the aperture is configured to receive the arms of a patient. A head support bladder is supported in each of the side portions. At least one inflatable chest support bladder is supported in each of the side portions in spaced relation to the head support bladder. A thigh-engaging bladder is supported in each of the side portions in spaced relation to the at least one inflatable chest support bladder. A calf engaging bladder is supported in each of the side portions in spaced relation to the thigh engaging bladder.

At least one line management apparatus is supported proximate at least one of the head end and the foot end of the bottom support portion, wherein the at least one line management apparatus is configured to releasably secure hoses and lines extending to the patient. A plurality of first fasteners are supported by the first side portion and a plurality of second fasteners are supported by the second side portion wherein the first and second side portions are foldable over the front of the patient and the fasteners are connected to secure the sleeve about the patient.

The bladders are provided for support of the patient in the prone position. Additionally, the bladders may be utilized to provide therapy to the patient. More particularly, the at least one chest bladder may be inflated to provide chest binding or compression when a ventilator is used to supply air or oxygen to the patient through a ventilator tube. As air is blown into the patient's lungs through the ventilator tube, the at least one chest bladder is inflated to force air downwardly into the patient's lungs.

The bottom support surface may include a plurality of apertures forming an air zone and coupled to an air supply. When air is supplied to the air zone, the air is forced outwardly through the holes to provide an air pallet or bearing to assist in rotational movement of the patient. Additionally, the side portions may each include an outer bladder coupled to the air supply. An outer surface of the side portions include a plurality of apertures so that air flows outwardly through the outer surface for providing an air pallet or bearing. As such, the entire outer circumference of the sleeve may be provided with an air bearing to facilitate the proning of the patient.

In yet another illustrated embodiment of the present invention, a proning apparatus comprises a bottom support bladder including opposing first and second sides, an outer surface, an air chamber, and a plurality of apertures formed within the outer surface and in fluid communication with the air chamber. A plurality of side flaps include a first end coupled to the bottom support bladder proximate the first side. A plurality of fasteners are supported by the second ends of the side flaps and are releasably secured proximate the second side of the bottom support bladder. The plurality of side flaps include a first head flap coupled to the bottom support bladder proximate the first side and a second head flap coupled to the bottom support bladder proximate the second side. A head bladder is connected to each of the first and second head flaps. The side flaps further include a chest support flap supporting a plurality of chest support bladders. A bottom prone bladder is positioned to alternatively support the bottom support bladder and the plurality of side flaps. The bottom prone bladder is configured to be inflated with air when it is supporting the plurality of side flaps.

In a further illustrated embodiment of the present invention, a patient support includes a base, an inner frame supported by the base, a plurality of rollers rotatably supported by the inner frame, and a movable outer frame defining a longitudinal axis and a transverse axis. The outer frame is supported by the inner frame for longitudinal movement relative thereto. A patient support surface is supported by the outer frame, and a drive mechanism is operably connected to the movable outer frame for driving the outer frame in motion. A coupling is provided intermediate the base and the inner frame for facilitating rotation of the outer frame about the longitudinal axis and the transverse axis. A massage mechanism is supported adjacent the patient support surface. The massage mechanism includes a plurality of rollers configured to move vertically relative to the patient support surface.

In still another illustrative embodiment of the present invention, a pulmonary therapy system comprises a chest binding apparel apparatus including a plurality of air bladders and configured to be supported proximate the chest of the patient. An air supply is in fluid communication with the plurality of air bladders and is operably connected to a controller. A ventilator supplies air to the lungs of the patient and is coupled to a ventilator pressure sensor for sensing a pressure of air supplied to the patient and generating a ventilator pressure signal indicative thereof. The ventilator pressure sensor is in communication with the controller for supplying the ventilator pressure signal thereto. The controller controls air flow to the plurality of air bladders in response to the ventilator pressure signal. An apparel pressure sensor is coupled to the binding apparel apparatus for sensing a pressure applied by the binding apparel apparatus to the chest of the patient and generating an apparel pressure signal indicative thereof. The apparel pressure sensor is in communication with the controller for supplying the apparel pressure signal thereto.

A switching valve is coupled to the air supply for alternating between a first mode of operation wherein air is supplied to the air bladders and a second mode of operation wherein air is evacuated from the air bladders. An exhaust line is coupled to the switching valve for exhausting evacuated air from the air bladders to atmosphere. A bladder supply line is provided for supplying air from the air supply to the air bladders. The switching valve alternatively connects the air supply to the exhaust line and the bladder supply line.

The chest binding apparel apparatus includes a vest having a front portion, a rear portion and a head receiving aperture intermediate the front portion and the rear portion. At least one front bladder is supported by the front portion and at least one rear air bladder is supported by the rear portion. The front portion and the rear portion preferably include a substantially rigid shell wherein the at least one front air bladder and the at least one rear air bladder are supported either on an inner surface of the shell or an outer surface of the shell depending upon the desired functionality. The at least one front bladder and the at least one rear bladder each include a plurality of independently inflatable pressure zones.

In a further illustrated embodiment of the present invention, a longitudinal rotation therapy method comprises the steps of supporting a patient on a patient support surface including a head section, a back section, a seat section, and a leg section, the patient support surface further including a longitudinal axis and a transverse axis. The method further comprises the steps of positioning the head section upwardly relative to the back section, positioning the back section upwardly relative to the seat section, and positioning the leg section downwardly relative to the seat section. The method further includes the steps of rotating the patient support surface about the transverse axis in a first direction, stopping rotation of the patient support surface upon reaching a first limit, rotating the patient support surface about the transverse axis in a second direction opposite the first direction, stopping rotation of the patient support surface upon reaching a second limit, and repeating the rotating and stopping steps, thereby providing oscillating rotational movement to the patient support surface. The positioning steps comprise the steps of placing the patient in a weightless, neutral body, or zero gravity, position.

In another illustrative embodiment of the present invention, a proning apparatus includes a frame, a patient support supported by the frame and including a head end and a foot end, the patient support defining a longitudinal axis. A first upright extends substantially vertical and is positioned proximate the head end, and a second upright extends substantially vertical and is positioned proximate the foot end. A movable support member is rotatably supported intermediate the first and second uprights. A wrap is supported for movement by the movable support member, the wrap including first and second longitudinally extending side edges defining an access opening therebetween and configured to receive a patient in a set up mode of operation, and to close the access opening in a turning mode of operation. A drive mechanism is coupled to the movable support member for rotating the movable support member and the wrap.

In still another illustrative embodiment of the present invention, a proning apparatus comprises a patient support surface extending between opposing first and second side edges, the patient support surface including a head end and a foot end and defining a longitudinal axis. A first drive support member is positioned proximate the head end and a second drive support member is positioned proximate the foot end. A drive mechanism is supported by the first and second drive support members. A sleeve support member is coupled to the drive mechanism for lateral movement above the patient support surface. A sleeve is supported by the support member, the sleeve including an inner surface configured to contain a patient and an outer surface configured to engage the patient support surface. A guide member is provided for guiding movement of the support member upwardly from proximate the first side edge, transversely above the patient support surface and downwardly to proximate the second side edge.

In a further illustrative embodiment of the present invention, a proning apparatus comprises a frame, a patient support supported by the frame and extending between first and second sides, the patient support including a head end and foot end and defining a longitudinal axis. A first upright is positioned proximate the head end and a second upright is positioned proximate the foot end. A support member is coupled to the first and second uprights and is positioned above the patient support surface. A sheet is secured to the support member and a pulling device is supported by the first and second uprights for moving the support member and drawing the sheet in a direction upwardly and from proximate the first side to proximate the second side of the patient support surface.

In yet another illustrative embodiment of the present invention, a proning apparatus comprises a frame, a patient support surface supported by the frame and extending between opposing first and second side edges, the patient support surface including a head end and a foot end and defining a longitudinal axis. An adjustment mechanism is supported by the frame for driving the patient support surface in vertical movement. A first upright is positioned proximate the head end and a second upright is positioned proximate the foot end. A support member is coupled to the first and second uprights and is positioned vertically above the patient support surface and positioned horizontally offset from the longitudinal axis, proximate one of the first and second side edges. A sleeve, including a center portion disposed intermediate first and second ends, is supported by the support member. At least one fastener is provided for securing the second end of the sleeve to the center portion thereof.

In a further illustrative embodiment of the present invention, a method of turning a patient from a supine position to a prone position is provided, the method comprising the steps of providing a patient support surface extending between opposing first and second side edges, the patient support surface including a head and a foot end and defining a longitudinal axis. The method further comprises the steps of providing a sleeve including an outer surface, first and second ends and a center portion intermediate the first and second ends, and supporting the first end of the sleeve vertically above the patient support surface and horizontally off-center from the longitudinal axis. The method further comprises the steps of positioning the sleeve around the patient wherein a portion of the outer surface engages the patient support surface, fastening the second end of the sleeve to the center portion thereof, lowering the patient support surface relative to the sleeve wherein the outer surface of the sleeve is in spaced relation to the patient support surface, and raising the patient support surface into contact with a portion of the outer surface of the sleeve, thereby defining a pivot point on the sleeve. A further step comprises rolling the sleeve about the pivot point thereby placing the patient in a prone position on the patient support surface.

In another illustrative embodiment of the present invention, a proning device is provided comprising a patient support surface extending between opposing first and second longitudinal side edges, a drive roller supported adjacent the first side edge, and an idler roller supported above the patient support surface. A sheet is supported by the patient support surface and includes a first sleeve portion configured to placed adjacent a chest of a patient, a second sleeve portion configured to be placed adjacent a back of a patient, and a connecting portion extending between the first portion and the drive roller. At least one fastener releasably secures the second sleeve portion to the first sleeve portion, thereby defining a sleeve for receiving the patient.

Features and advantages of the invention will become apparent to those skilled in the art upon consideration of the following detailed description of the illustrated embodiment exemplifying the best mode of carrying out the invention as presently perceived.

BRIEF DESCRIPTION OF THE DRAWINGS

The detailed description particularly refers to the accompanying figures in which:

FIG. 3 is a perspective view similar to FIG. 2 with supports attached to the base;

FIG. 4 is a sectional view taken along line 4-4 of FIG. 3, illustrating a hose and line clip integrally formed with the base of the proning apparatus;

FIG. 55 is an end view, in partial schematic, of the proning apparatus of FIG. 54;

FIG. 56 is an end view similar to FIG. 55, illustrating operation of the proning apparatus;

FIG. 57 is an end view similar to FIG. 55, illustrating further operation of the proning apparatus;

FIG. 61 is an end view similar to FIG. 60, illustrating the proning apparatus;

FIG. 62 is an end view similar to FIG. 60, illustrating operation of the proning apparatus;

FIG. 63 is an end view similar to FIG. 60, illustrating further operation of the proning apparatus;

FIG. 64 is an end view, with a partial cut away, illustrating an alternative embodiment of the proning apparatus of FIG. 60;

FIG. 65 is a side elevational view of the proning apparatus of FIG. 64;

FIG. 67 is an end view, in partial schematic, illustrating the proning apparatus of FIG. 66;

FIG. 68 is an end view similar to FIG. 67, illustrating operation of the proning apparatus;

FIG. 69 is an end view similar to FIG. 67, illustrating further operation of the proning apparatus;

FIG. 71 is an end view, in partial schematic, illustrating the proning apparatus of FIG. 70;

FIG. 72 is an end view similar to FIG. 71, illustrating operation of the proning apparatus; and FIG. 73 is an end view similar to FIG. 71, illustrating further operation of the proning apparatus.

DETAILED DESCRIPTION OF THE DRAWINGS

Figure 1:
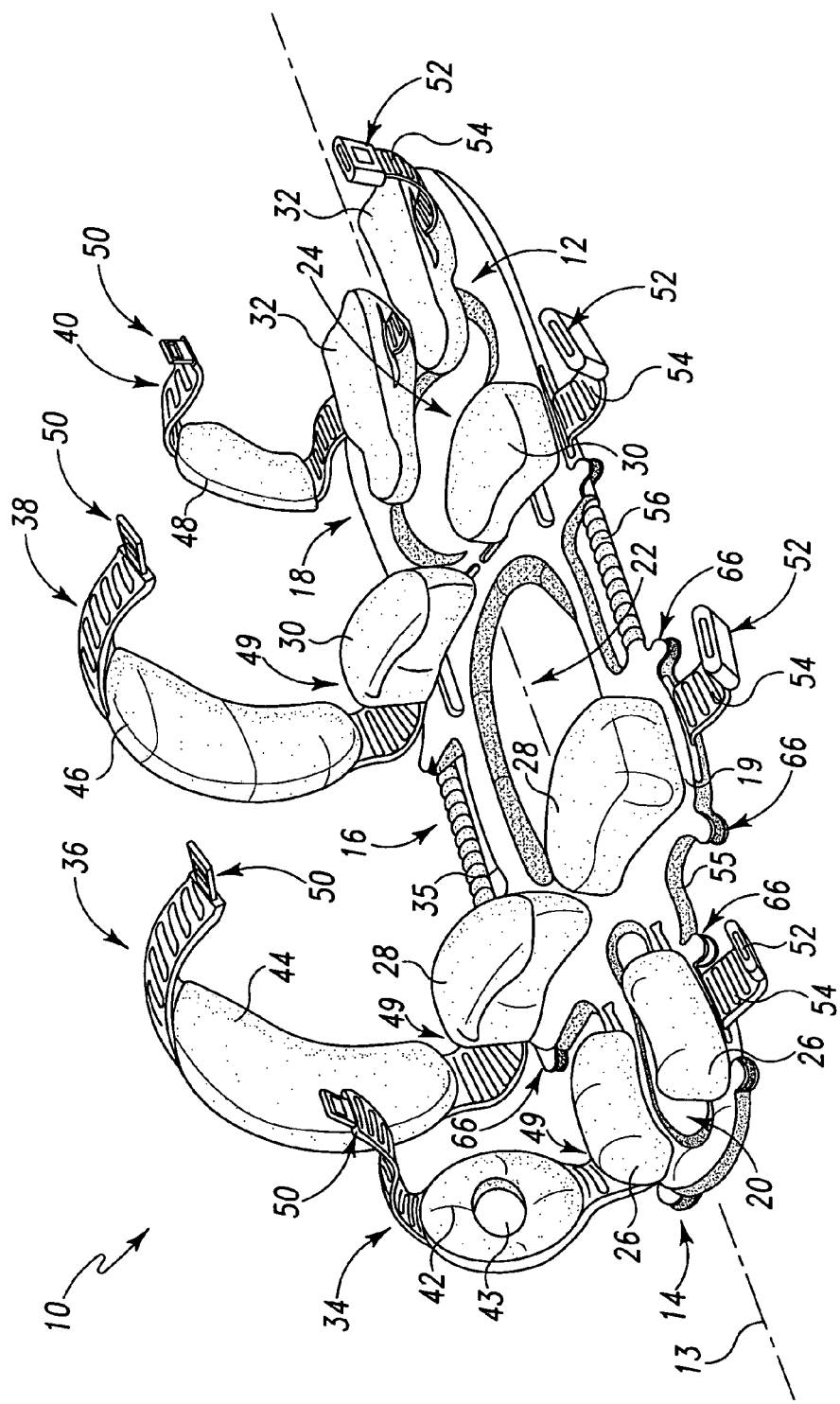
FIG. 1 is a perspective view of a proning apparatus according to one embodiment of the present invention.

Referring now to the drawings, FIGS. 1-7 illustrate a proning apparatus 10 according to one exemplary embodiment of the present invention. The apparatus 10 includes a unitary base 12 defining a longitudinal axis 13 and having head portion 14, a body portion 16, and a leg portion 18. The body portion 16 includes a shoulder section 19 and is positioned intermediate the head portion 14 and the leg portion 18. Head portion 14 includes a face-receiving aperture 20 substantially centered along the longitudinal axis 13 and adapted to receive the face of a patient therein. Body portion 16 includes an abdomen-receiving aperture 22 in spaced relation to the face-receiving aperture 20 and substantially centered along the longitudinal axis 13. The leg portion 18 includes a groin receiving aperture 24 in spaced relation to the abdomen-receiving aperture 22 and substantially centered along the longitudinal axis 13. The abdomen-receiving aperture 22 is adapted to expose the abdomen of a patient 23 and the groin-receiving aperture 24 is adapted to expose the groin of the patient 23 when the face of the patient supported on the base 12 is received within the face-receiving aperture 20.

Adjustable supports, preferably head support cushions 26, are releasably secured to head portion in lateral spaced relation on opposite sides of the face-receiving aperture 20. Shoulder supports, preferably cushions 28, are releasably secured to the shoulder section 19 of the body portion 16 intermediate the abdomen-receiving aperture 22 and the face-receiving aperture 20. Hip supports, preferably cushions 30, are also releasably secured to body portion 16, intermediate the groin-receiving aperture 24 and the abdomen-receiving aperture 22. Leg supports, preferably cushions 32, are releasably secured to leg section 18 and are longitudinally spaced from the hip support cushions 30 on an opposite side of the groin-receiving aperture 24. All of the cushions 26, 28, 30 and 32 may be secured to the base 12 by suitable fasteners such as hook and loop fasteners, snaps, straps, or the like.

Figure 2:
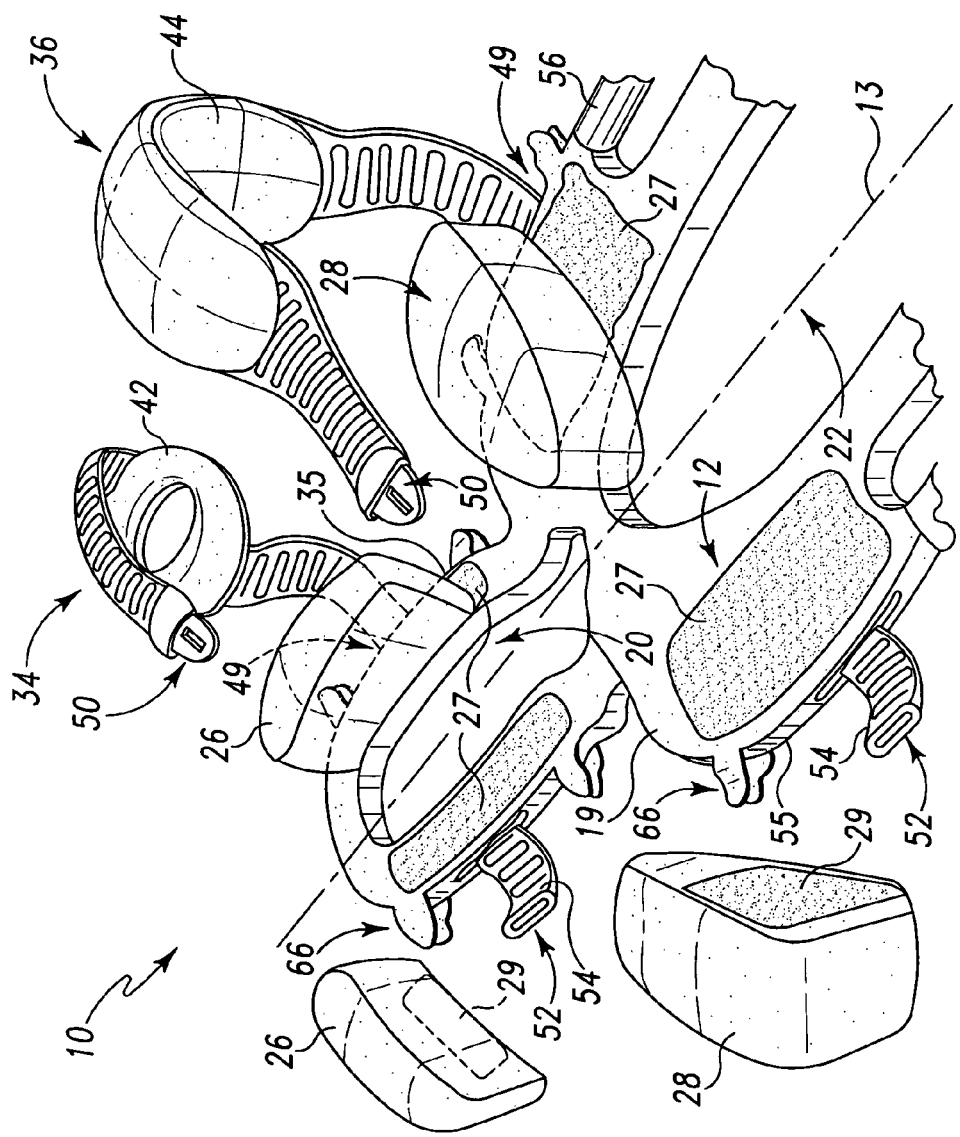
FIG. 2 is a partial perspective view of the proning apparatus of FIG. 1, illustrating details of movable supports positioned on a base adjacent head and body portions.

FIGS. 1 and 2 illustrate the adjustability of cushions 26, 28, 30 and 32. Illustratively, hook and loop fasteners are utilized with the hook portion 27 coupled to the base 12 and mating loop portions 29 coupled to the support cushions 26, 28, 30 and 32. By using adjustable fasteners, the cushions 26, 28, 30 and 32 may be positioned at desired locations to engage and support the patient. Cushions 26, 28, 30 and 32 are illustratively formed from a pressure reducing material such as gel packs, foam, air bladders, beads or other pressure reducing filler material in order to reduce concentrated pressure from being applied to distinct portions of the body of the patient 23.

A head strap 34 is coupled to head portion 14 at a first side 35 of the base 12. A shoulder strap 36, a hip strap 38, and a leg strap 40 are also coupled to the first side 35 of the base 12. Head strap 34 includes a circular padded section 42 including a contoured recess 43 for engaging the back of a patient's head. Straps 36, 38, and 40 include padded sections 44, 46, and 48, respectively, for engaging portions of the patient's body. The padded sections 42, 44, 46, and 48 are positioned intermediate opposing first and second ends 49 and 50 of the respective straps 34, 36, 38, and 40. Free second ends 50 of straps 34, 36, 38, and 40 are configured to be coupled to free ends 52 of straps 54 coupled to an opposite second side 55 of the base 12 as shown in FIG. 1. Caregiver gripping handles 56 are formed on opposite sides 35 and 55 of the base 12 to facilitate proning of the patient 23 as discussed below.

Figure 5:
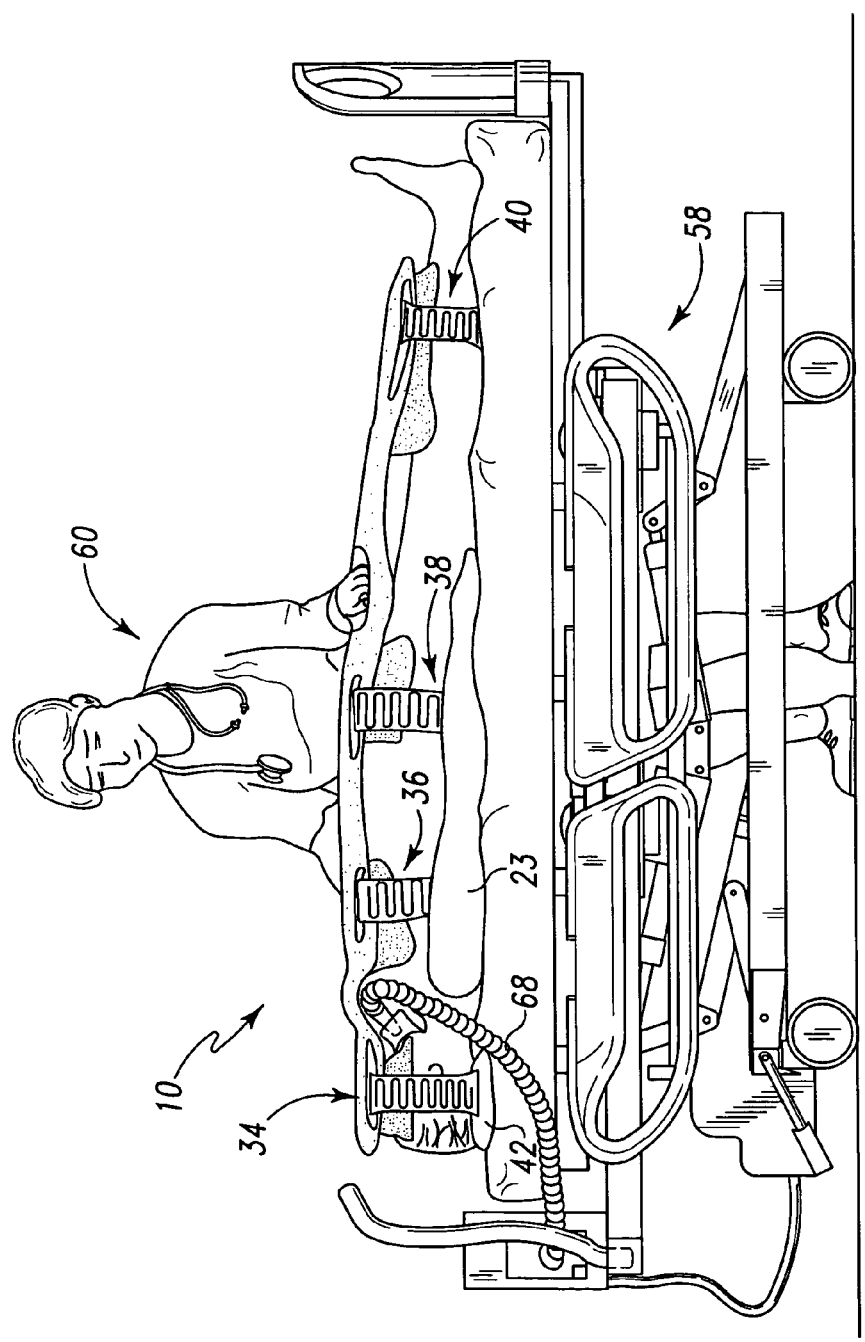
FIG. 5 is a side elevational view illustrating the proning apparatus of FIG. 1 installed upon a patient located on a bed, with a caregiver located adjacent one side of the patient.
Figure 6:
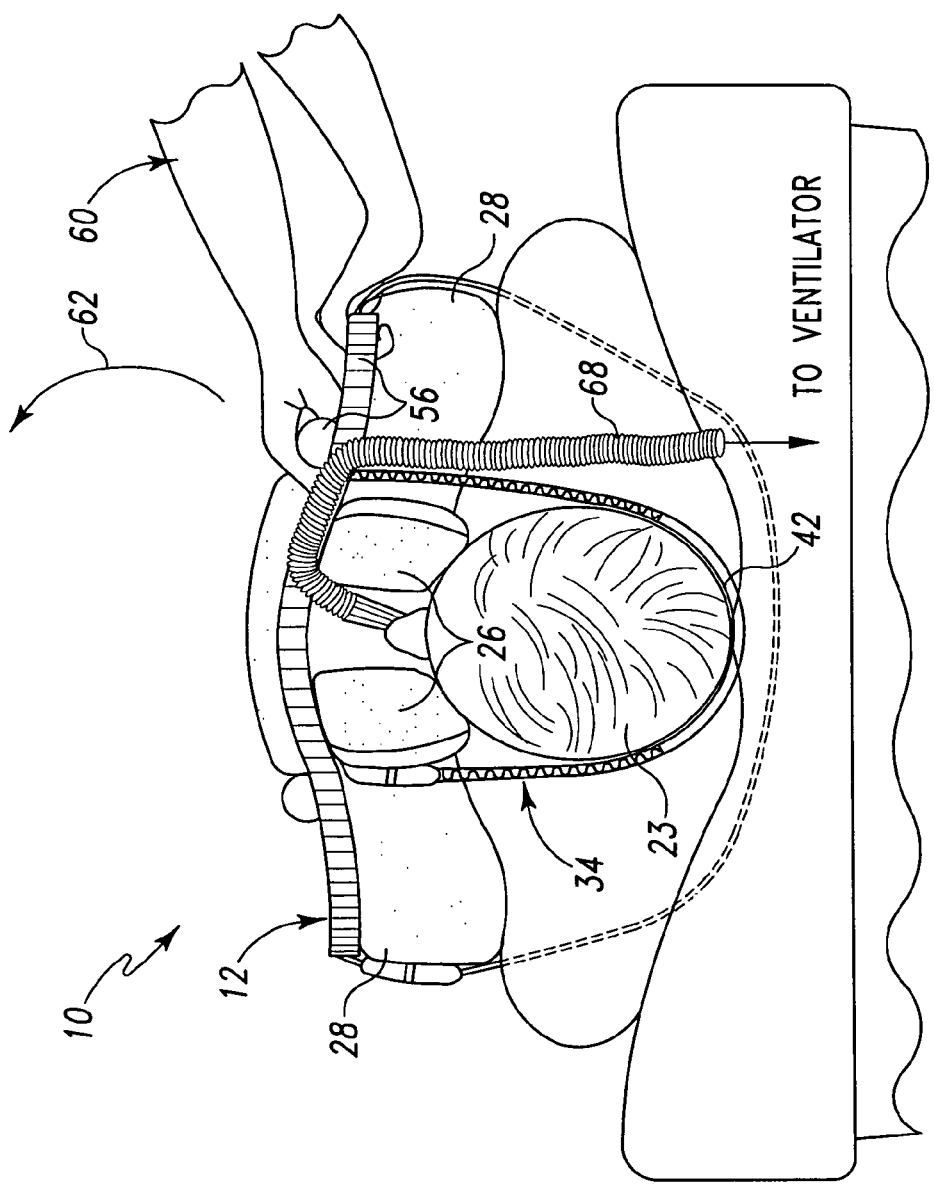
FIG. 6 is an end view of the proning apparatus of FIG. 1, illustrating caregiver gripping handles in preparation for proning the patient.

In operation, straps 34, 36, 38, and 40 are placed underneath a patient lying on a bed 58 as shown in FIG. 5. A caregiver 60 can grip the base 12 by way of the handles 56, as shown in FIG. 6, and then rotate the patient as illustrated by arrow 62 from the supine position (i.e. face up) shown in FIG. 6 to the prone position (i.e. face down) shown in FIG. 7. As detailed above, proning is believed to be an effective intervention to increase oxygenation in a patient 23 suffering from acute respiratory distress syndrome (ARDS). When in the prone position, the support cushions 26, 28, 30, and 32 help reduce the likelihood of formation of pressure ulcers on the skin of the patient 23 by reducing concentrated pressure applications.

Figure 7:
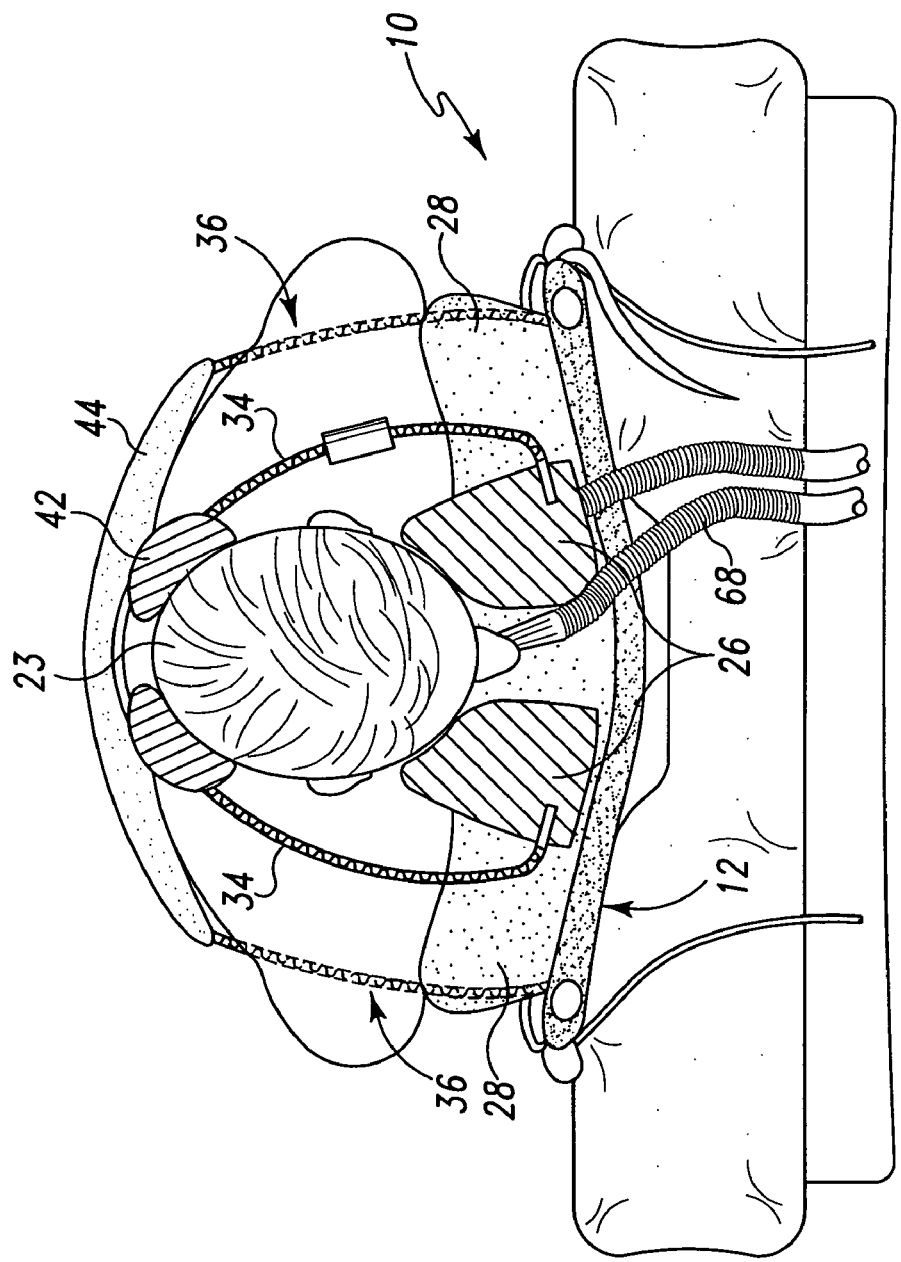
FIG. 7 is an end view of the proning apparatus of FIG. 1, illustrating the patient in a prone position.
Figure 8:
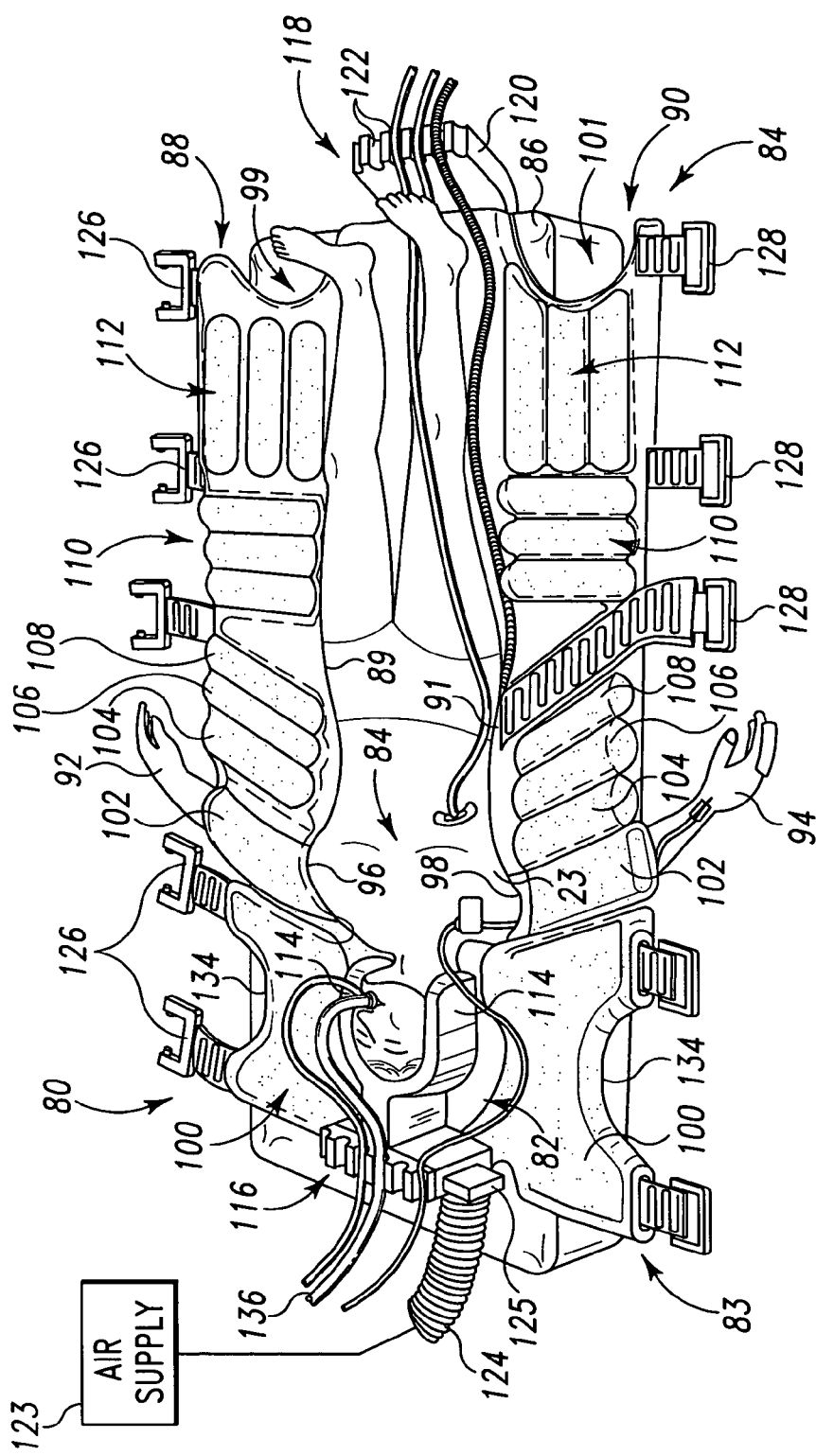
FIG. 8 is a perspective view of a proning therapy sleeve according to another embodiment with the present invention.
Figure 9:
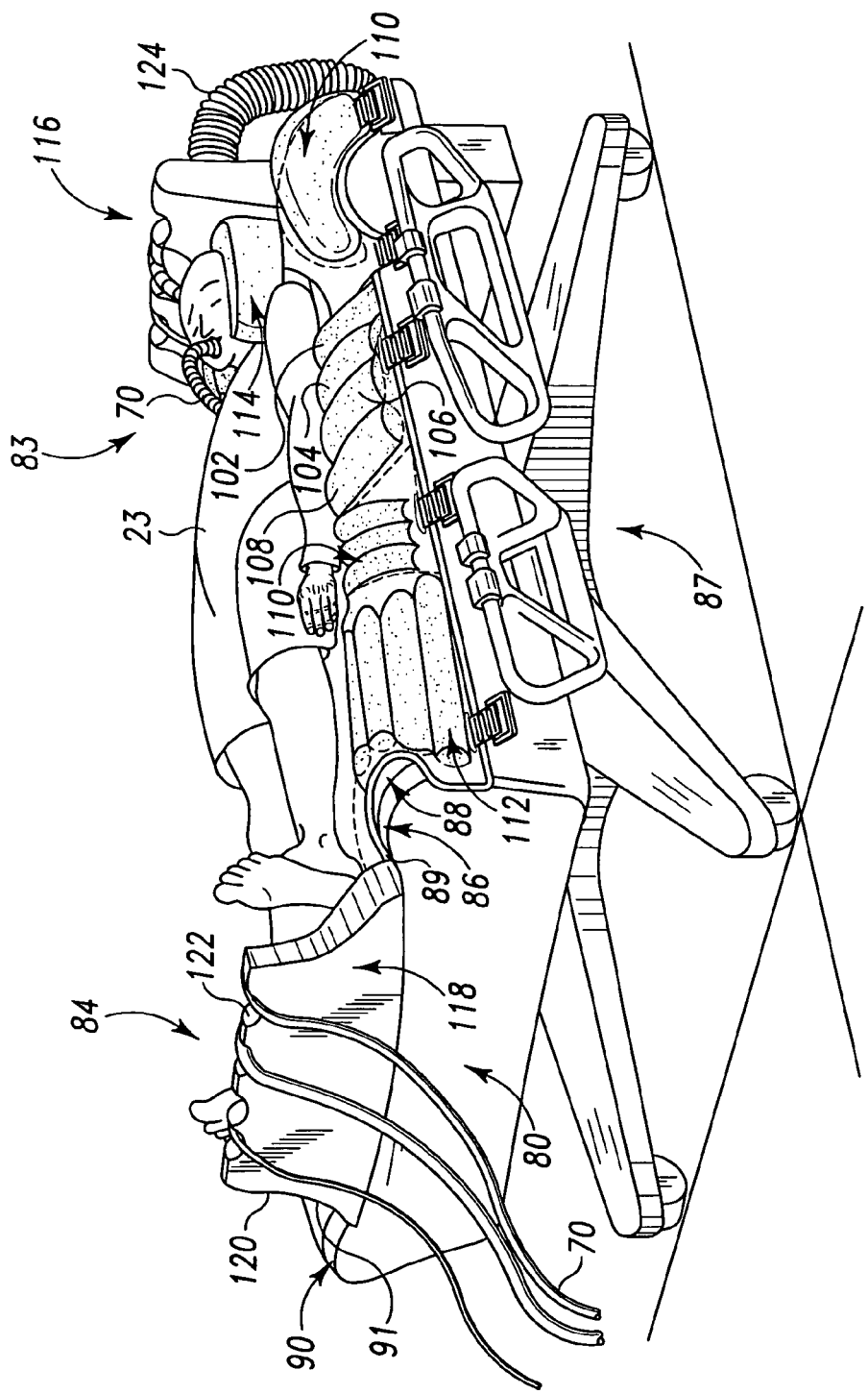
FIG. 9 is a perspective view of the proning sleeve of FIG. 8 supported on a hospital bed.

As best shown in FIGS. 2 and 4, the base 12 is formed to include a plurality of line management devices, preferably hose and line clips 66, for holding various hoses 68 and lines 70 in position adjacent to the base 12. These clips 66 are supported adjacent the side edges 35 and 55 of the base 12 and include top and bottom spring arms 72 and 74. The arms 72 and 74 are biased toward each other to permit insertion and retention of the tubes and lines 68 and 70 into the clips 66. Therefore, ventilator tubes such as tube 68, as well as other lines such as feeding lines, drainage lines and intravenous (IV) lines can be routed through the clips 66 to manage the tubes and lines during proning of the patient 64. The head aperture 20 and cushions 26 permit the ventilator tube 68 to be routed to the patient 23 during proning as best shown in FIGS. 6 and 7.

Another embodiment of the present invention is illustrated in FIGS. 8-12 as comprising a proning therapy sleeve 80 having a bottom surface or support portion 82 located underneath a patient 23. Bottom support portion 82 includes opposing head and foot ends 83 and 84 and is configured to be located on a conventional support surface or mattress 86 of a bed 87. Proning therapy sleeve 80 includes opposing side portions 88 and 90 which are connected to and extend outwardly from opposing side edges 89 and 91 of the support portion 82. More particularly, the side portions 88 and 90 are configured to be located on opposite sides of the patient 23. The patient's arms 92 and 94 extend through apertures 96 and 98 formed in the side portions 88 and 90, respectively. Foot clearance notches 99 and 101 are likewise formed in the side portions 88 and 90, respectively, to receive the feet of the patient 23.

Each of the side portions 88 and 90 includes a head support bladder 100, and a plurality of chest support bladders 102, 104, 106, and 108. Each side portion 88 and 90 also includes a thigh engaging bladder 110 and a calf engaging bladder 112. The patient's head is illustratively supported by side supports 114 located on opposite sides of the patient's head.

The therapy sleeve 80 includes a head end line management apparatus 116 and a foot end line management apparatus 118. Each line management apparatus 116 and 118 includes a body section 120 having a plurality of notches or slots 122 configured to receive tubes and lines 68 and 70. A main air supply line 124 illustratively couples the head end line management apparatus 116 to a conventional external air supply 123. A plurality of valves and sensors are illustratively provided either on the therapy sleeve 80, or on a separate controller in a control module 125 coupled to the bed 87 for selectively supplying air to the various air zones located on the first and second side portions 88 and 90.

Figure 10:
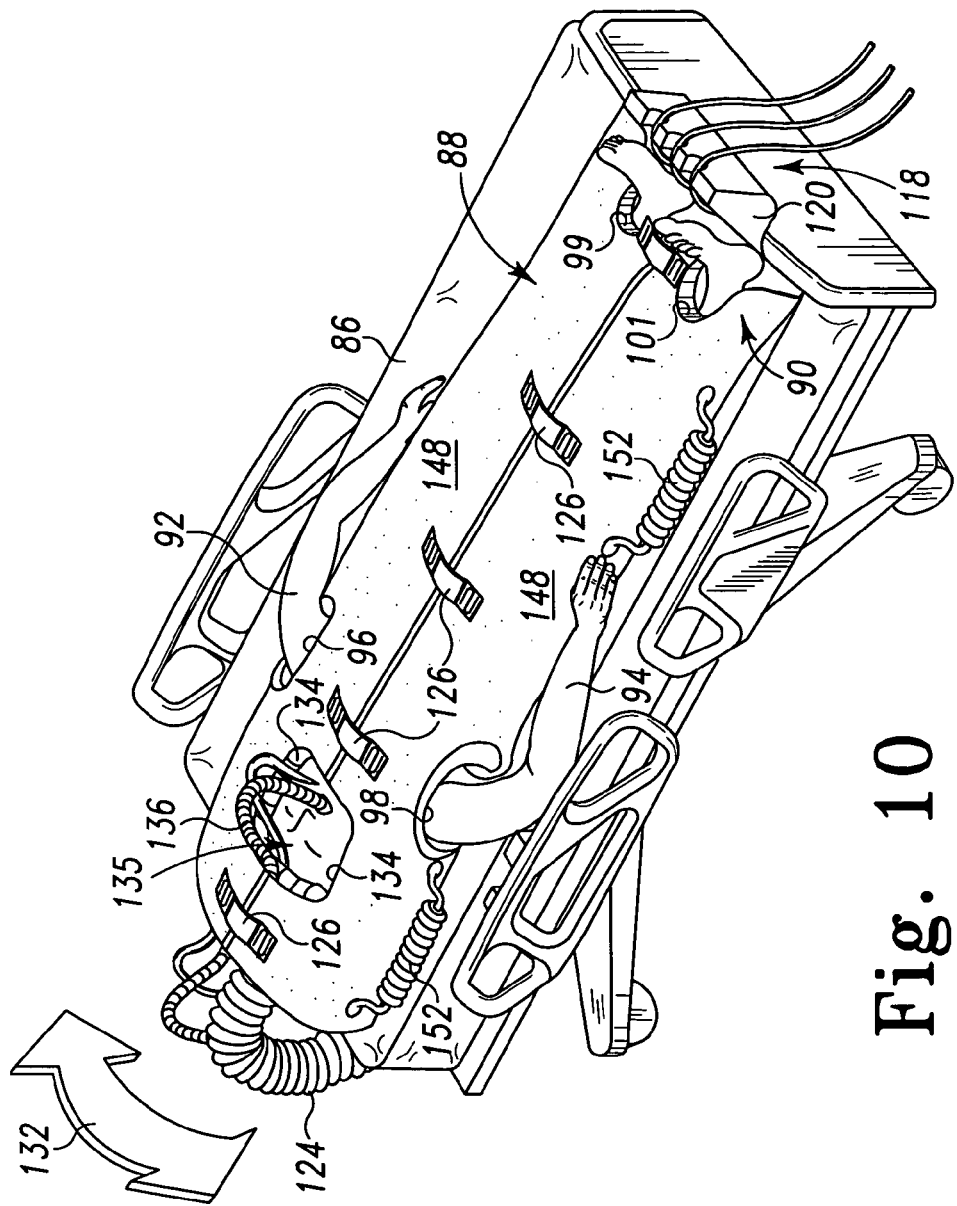
FIG. 10 is a perspective view illustrating side portions of the proning sleeve of FIG. 8 folded over the front portion of the patient and latched.
Figure 11:
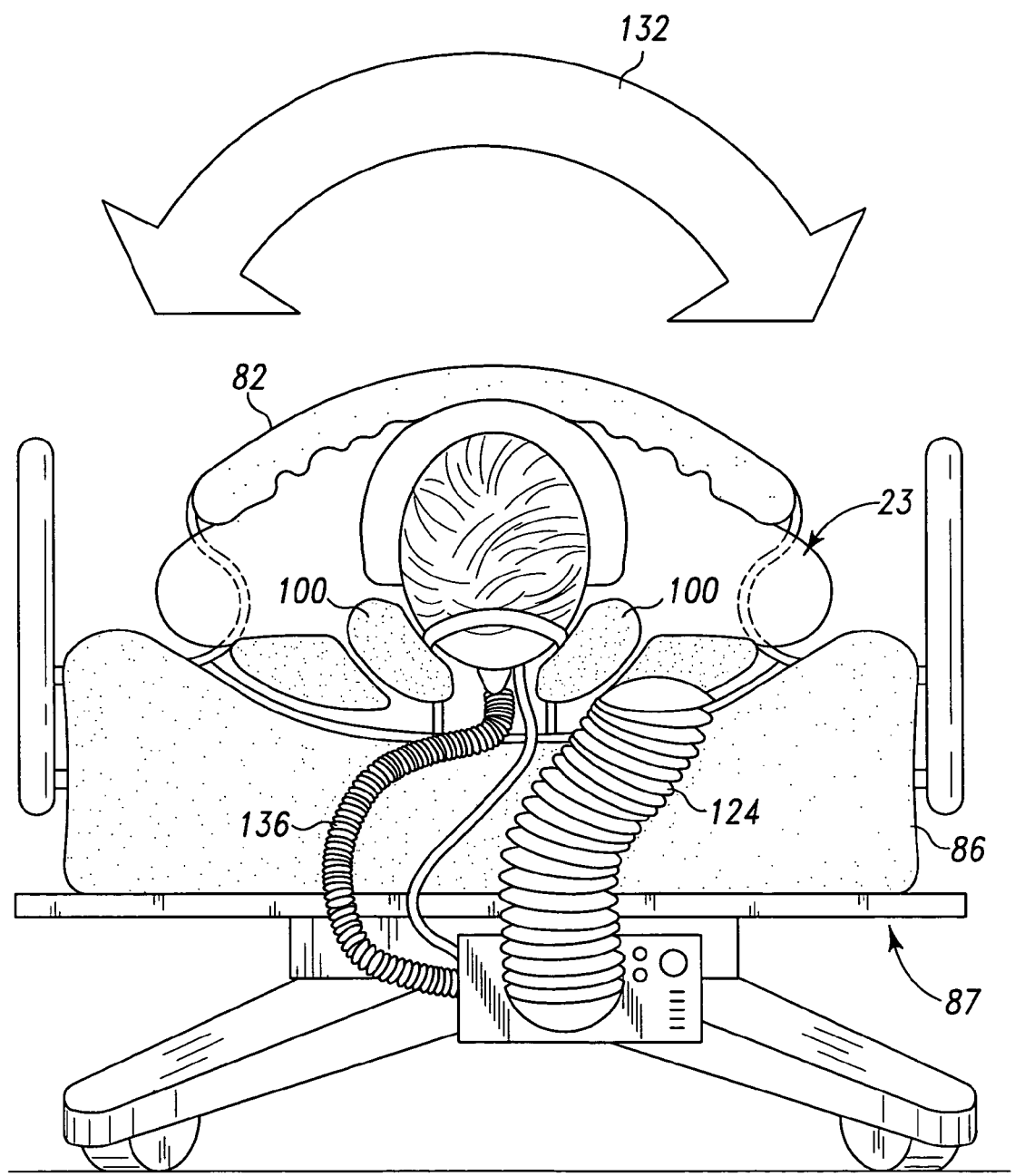
FIG. 11 is an end view of the proning sleeve of FIG. 10, illustrating the patient in a prone position on the bed.

First side portion 88 includes a plurality first fastener members 126 and second side portion 90 includes a plurality of second fastener members 128 configured to mate with the first fastener members 126. In operation, the first and second side portions 88 and 90 are folded over the front of patient 23 and fastener members 126 and 128 are connected as best shown in FIG. 10. Illustratively, conventional buckles are shown as fastener members 126 and 128 in the FIG. 8 embodiment. It is understood that other suitable fasteners such as hook and loop fasteners, snaps, ties, or the like may be used to secure the first and second side portions 88 and 90 together as shown in FIG. 10.

Caregiver gripping handles 152 are supported by an outer surface of the opposing first and second side portions 88 and 90. When the side portions 88 and 90 are secured together as illustrated in FIG. 10, then the handles 152 are positioned on opposite sides of the therapy sleeve 80 to facilitate rotation of the patient 23 to and from the prone position of FIG. 11, as illustrated by double-headed arrow 132.

Head bladders 100 include semi-circular recessed portions 134 which cooperate to define a face receiving aperture 135 when the side portions 88 and 90 are folded over the patient 84 as best shown in FIG. 10. The bladders 100, 102, 104, 106, 108, 110, and 112 provide support for the patient in the prone position. In addition, the bladders 100, 102, 104, 106, 108, 110, and 112 may be used to provide therapy to the patient. For instance, bladders 102 may be inflated to provide chest binding and compression when a ventilator is used to supply air or oxygen to the patient through a ventilator tube 136. As air supplied from an external source is blown into the patient's lungs, bladders 102 are inflated to force air downwardly into the patient's lungs.

Bladders 102, 104, 106 and 108 may also provide percussion and vibration therapy on the patient. In addition, the bladders 112, 110, 108, 106, 104, and 102 can be sequentially inflated to assist in blood circulation within the patient 23. Additional details regarding chest binding and compression therapy is provided below.

Figure 12:
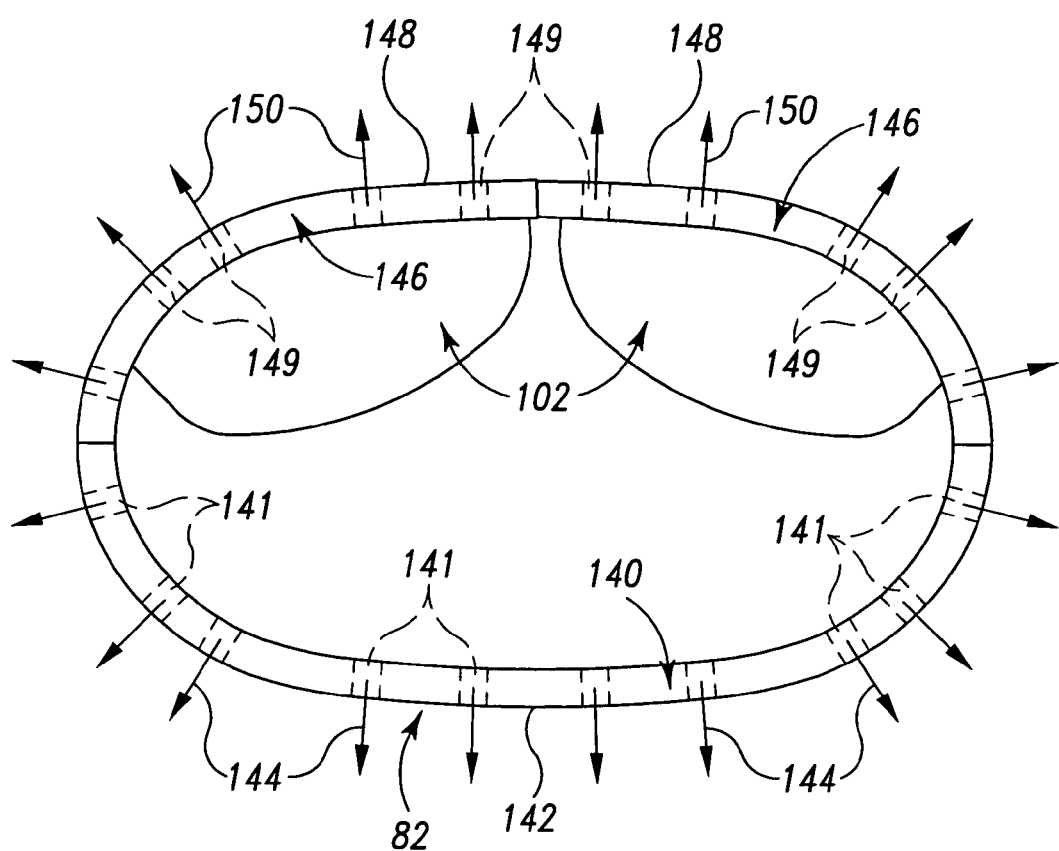
FIG. 12 is a diagrammatical sectional view illustrating outwardly directed airflow from an outer bladder and illustrating internal compression bladders of the proning therapy sleeve of FIG. 11.

In one illustrated embodiment of the present invention illustrated in FIG. 12, the bottom support portion 82 includes an air zone or chamber 140 coupled to the air supply 123. When air is supplied to the chamber 140, air is forced outwardly through a plurality of holes or apertures 141 formed in an outer lower surface 142, as illustrated by arrows 144. The air exiting the apertures 141 defines an air pallet or bearing to assist in rotational movement of the sleeve 80 containing the patient 23. In addition, side portions 88 and 90 include an outer chamber 146 coupled to the air supply 123. An outer surface 148 includes a plurality of holes or apertures 149 so that air flows outwardly through the outer surfaces 148 as illustrated by arrows 150, again providing an air bearing to facilitate rotation of the sleeve 10 and patient 23. Therefore, the proning therapy sleeve 10 provides outwardly directly air forming an air bearing around substantially its entire outer circumference to facilitate proning of the patient 23.

Figure 13:
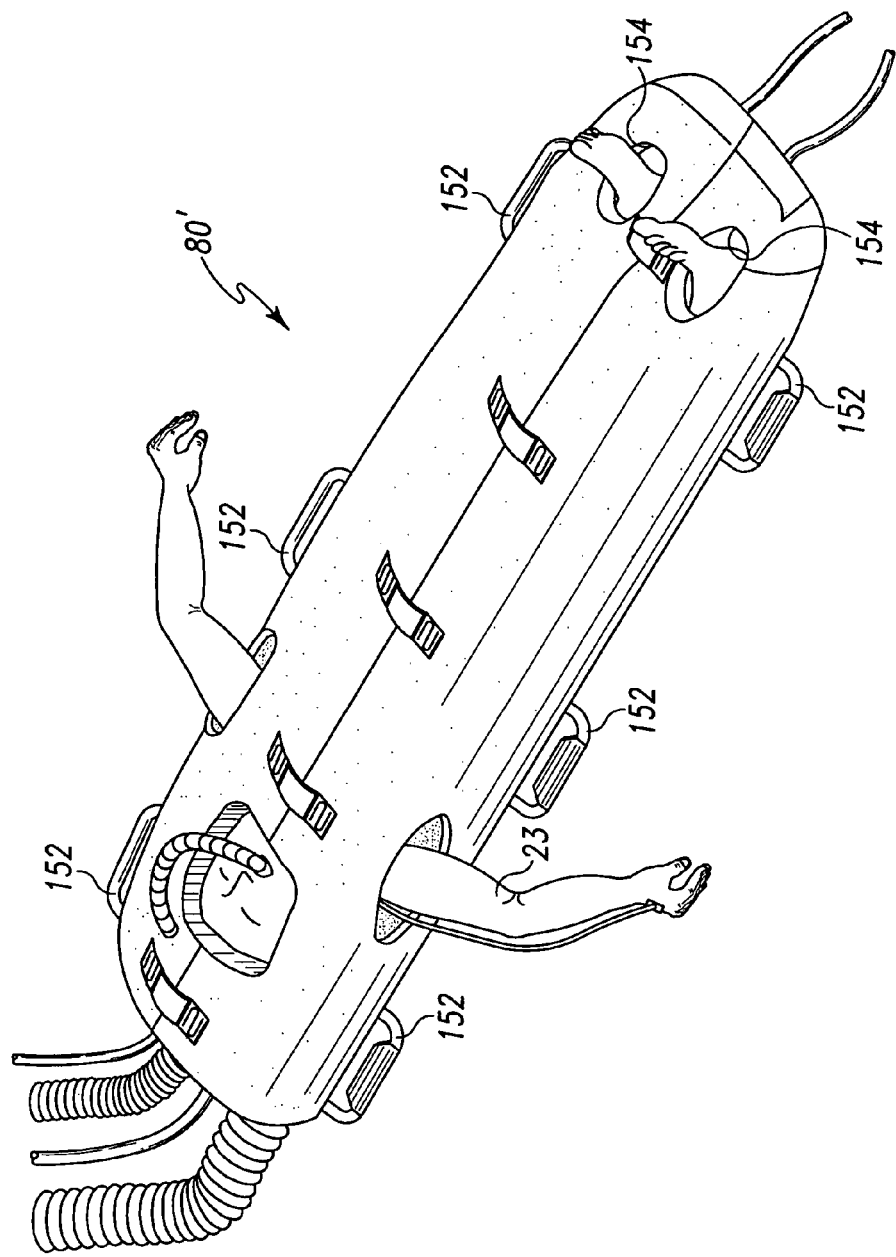
FIG. 13 is a perspective view of a proning therapy sleeve according to another embodiment of the present invention.

As illustrated in FIG. 13, the proning therapy sleeve 80' may be utilized on any conventional patient support and its applicability is not limited to hospital beds 87. In FIG. 13, the sleeve 80' includes a plurality of spaced apart handles 152 on opposite sides of the sleeve 80' to facilitate proning of the patient 23. Sleeve 80' also includes foot-receiving apertures 154 formed in each of the first and second side portions 88 and 90.

Figure 14:
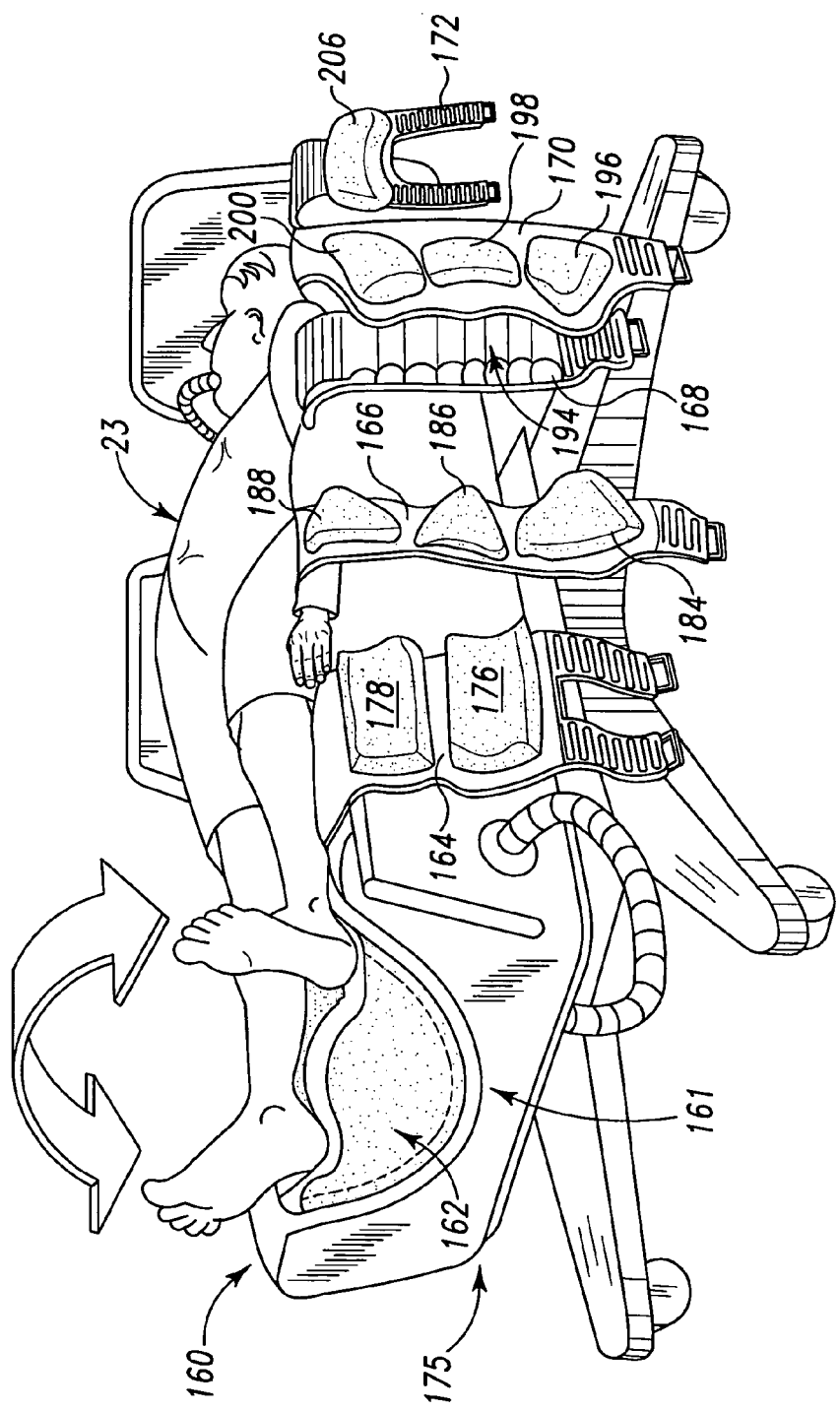
FIG. 14 is a perspective view of a proning apparatus according to another embodiment of the present invention, including a proning surface formed integrally with an air bearing platform on a bed.
Figure 15:
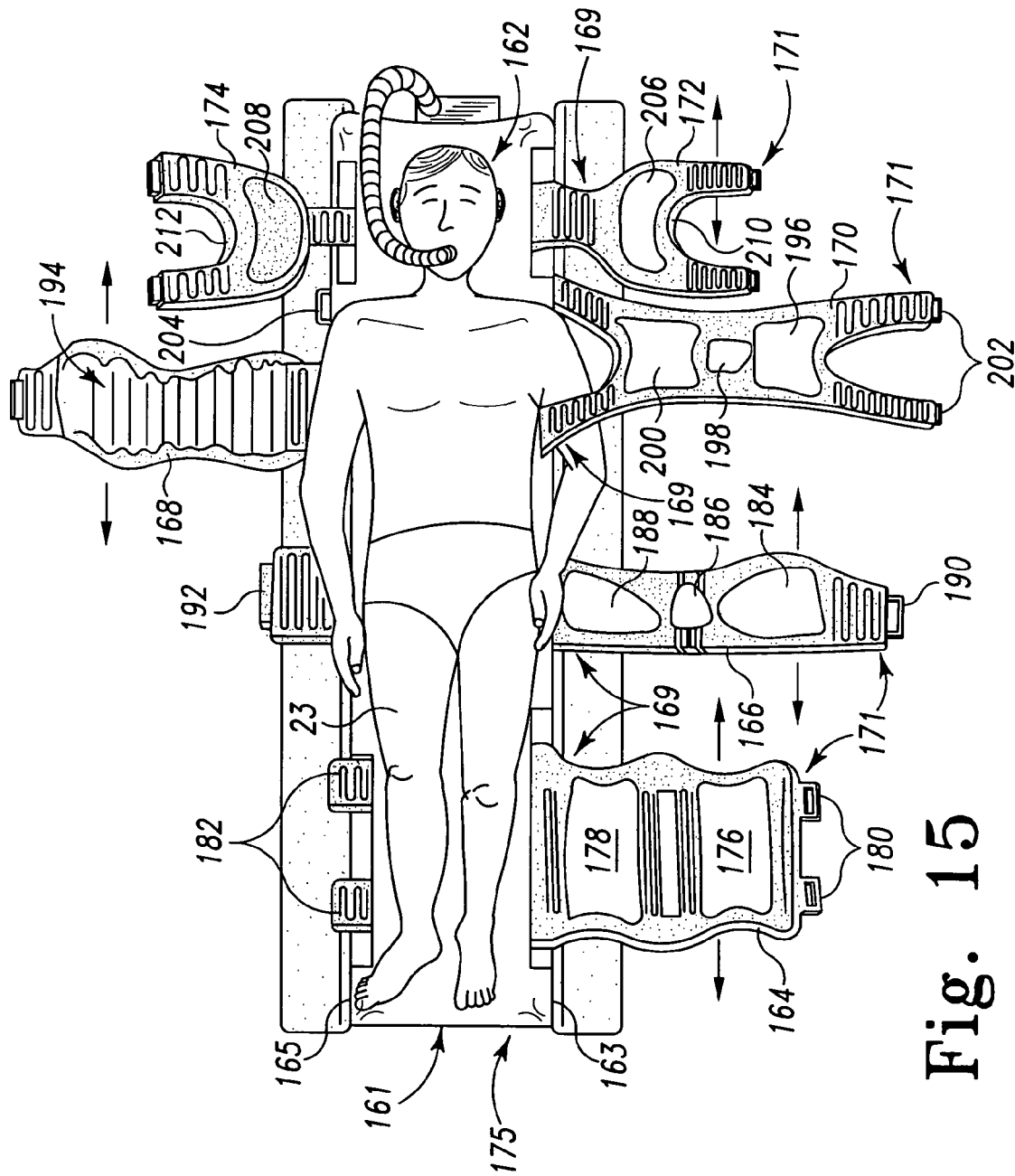
FIG. 15 is a top plan view of the proning apparatus of FIG. 14.

FIGS. 14-18 illustrate another embodiment of the present invention. As shown in FIG. 14, a proning apparatus 160 includes a base 161 having a bottom support bladder 162 and opposing first and second sides 163 and 165. A plurality of side flaps 164, 166, 168, 170, 172, and 174 each include a first end 169 coupled to the first side 163 of the support bladder 162. In other words, the base 161 forms a portion of the patient support surface on a bed 175. Leg support cushions 176 and 178 are coupled to leg support flap 164. Fasteners 180 are supported by the second end 171 of the flap 164 and configured to mate with fasteners 182 on the opposite side 165 of bladder 162. Hip support cushions 184, 186, and 188, are coupled to hip support flap 166. A fastener 190 is supported by the second end 171 of the flap 166 and configured to be coupled to a fastener 192 on opposite side 165 of the bladder 162. A plurality of bladders 194 are coupled to chest support flap 168. Bladders 194 are selectively inflated to support the patient 23 in a prone position and to provide chest binding or percussion therapy vibration therapy on the patient 23.

Body support cushions 196, 198, and 200 are coupled to chest support flap 170. Fasteners 202 on flap 170 are configured to be coupled to fasteners 204 on opposite side 165 of bladder 162. A head bladder 206 is coupled to flap 172 and another head bladder 208 is coupled to flap 174. Flaps 172 and 174 include a U-shaped recesses 210 and 212, respectively. When the flaps 172 and 174 are coupled together by suitable fasteners, an aperture 214 is provided for the patient's face as best shown in FIG. 16.

Figure 16:
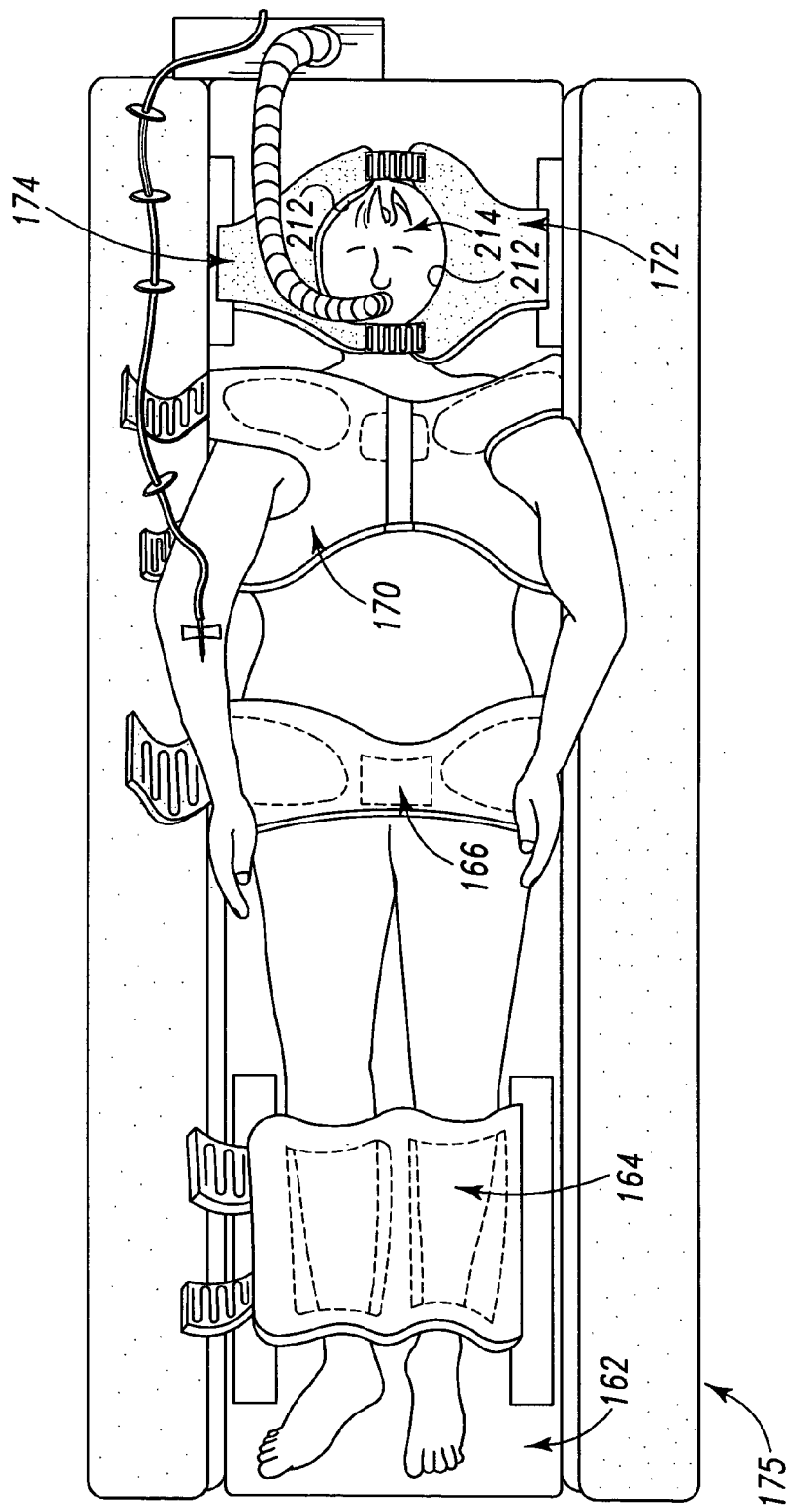
FIG. 16 is a top plan view similar to FIG. 15, with the proning surface located over the patient.
Figure 17:
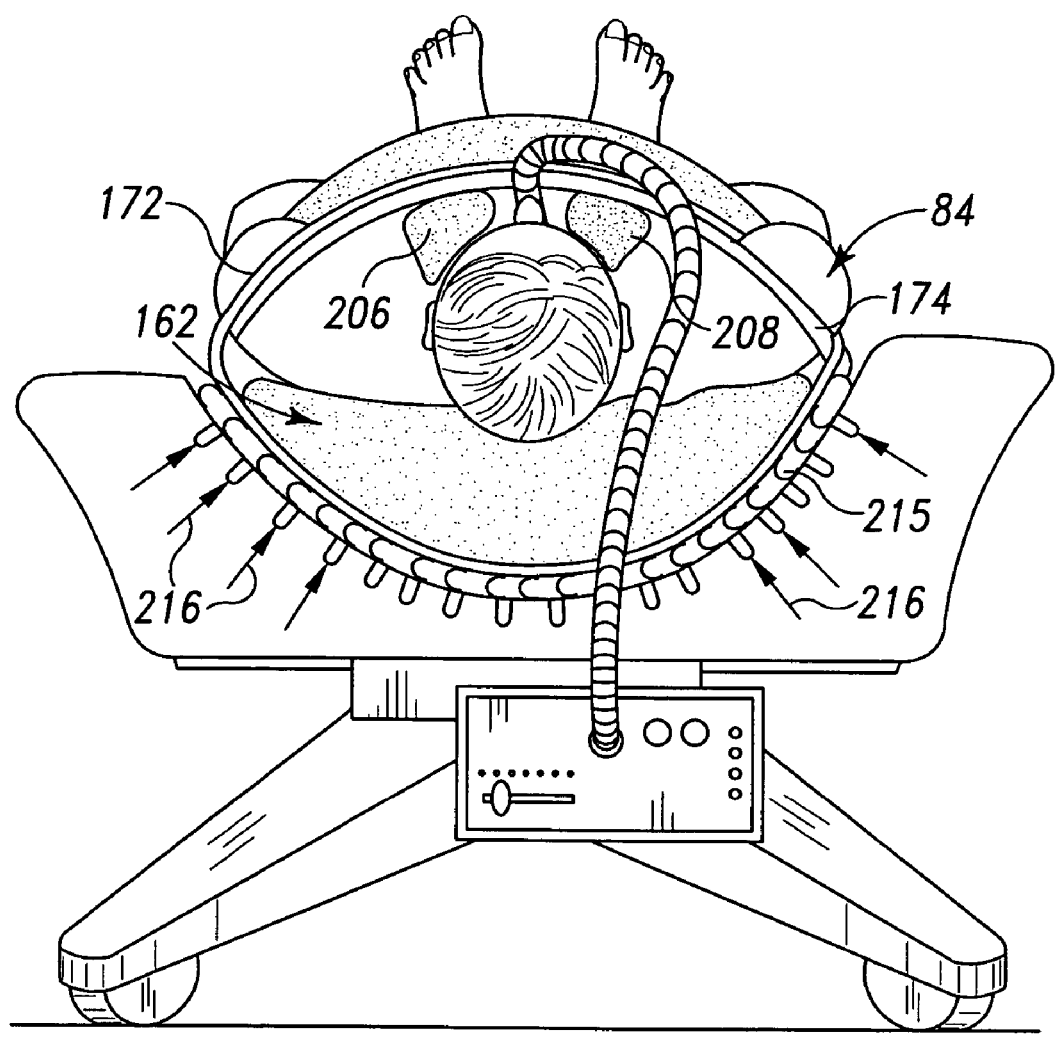
FIG. 17 is an end view of the proning apparatus of FIG. 16, illustrating the patient in a supine position on the bed.
Figure 18:
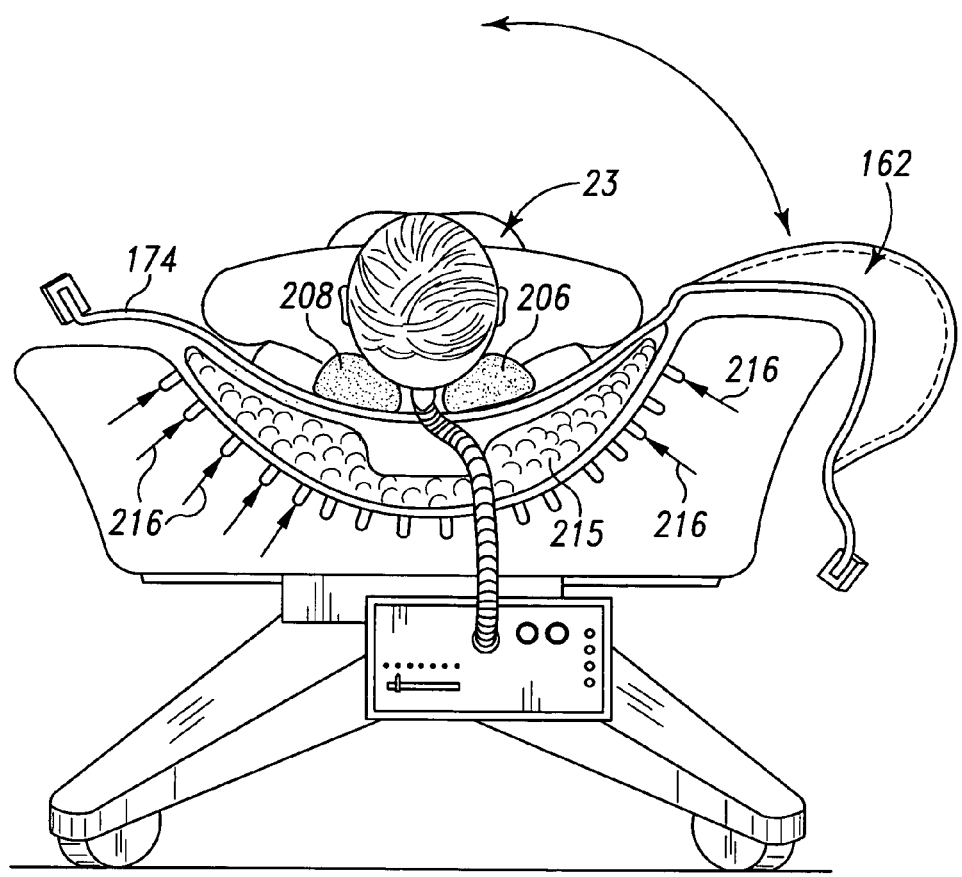
FIG. 18 is an end view of the bed and proning apparatus of FIG. 16, illustrating the patient in a prone position on the bed.

In operation, air is supplied to bladder 162 to provide support for the patient 184 when in the supine position as shown in FIGS. 14-17. When it is desired to prone the patient 84, flaps 164, 166, 168, 170, 172, and 174 are folded over the front of the patient and secured as best illustrated in FIG. 16. In one embodiment of the present invention, air flows outwardly from the bottom surface of bladder 162 to provide an air pallet or bearing to facilitate rotation of the patient 84 from the supine position shown in FIG. 17 to the prone position shown in FIG. 18. As the patient is rotated to the prone position, air is supplied to a normally deflated prone bladder 215 as illustrated by arrows 216, so that the bladder 215 is inflated to support the patient 23 in the prone position. Once in the prone position, the fasteners of the flaps 164, 166, 168, 170, 172 and 174 are disconnected and bladder 162 can be rotated away from the patient 23 to expose the patient's posterior side. The support cushions 176, 178, 184, 188, 196, 198, 200, 206, and 208 remain under the patient to provide support in the prone position.

Figure 19:
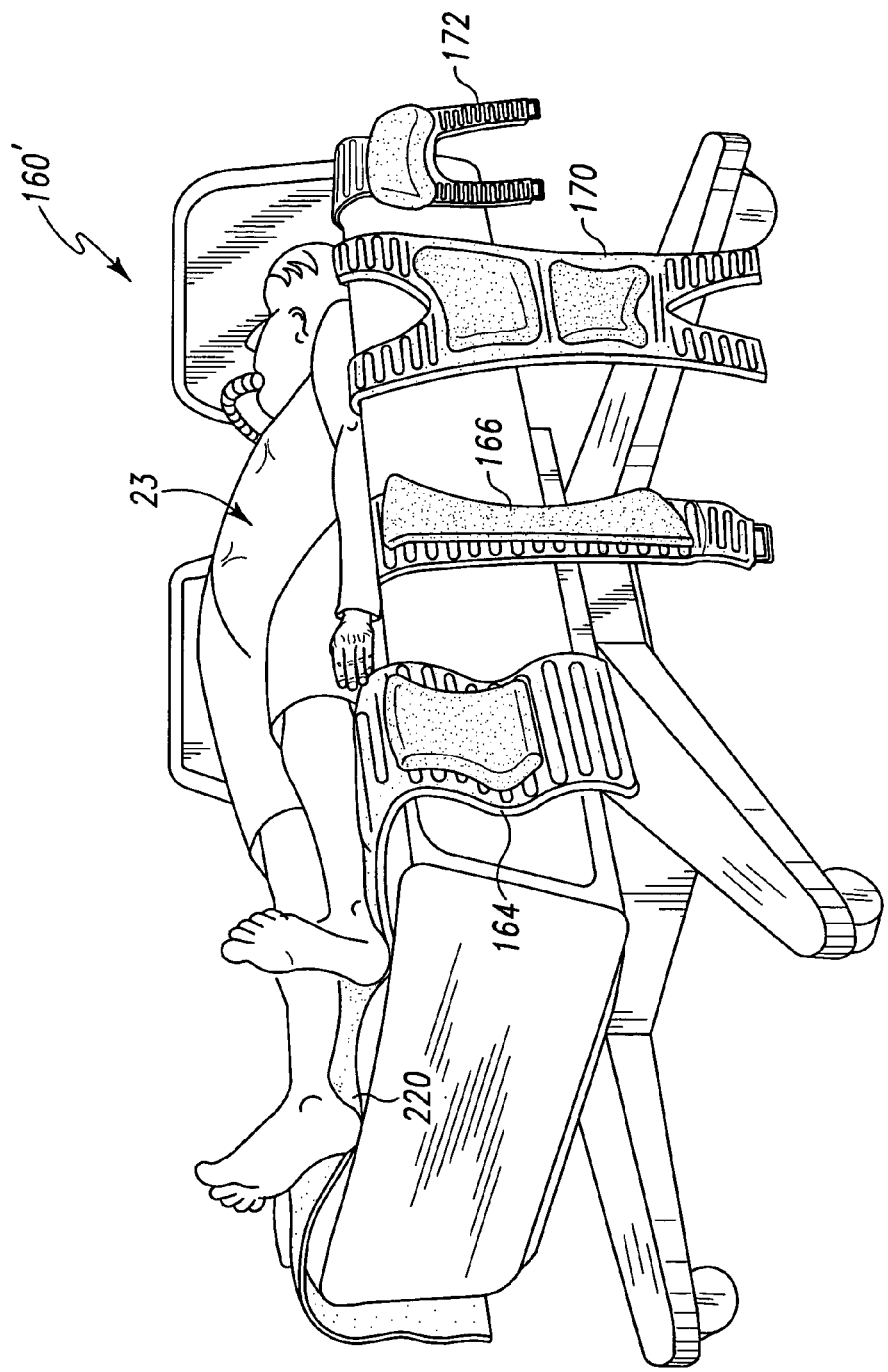
FIG. 19 is a perspective view of another embodiment a proning apparatus according to another embodiment of the present invention, in which a proning sleeve is located on a conventional support surface of a bed.
Figure 20:
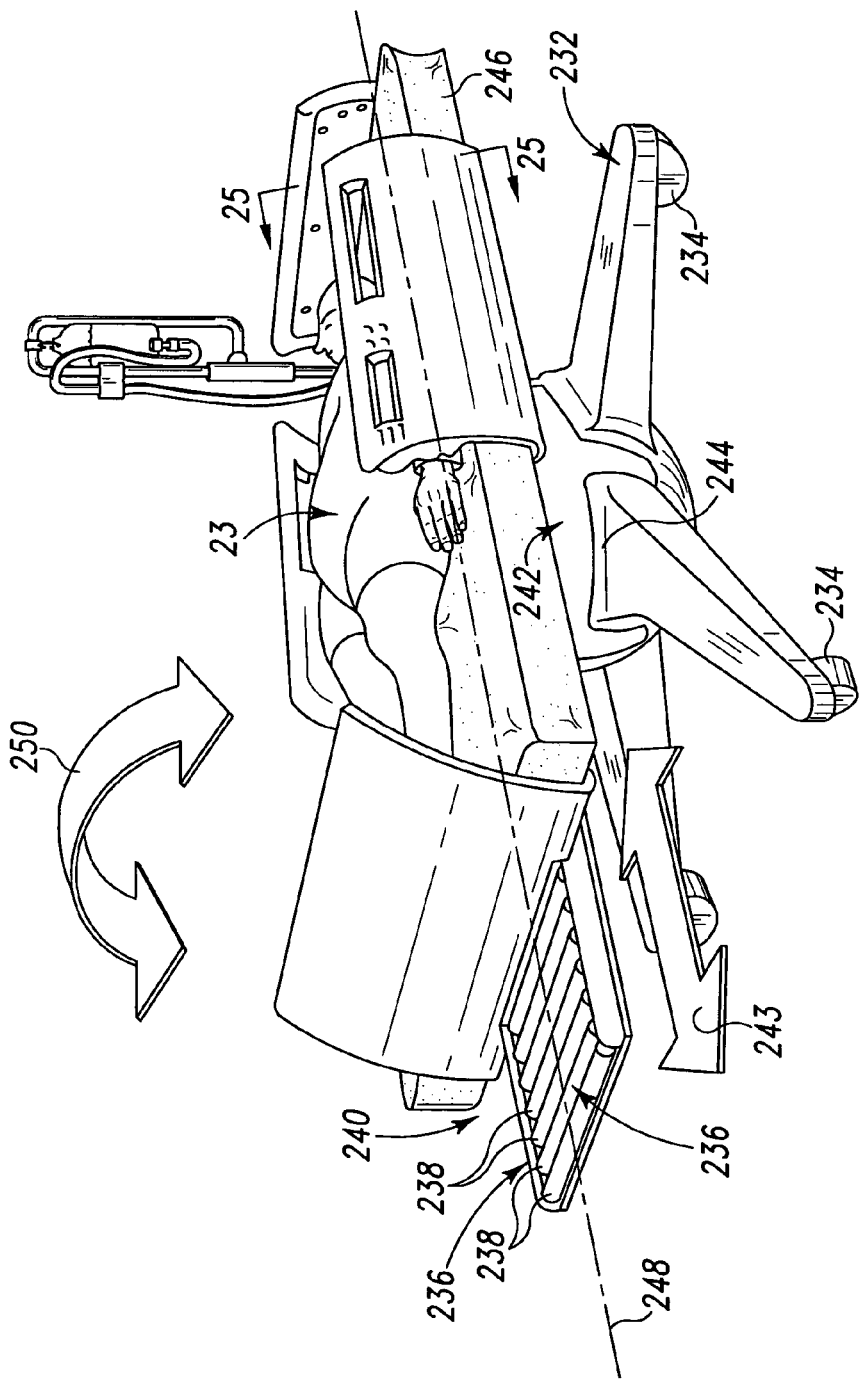
FIG. 20 is a perspective view of a multi-directional rotation platform according to another embodiment of the present invention.

FIG. 19 illustrates another embodiment of the proning apparatus 160' present invention similar to FIGS. 14-18 in which the inflatable air bladder 162 is replaced with a thinner sheet or air bladder 220 located below the patient 23. The sheet 220 rests on a conventional mattress. Flaps 164, 166, 170, 172, and 174 are operated in a manner as described above when it is desired to prone the patient.

FIGS. 20-25 illustrate another embodiment of the present invention. In this embodiment, a multi-directional rotation platform 230 includes a base 232 having a plurality of castors 234. Base 232 supports an inner frame 236 having a plurality of rollers 238. An outer movable frame 240 supporting the patient support surface 246 is coupled to the inner frame 236 for longitudinal movement in the directions of double headed arrow 250. A drive mechanism is provided to move the outer movable frame 240 relative to inner frame 236 back and forth in the direction of double headed arrow 250 at selected rates. Such reciprocating movement provides therapy to the patient 23 and stimulates production of nitric oxide by the patient 23. See, for example, PCT International Publication No. WO 98/39996 owned by NIMS, Inc. which is incorporated herein by reference.

Figure 21:
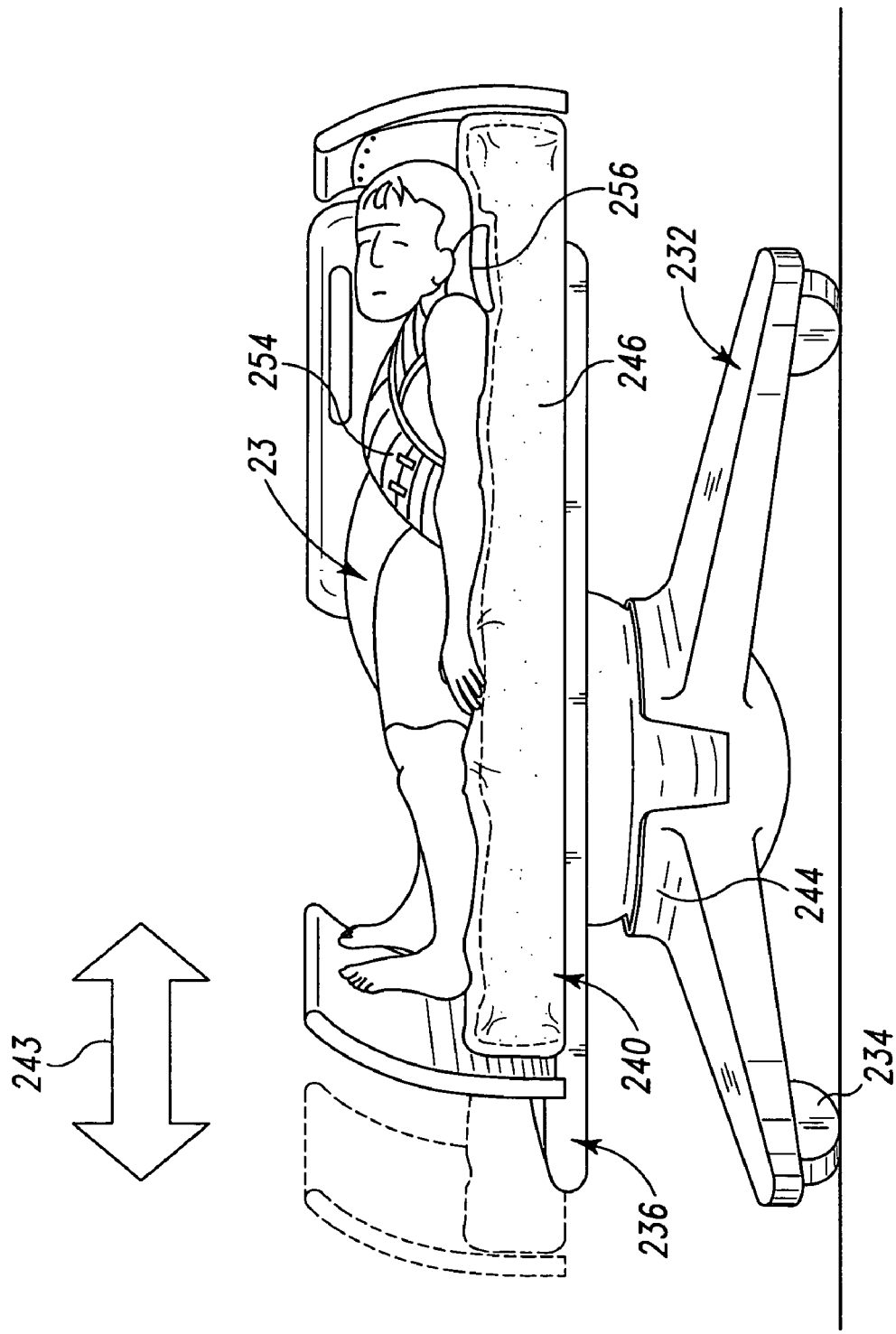
FIG. 21 is a side elevational view of the platform of FIG. 20, illustrating longitudinal movement of a patient support surface relative to a base.
Figure 22:
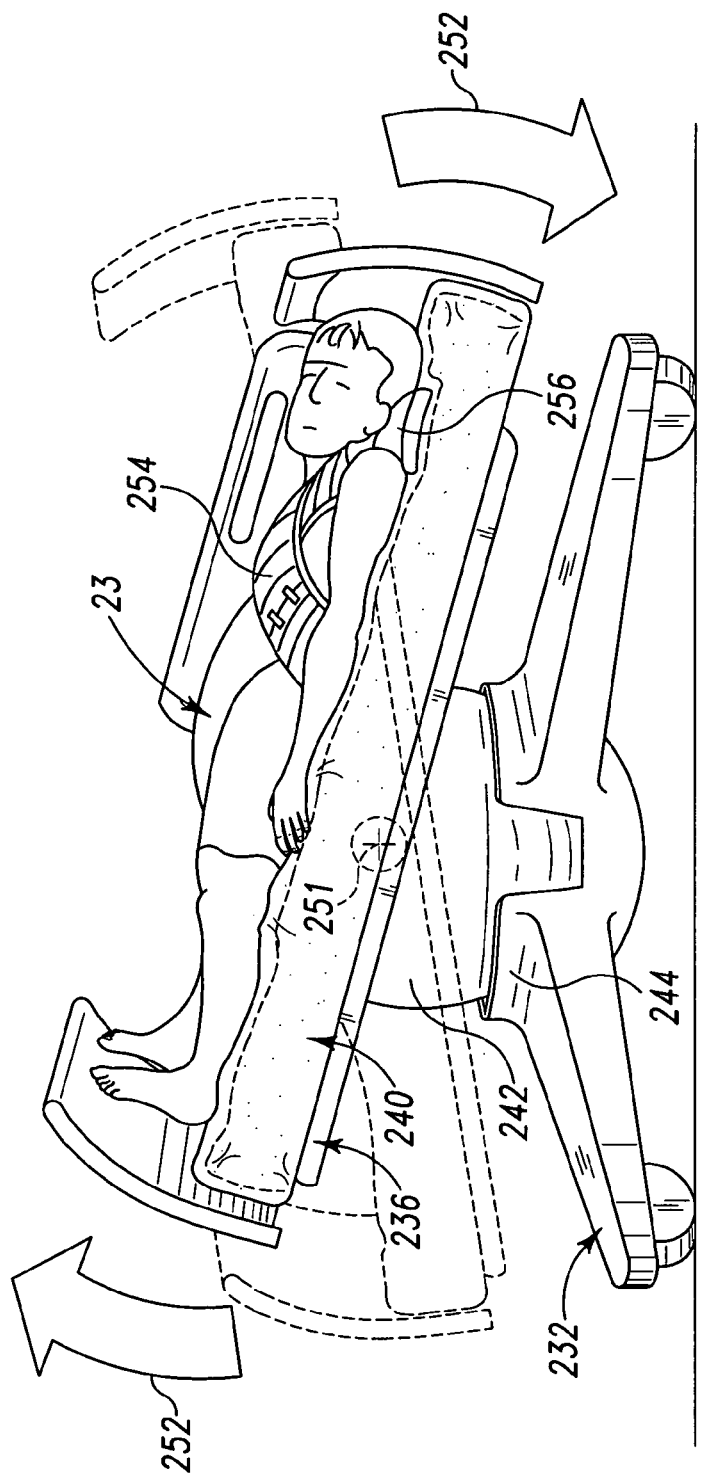
FIG. 22 is a side elevational view similar to FIG. 21, illustrating pivotable movement of the patient support surface about a transverse pivot axis between a Trendelenburg position and a reverse Trendelenburg position.
Figure 23:
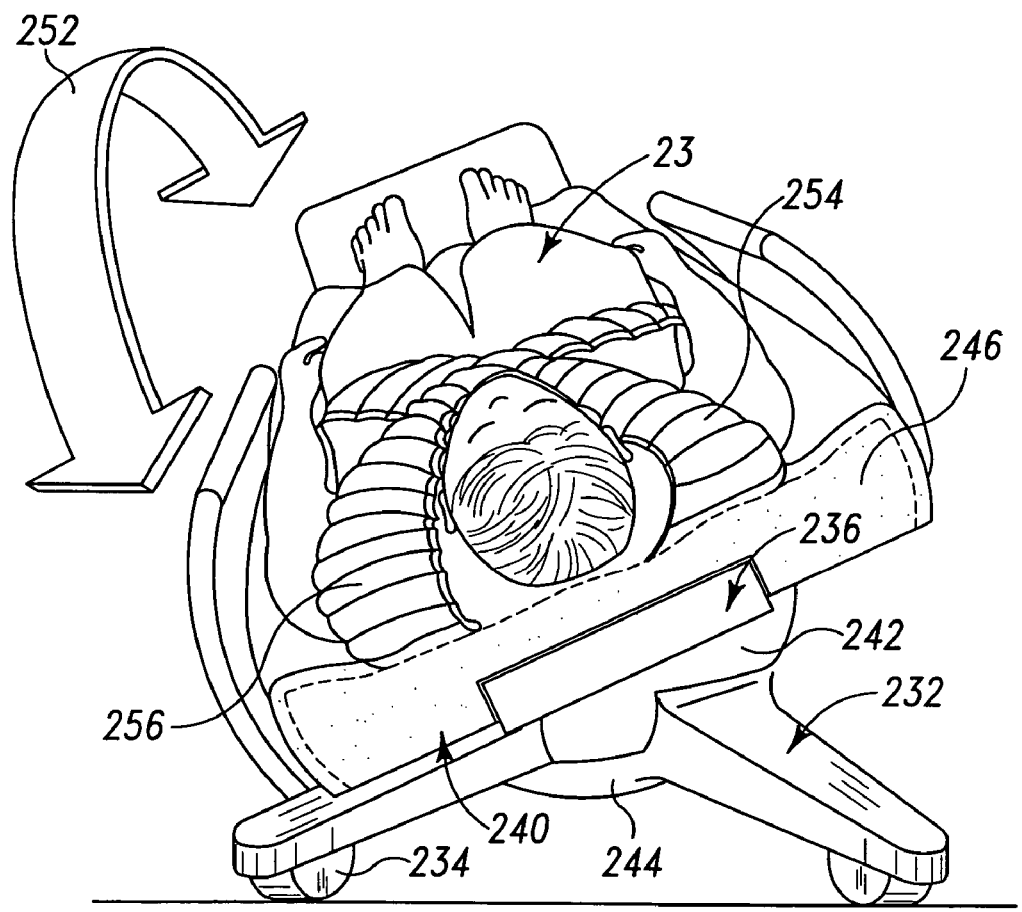
FIG. 23 is an end view of the platform of FIG. 20, illustrating rotation of the patient support surface about a longitudinal axis when the support surface is in the Trendelenburg position.
Figure 24:
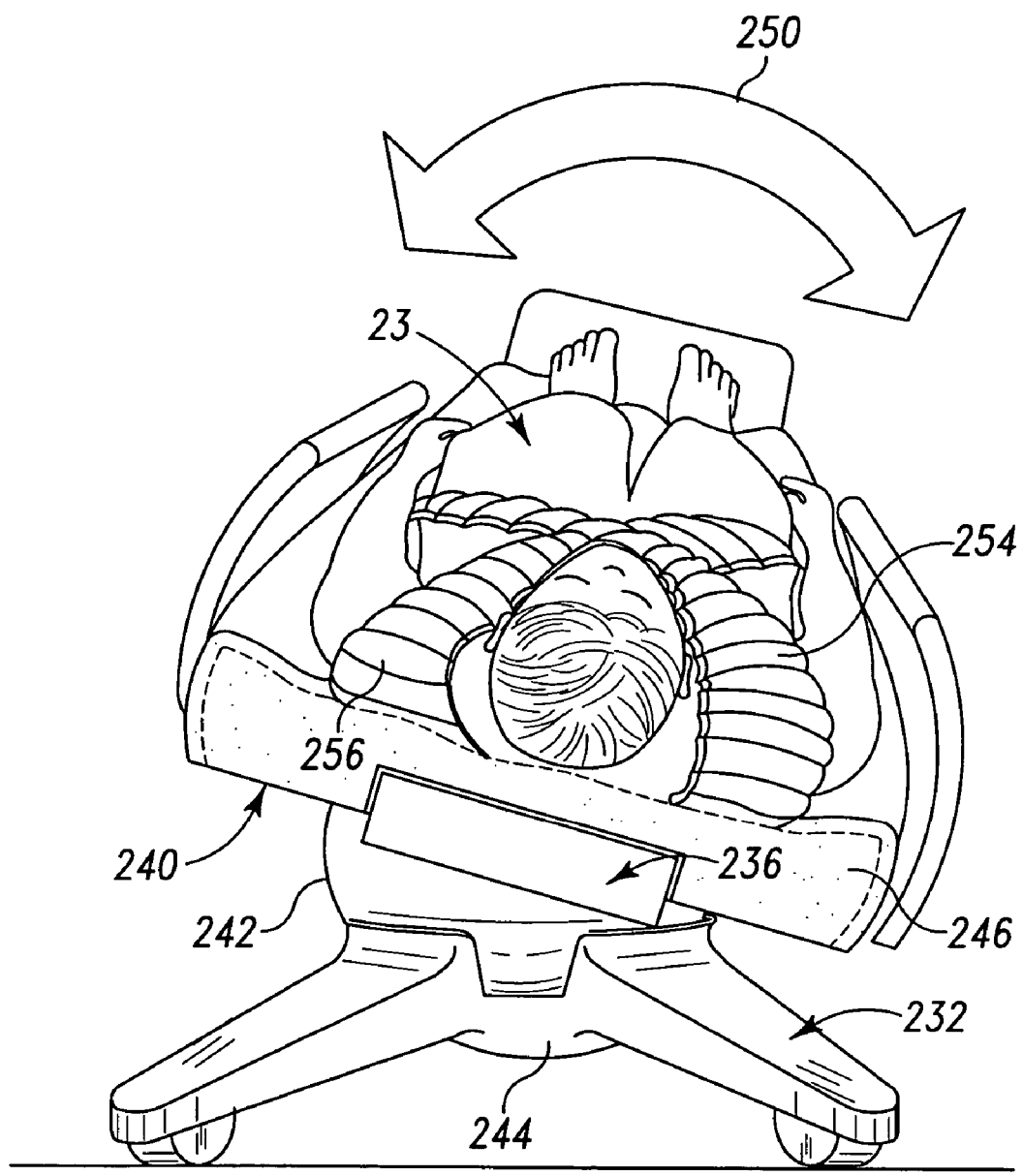
FIG. 24 is an end view similar to FIG. 23 in which the support surface is rotated in an opposite direction.

Frames 236 and 240 are coupled to base 232 by a suitable connecting mechanism such as a ball 242 and socket 244. Therefore, the patient support surface 246 supported by frames 236 and 240 is pivotable about a longitudinal axis 248 as illustrated by double headed arrow 250 in FIG. 20 and FIG. 24. In addition, the frames 236 and 240 and patient support surface 246 are rotatable about a transverse axis 251 between a Trendelenburg and reverse Trendelenburg positions as best shown in FIG. 22. FIG. 21 illustrates reciprocating movement along the longitudinal axis 248 in the direction of double headed arrow 243. Movement about the transverse pivot axis 251 is illustrated by arrows 252 in FIG. 22. Illustratively, the patient 23 is secured to the patient support surface 246 by straps 254 and 256. As illustrated in FIGS. 23 and 24, the patient support surface 246 is rotatable about the longitudinal axis 248 and the transverse axis 251 at the same time to move patient 23 to a desired position for percussion/vibration therapy or other therapy.

Figure 25:
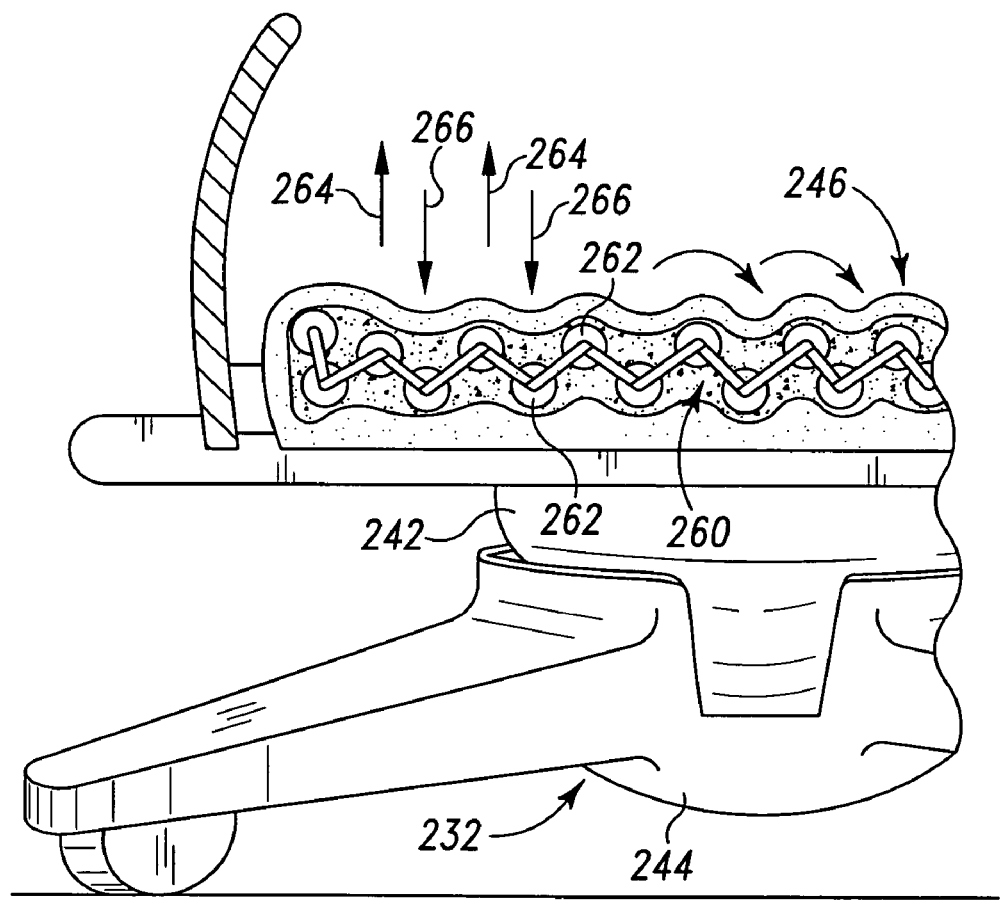
FIG. 25 is a partial sectional view taken along line 25-25 of FIG. 20, illustrating a massaging mattress supported on the bed.

As illustrated in FIG. 25, a massage mechanism 260 including a plurality of rollers 262 is located within the patient support surface 246. The rollers 262 illustratively move up and down in the direction of arrows 264 and 266 to provide therapy to the patient. Movement of rollers 262 is controlled by a mechanical linkage or pneumatic bladders within the mattress 246.

Yet another embodiment of the present invention includes a pulmonary therapy system 270 as illustrated in FIGS. 26-33. The system 270 includes a chest binding apparel apparatus 280 to apply pressure to the chest of the patient 23.

Figure 28:
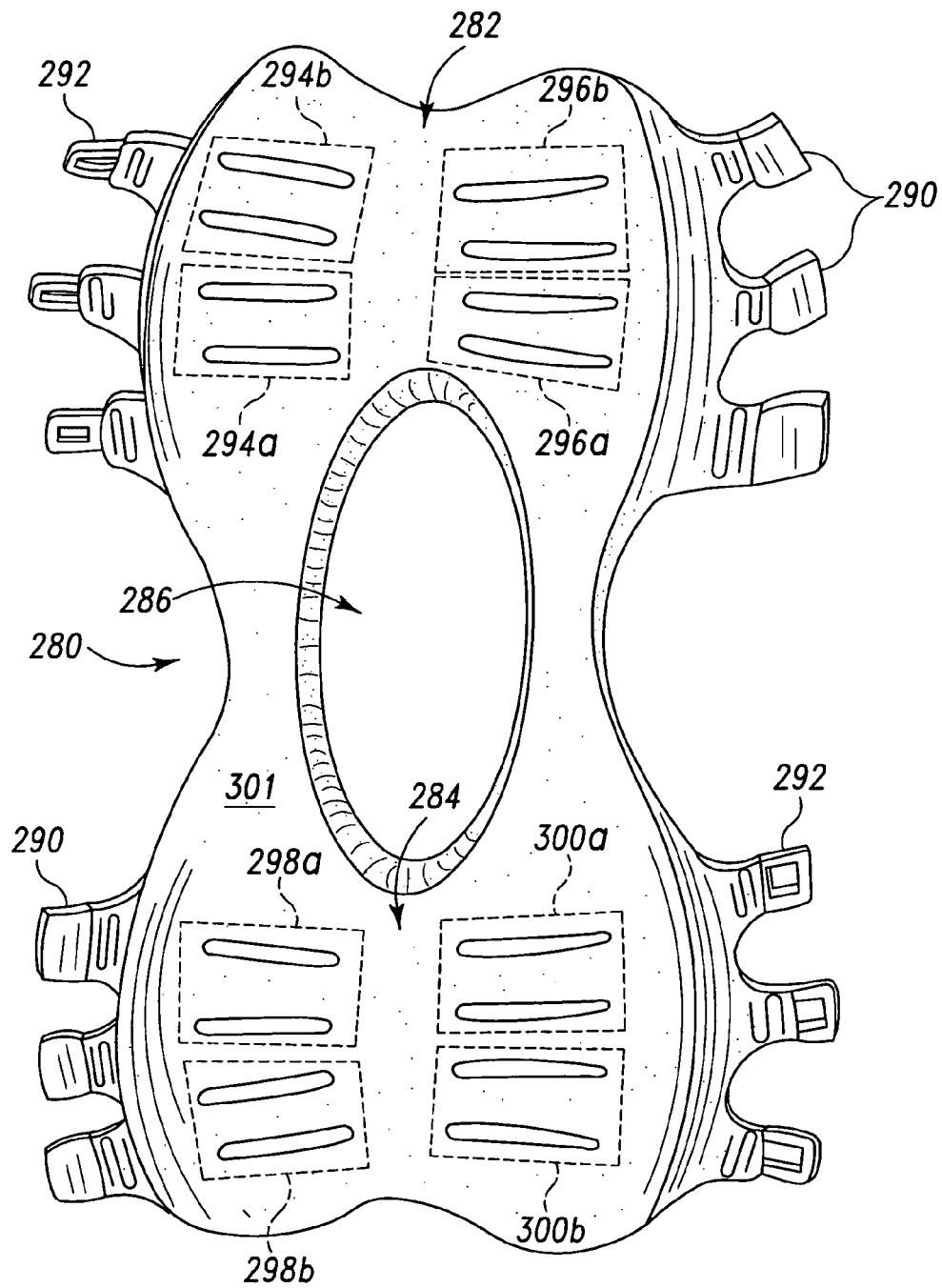
FIG. 28 is a bottom plan view of the vest of FIG. 27.
Figure 29:
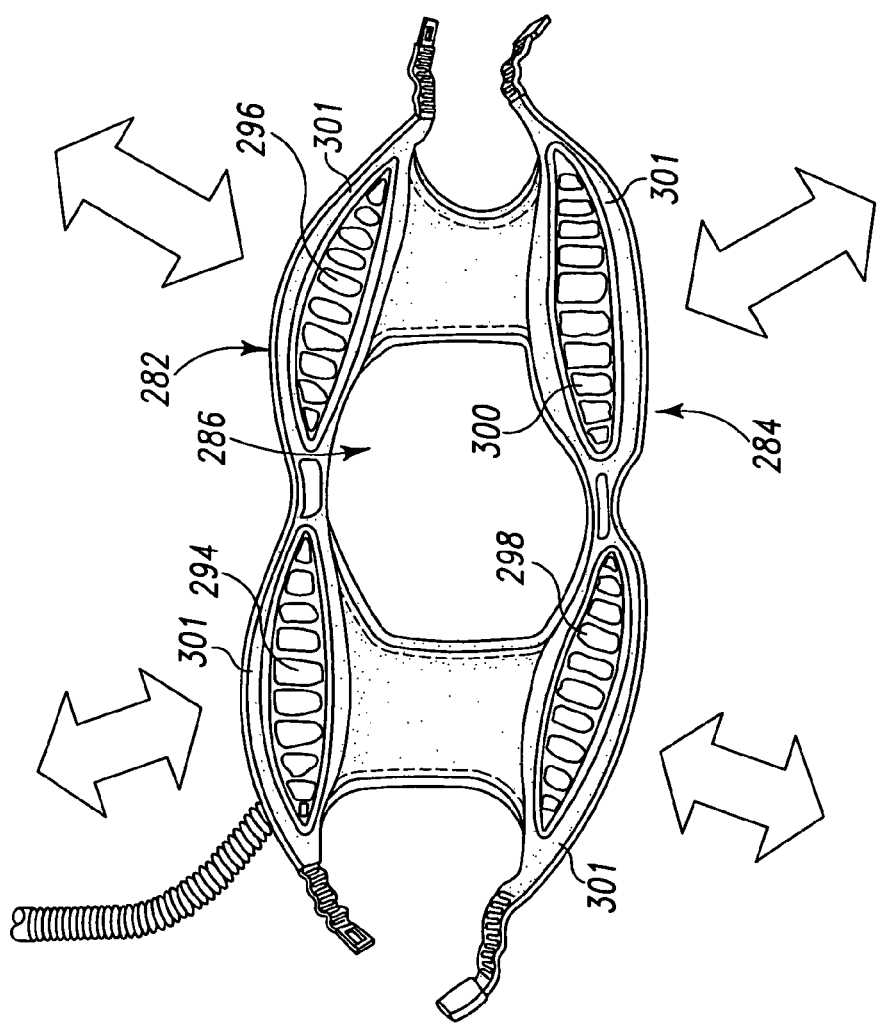
FIG. 29 is a sectional view taken along line 29-29 through the vest of FIG. 26.

The chest binding apparel apparatus 280 is illustratively a vest having a front portion 282, a rear portion 284, and a head receiving aperture 286. An air connection to apparatus 280 is provided by bladder supply line 288. Mating fasteners 290 and 292 are coupled to the front and back portions 282 and 284, respectively, as illustrated in FIG. 28. A plurality of air bladders 294, 296, 298, and 300 are supported by a rigid shell 301 of the apparatus 280. Illustratively, bladders 294 and 296 are located within the left and right front portion 282, respectively, and bladders 298 and 300 are located within the left and right rear portion 284, respectively.

Figure 26:
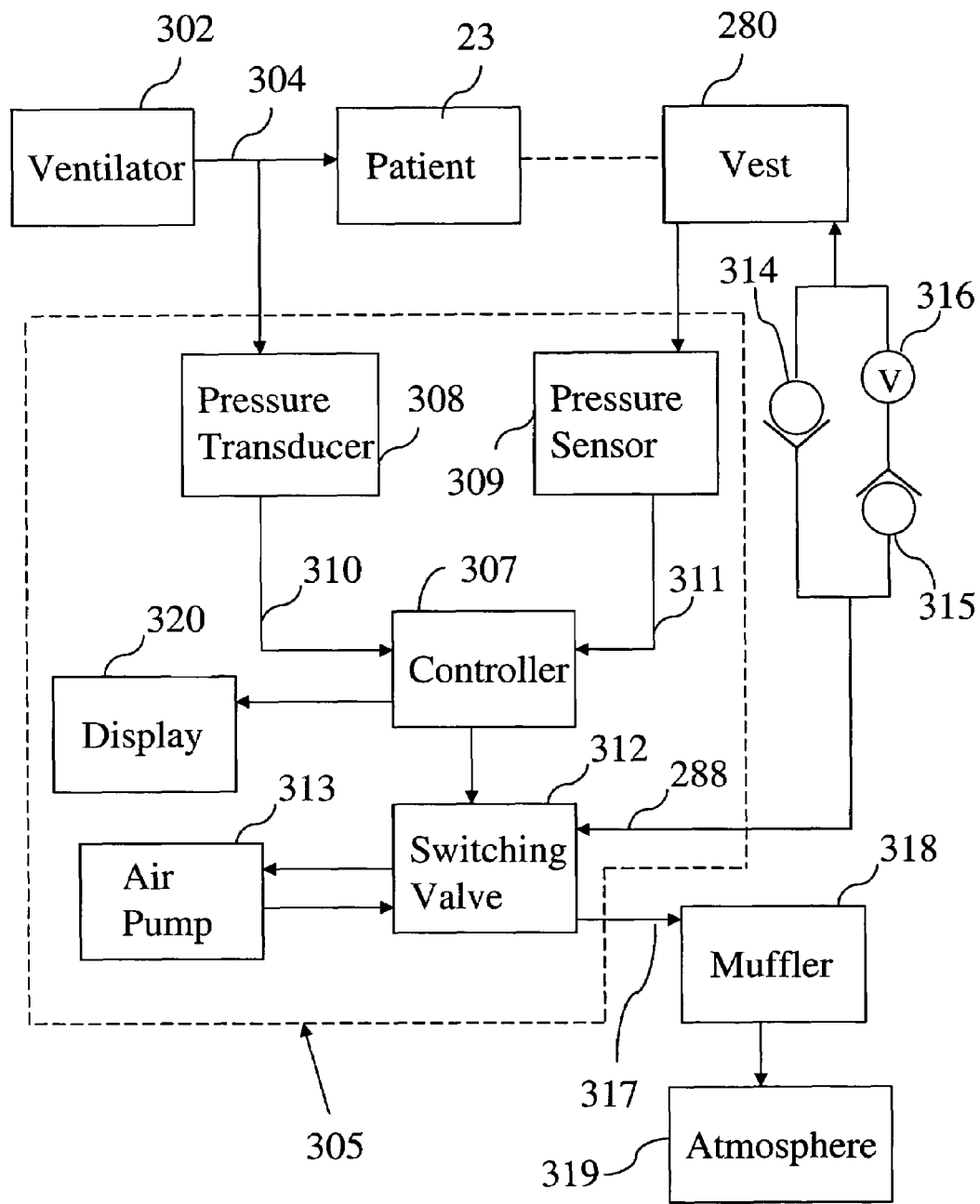
FIG. 26 is a block diagram illustrating a pulmonary therapy system of the present invention.
Figure 27:
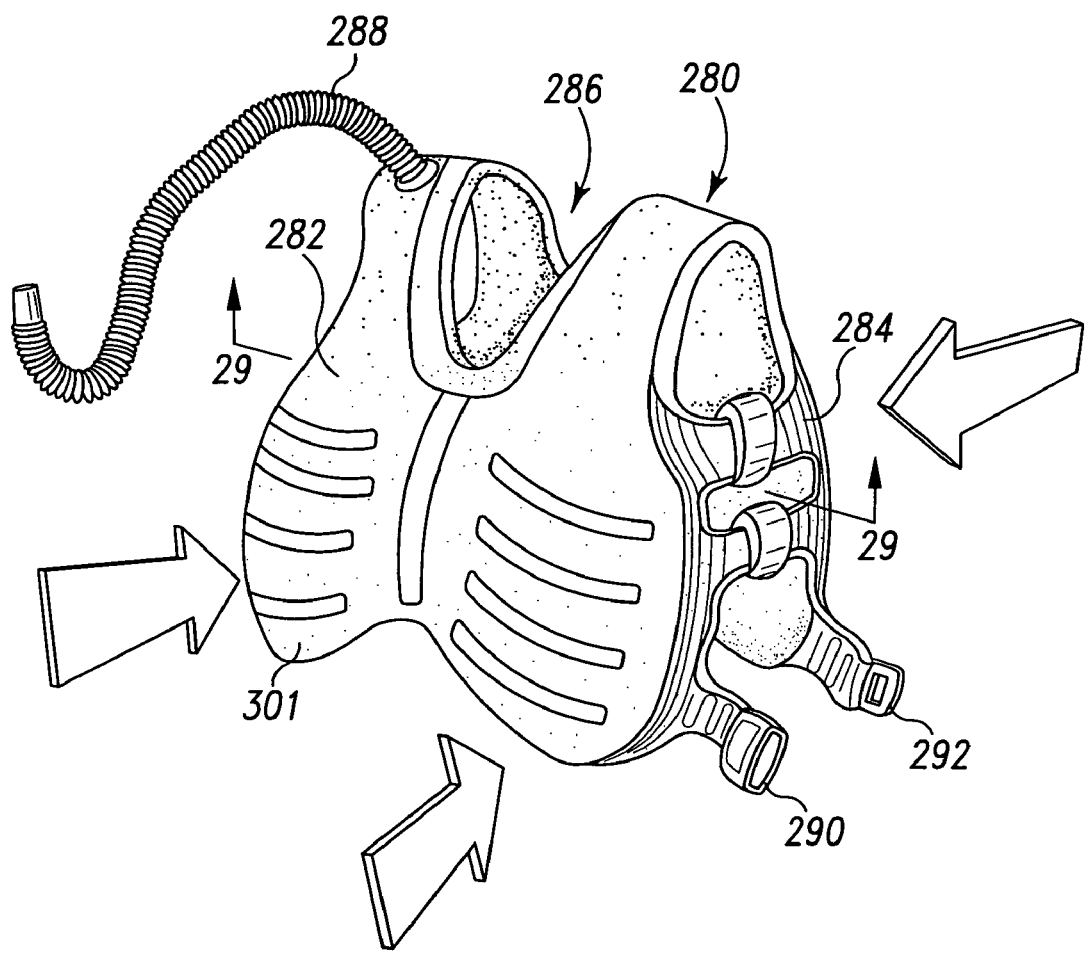
FIG. 27 is a perspective view illustrating a vest for providing pulmonary therapy, including chest binding, percussion and vibration therapy on a patient.
Figure 30:
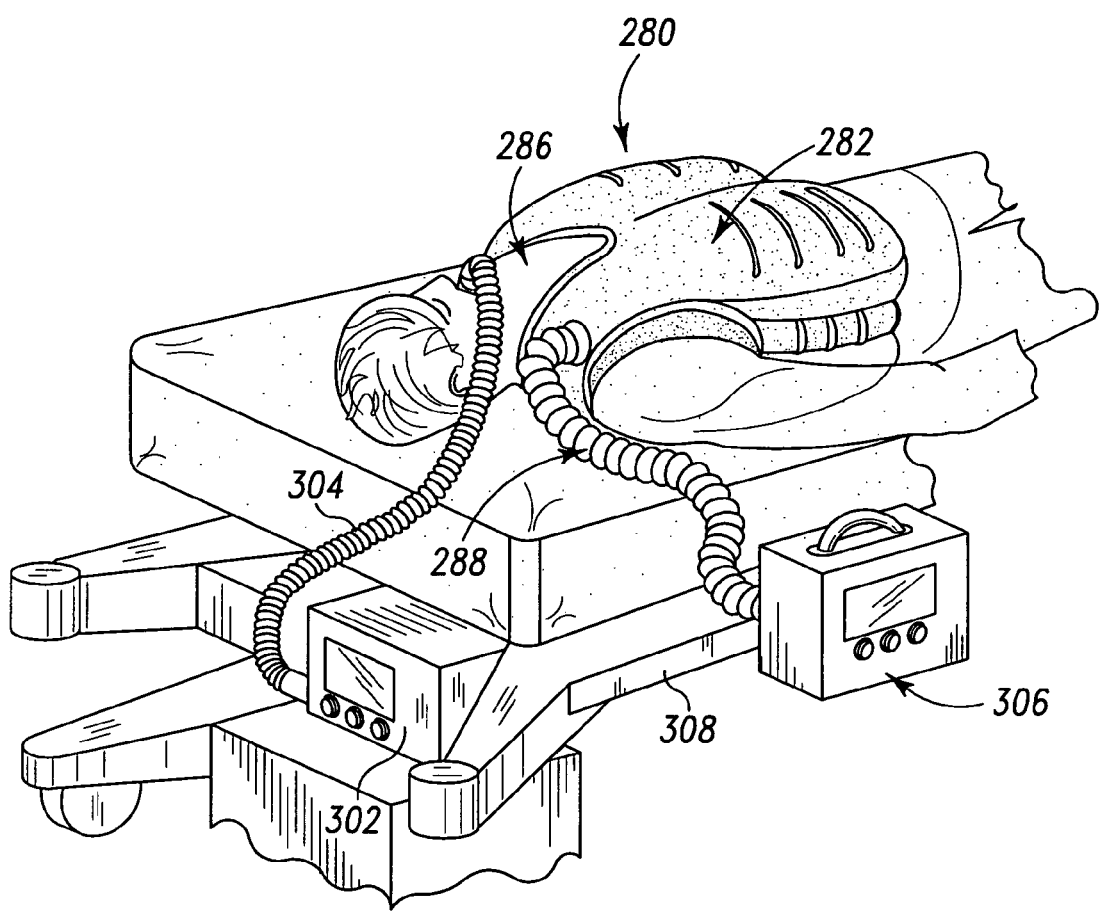
FIG. 30 illustrates the vest of FIG. 27 on a patient located on a bed.
Figure 31:
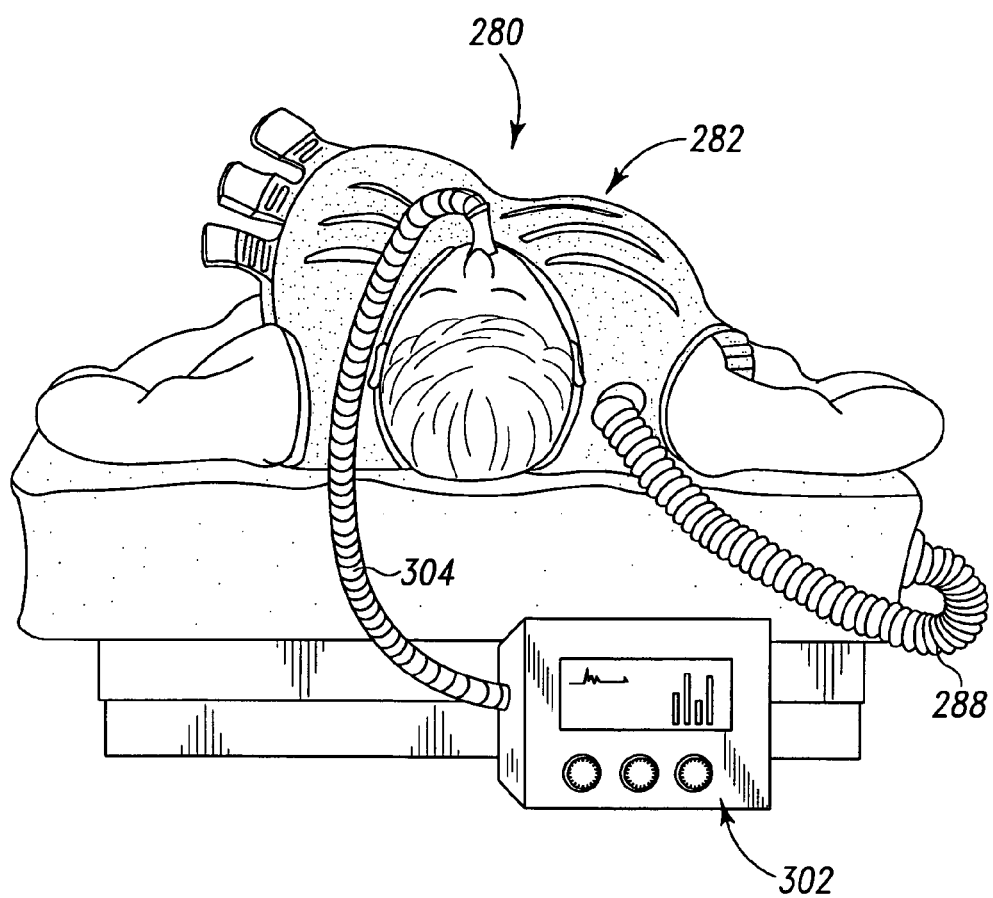
FIG. 31 is an end view illustrating the vest of FIG. 30 on the patient with at least one of the air bladders within the vest inflated to provide therapy to the patient.

Each of the bladders 294, 296, 298, and 300 illustratively includes one or more separately inflatable zones. With reference to FIG. 28, each bladder 294, 296, 298, and 300 includes separate upper and lower zones identified as 294a, 294b, 296a, 296b, 298a, 298b, and 300a, 300b, respectively. Air is selectively supplied to bladders 294, 296, 298, and 300 to perform chest binding when a ventilator 302 is coupled to the patient 23 by a ventilator tube 304 as shown in FIGS. 26 and 30. In addition, bladders 294, 296, 298, and 300 perform percussion/vibration therapy. The air supply and control module 305 is illustratively mounted to a bed frame 306 to selectively supply air to the various zones within bladders 294, 296, 298, and 300 to perform the therapy on the patient 23.

The air supply and control module 305 is further illustrated schematically in FIG. 26. The air supply and control module 305 includes a controller 307 in communication with a ventilator pressure sensor 308 and an apparel pressure sensor 309. The ventilator pressure sensor 308 may comprise a conventional pressure transducer in communication with the ventilator tube 304 for sensing a pressure of air supplied to the patient 23 and for generating a ventilator pressure signal 310 indicative thereof. The apparel pressure sensor 309 is coupled to the vest 280 for sensing a pressure applied by the vest 280 to the chest of the patient 23 and generating an apparel pressure sensor 311 indicative thereof. The pressure sensor 309 may comprise a pressure sensing fabric disposed in between the vest 280 and the chest of the patient 23. A switching valve 312 is coupled to an external air supply, such as air pump 313, for alternating between a first mode of operation wherein air is supplied to the air bladders 294, 296, 298 and 300, and a second mode of operation where air is evacuated from the air bladders 294, 296, 298 and 300. A loop is formed within the bladder supply line 288, and includes first and second check valves 314 and 315, respectively. A needle valve 316 is provided in series with the second check valve 315 and provides for control of the amount of air evacuated during the second mode of operation. An exhaust line 317 is in fluid communication with the switching valve 312 and exhausts air through a muffler 318 and into the atmosphere 319. A conventional display 320, such as a liquid crystal display, is provided in communication with the controller 307 for displaying information detected by the ventilator pressure sensor 308 and the apparel pressure sensor 309.

In operation, the ventilator 302 provides air to the patient through the ventilator line 304. The pressure transducer 308 senses when air is supplied to the patient 23 and provides the ventilator pressure signal 310 to the controller 307. When the controller 307 determines that air is being supplied to the patient 23, it instructs the switching valve 312 to operate in a first mode wherein air is supplied to line 288 passing through check valve 314 and subsequently to the vest 280. In the preferred embodiment, the upper bladders 294a, 296a, 298a, and 300a will be only activated or inflated during periodic cycles. By only applying pressure to the upper portion of the chest of the patient 23, air is forced downwardly into the lower portion of the lungs, thereby improving oxygenation. In intervening cycles, all of the bladders 294a, 294b, 296a, 296b, 298a, 298b, 300a and 300b may be activated to provide more uniform pressure to both upper and lower portions of the lungs. Through such cycling, it is believed that more effective oxygenation of the patient will result.

When the pressure transducer 308 determines that air is not being supplied to the patient 23, then the pressure signal 310 indicates such to the controller 307. The controller 307, in turn, instructs the switching valve 312 to operate in a second mode wherein air is evacuated from the bladders 294, 296, 298 and 300 by operation of the pump 313. The air then passes through the exhaust line 317 and muffler 318 to atmosphere 319.

Throughout operation of the system 270, the pressure sensor 309 will provide an indication of whether effective pressure is being applied by the vest 280 to the lungs of the patient 23. Moreover, the signal 311 provided to the controller 307 may result in instructions provided on display 320. For example, if the vest requires tightening on the patient 23, this may be indicated by the display 320.

Figure 32:
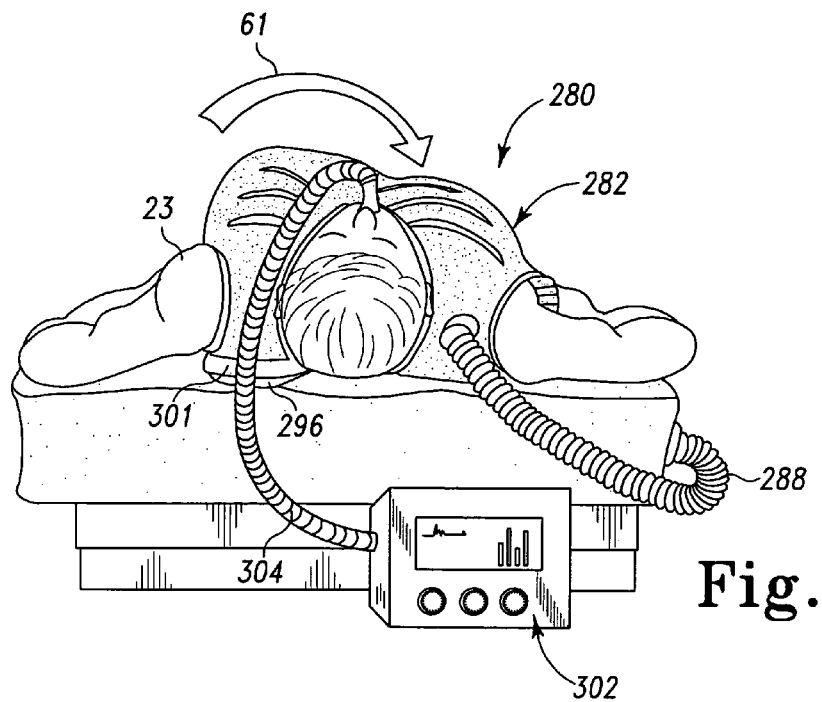
FIG. 32 is an end view illustrating the vest of FIG. 30 on the patient with the right rear air bladder inflated to provide continuous lateral rotational therapy to the patient.
Figure 33:
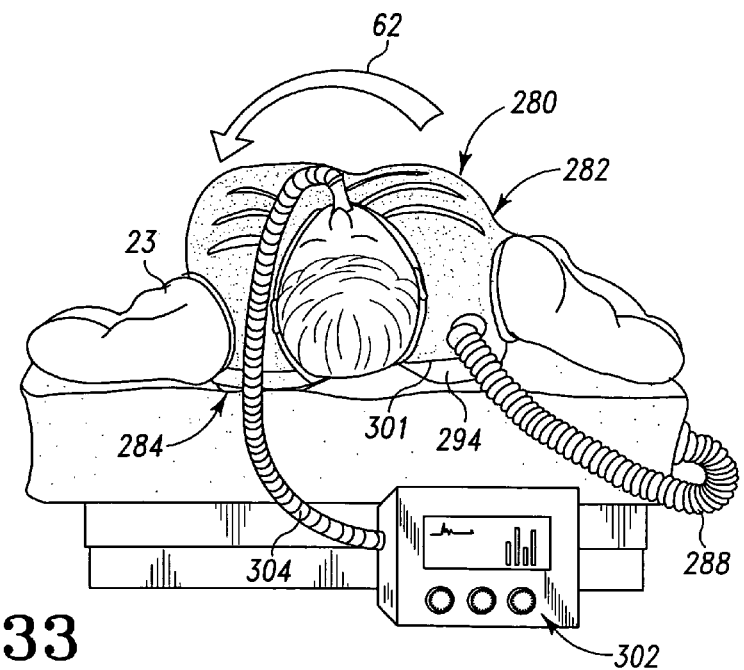
FIG. 33 is an end view illustrating the vest of FIG. 30 on the patient with the left rear air bladder inflated to provide continuous lateral rotational therapy to the patient.

Referring now to FIGS. 32 and 33, the chest binding apparel apparatus 280 may be utilized to perform continuous lateral rotational therapy (CLRT) on the patient 23. More particularly, with reference to FIG. 32, deflation of the left rear bladder 294 and inflation of the right rear bladder 296, supported outside of the rigid shell 301, results in rotational movement of the patient 23 in the direction of arrow 61. Deflation of the right rear bladder 296 and inflation of the left rear bladder 294, again supported outside of the rigid shell 301, results in rotation of the patient 23 in the direction of arrow 62 which is opposite the direction of arrow 61 of FIG. 32. Alternating inflation and correspondence deflation of the bladders 294 and 296 results in oscillating rotational movement of the chest of the patient 23. This continuous lateral rotational therapy provides the benefit of moving liquids contained within the lungs of the patient 23.

Figure 34:
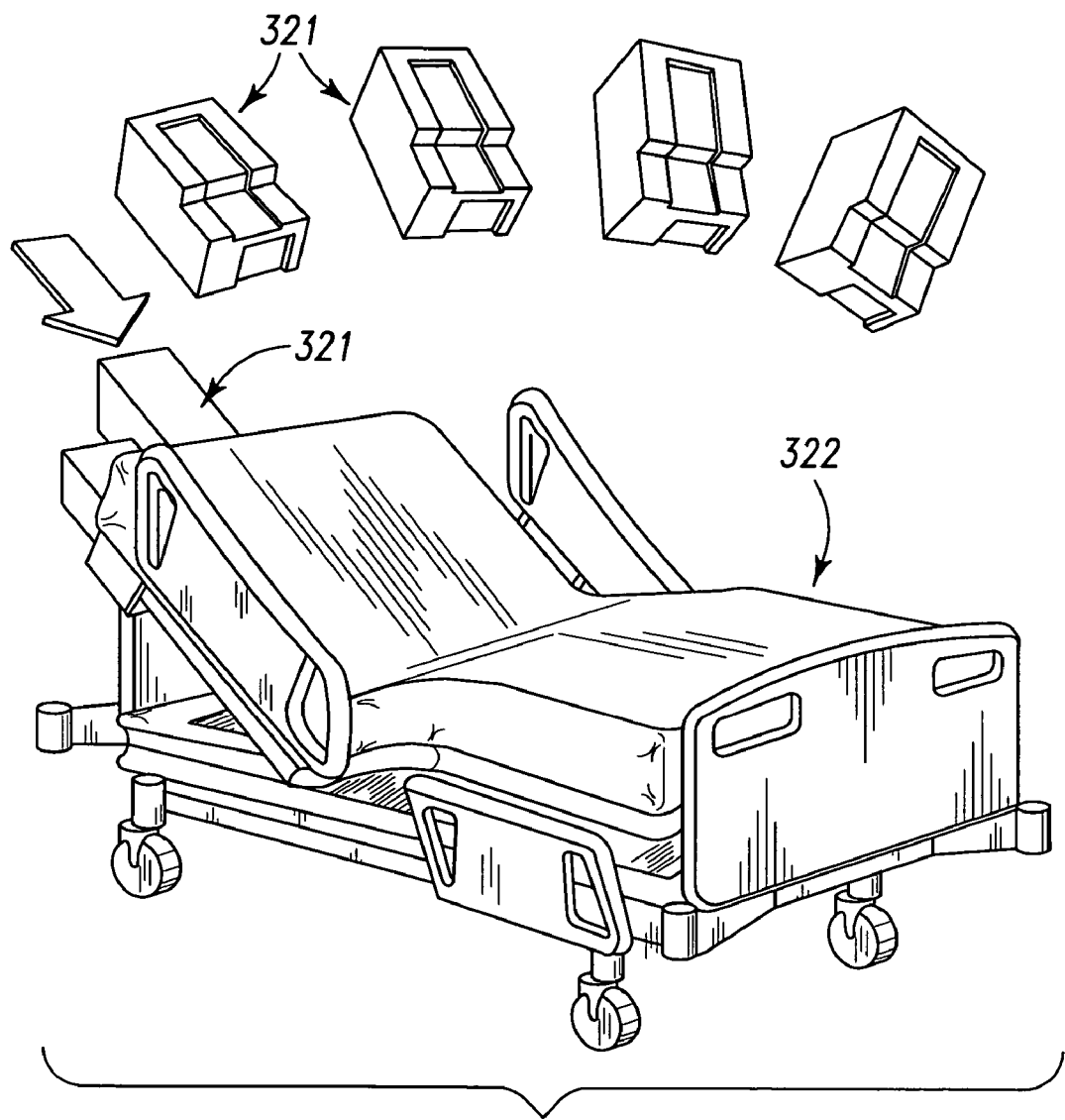
FIG. 34 is a perspective view illustrating a plurality of control modules configured to be coupled to a bed to control the various therapies of the present invention.
Figure 35:
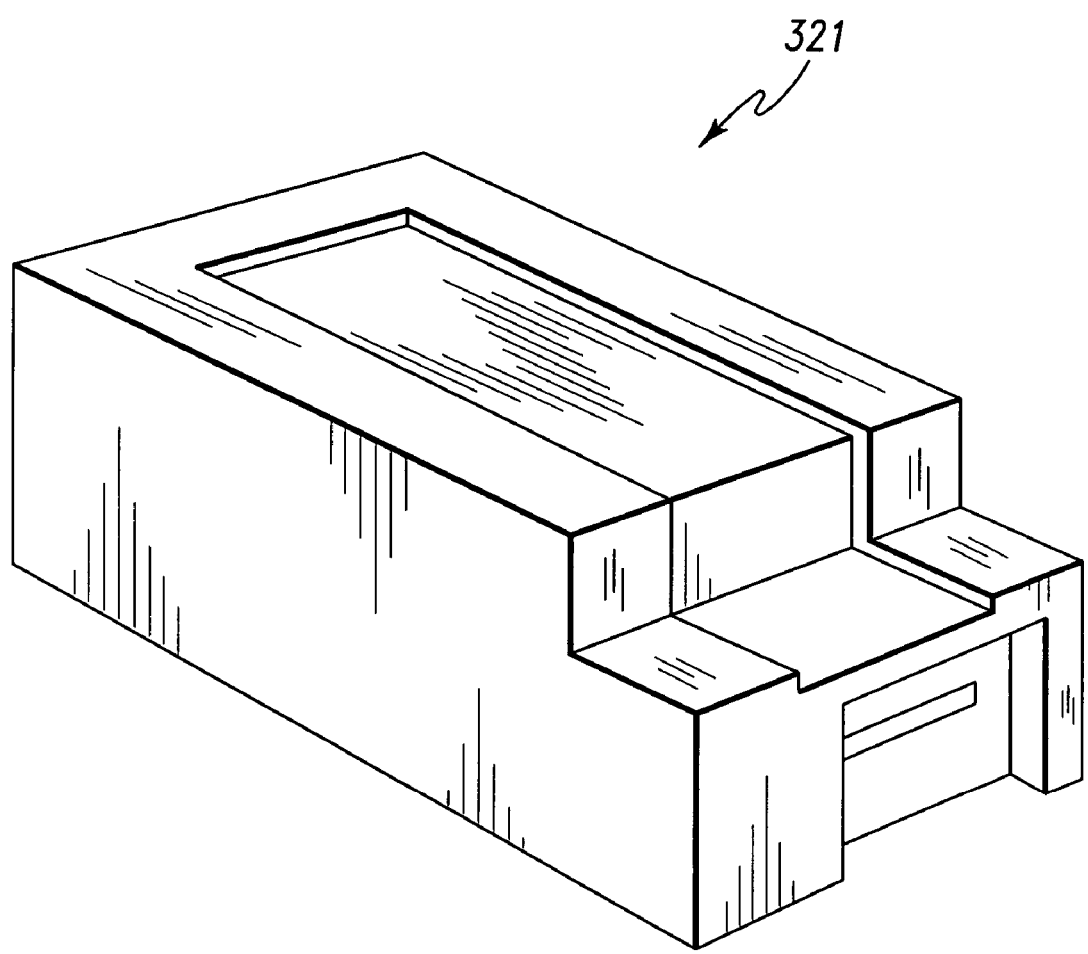
FIG. 35 is a perspective view illustrating one of the control modules of FIG. 34.
Figure 36:
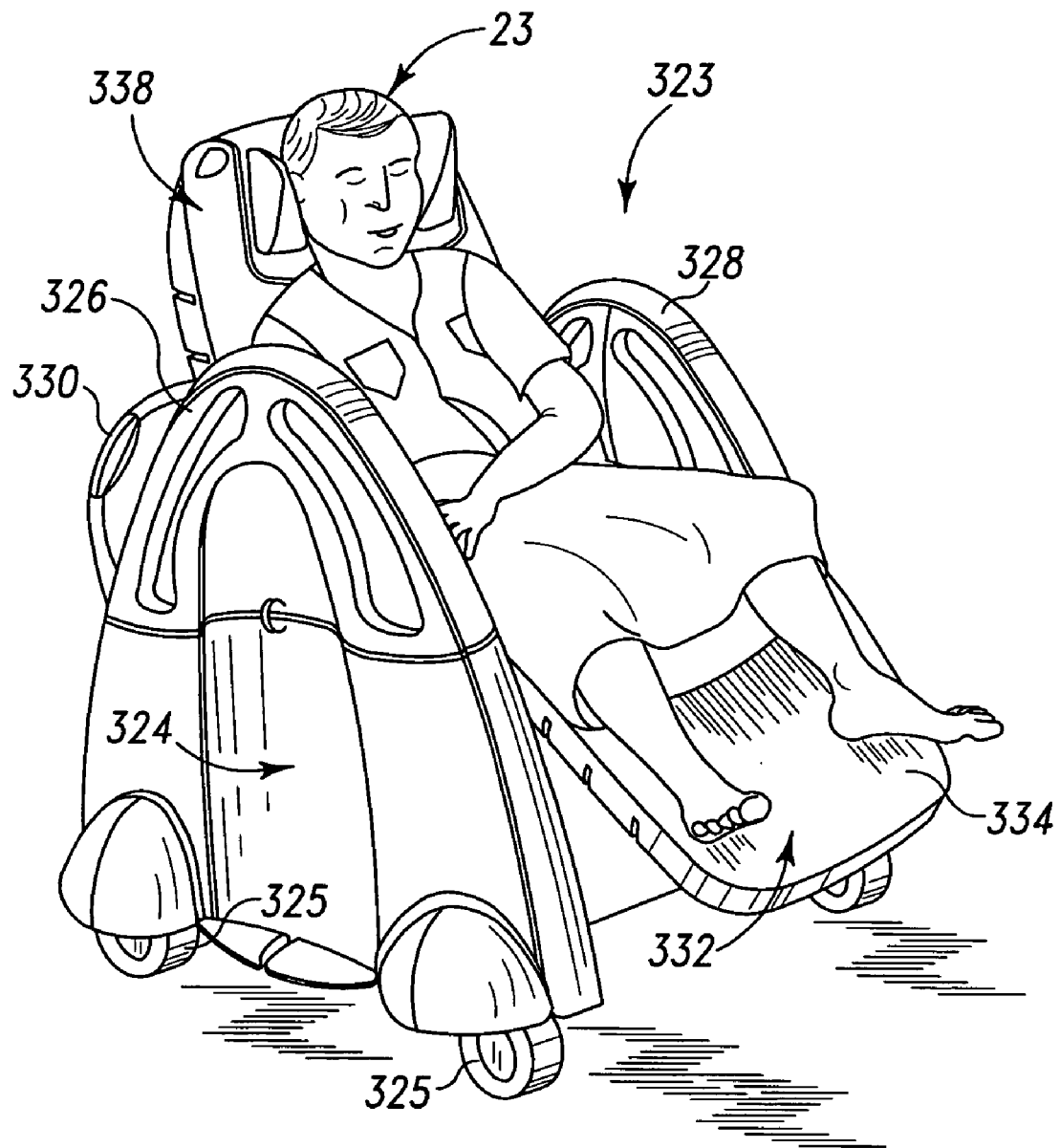
FIG. 36 is a perspective view of a longitudinal rotation platform according to another embodiment of the present invention which is movable between a chair position and a bed position.
Figure 37:
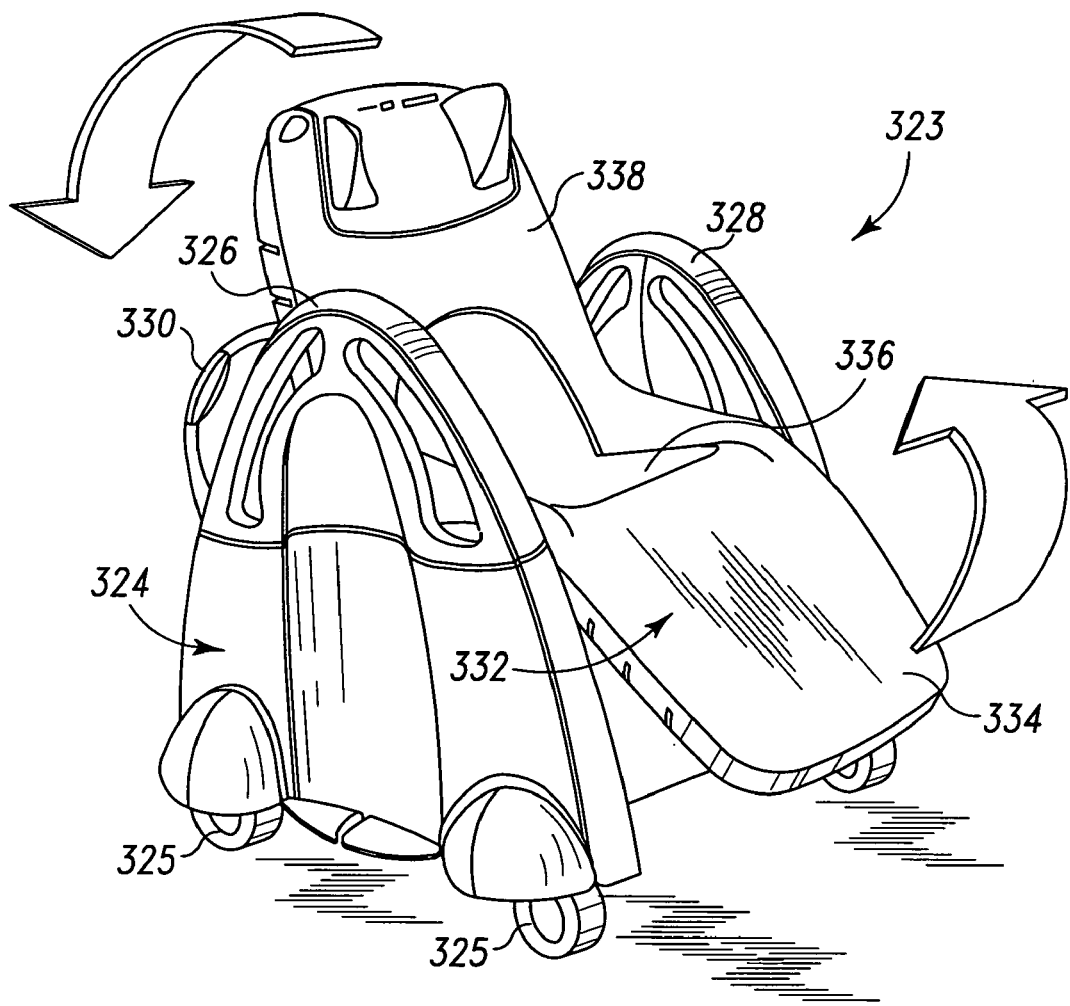
FIG. 37 is a perspective view of the longitudinal rotation platform of FIG. 36, illustrating movement of a head support section and a leg support section.

It is understood that the various embodiments of the present invention may be controlled with control modules 321 as shown in FIGS. 34 and 35. Modules 321 are designed to be coupled to a bed 322. Illustratively, bed 322 includes an electrical communication network and an air supply. When the modules 321 are coupled to the bed 322, a processor within the modules 321 is coupled to the electrical communication network of the bed to receive therapy instructions from a user input. The modules 321 then control flow of air from the air supply to the various air zones to provide the therapy. Such modules are disclosed in U.S. Pat. Nos. 5,630,238 and 6,047,424, which are expressly incorporated herein by reference.

Yet another embodiment of the of the present invention is illustrated in FIGS. 36-44. In this embodiment, a longitudinal rotation platform apparatus 323 includes the base 324 having a plurality of castors 325. Base 324 includes opposing side members 326 and 328. Push handles 330 are also coupled to the base 324. An articulating patient support surface 332 is also coupled to the base 324. Suitable drive mechanisms (not shown) are provided to articulate the patient support surface from a chair position shown in FIGS. 36 and 37 to a substantially flat bed position shown in FIGS. 40 and 43.

Natural upright lung positioning facilitates improved ventilation and lung drainage. The present invention provides proper patient location through range of therapy, a flexible range of therapy (Trendelenburg to chair egress), potential release of intrinsic Nitric Oxide, reduced floor space usage, and psychological benefit of less "bed-like" appearance.

Illustratively, the patient support surface 332 includes a leg section 334, a seat section 336, and a back section 338. Leg section 334 and back section 338 are pivotable upwardly and downwardly relative to seat section 336 to move the support surface 332 intermediate the chair position to the bed position.

Figure 38:
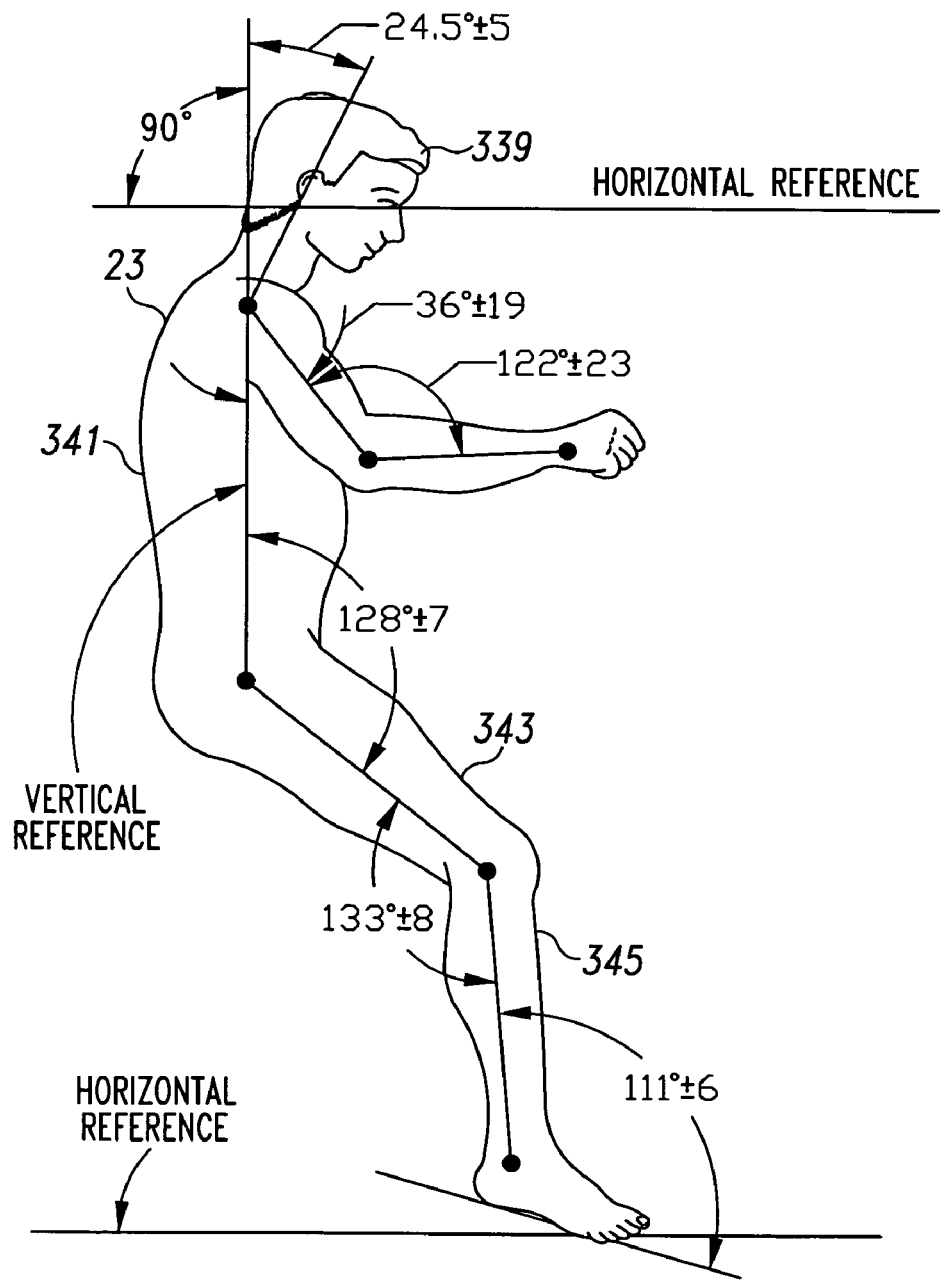
FIG. 38 is a diagrammatical view illustrating the body of a patient positioned in a weightless, neutral body position.
Figure 39:
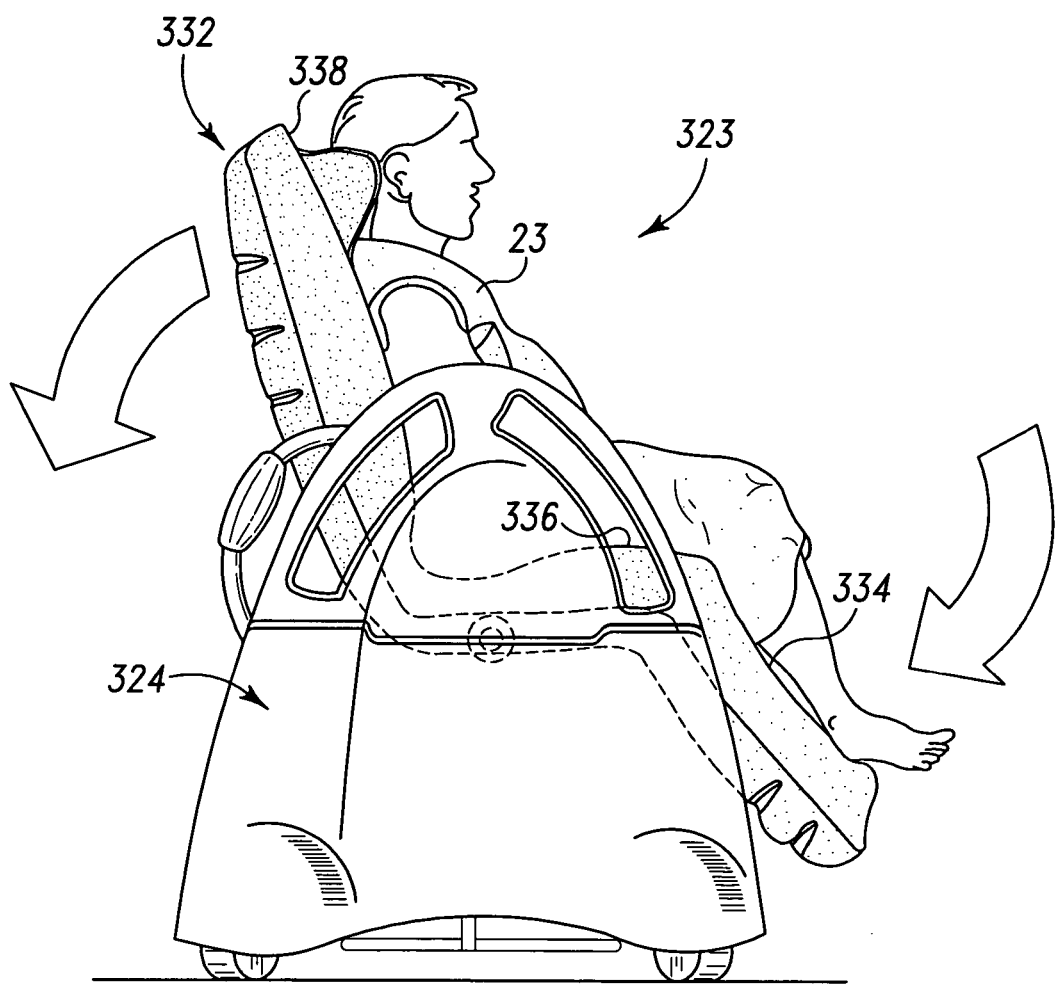
FIG. 39 is a side elevational view of the longitudinal rotation platform of FIG. 36.

Referring now to FIG. 38, the body of a patient 23 in a weightless, neutral body or zero-gravity position is illustrated. Such weightless neutral body position is well-known in the art and is a position the body of a patient 23 would assume in a weightless environment. As illustrated in FIG. 38, in the weightless neutral body position, the head 339 of the patient 23 is positioned at approximately 24.5° from the back 341, while the back 341 is positioned at approximately 128° relative to the thighs 343. Finally, the thighs 343 are positioned at approximately 133° relative to the legs 345. It is believed that not only does the weightless neutral body position provide added comfort for the patient 23, but also improves oxygenation to the patient 23.

Figure 40:
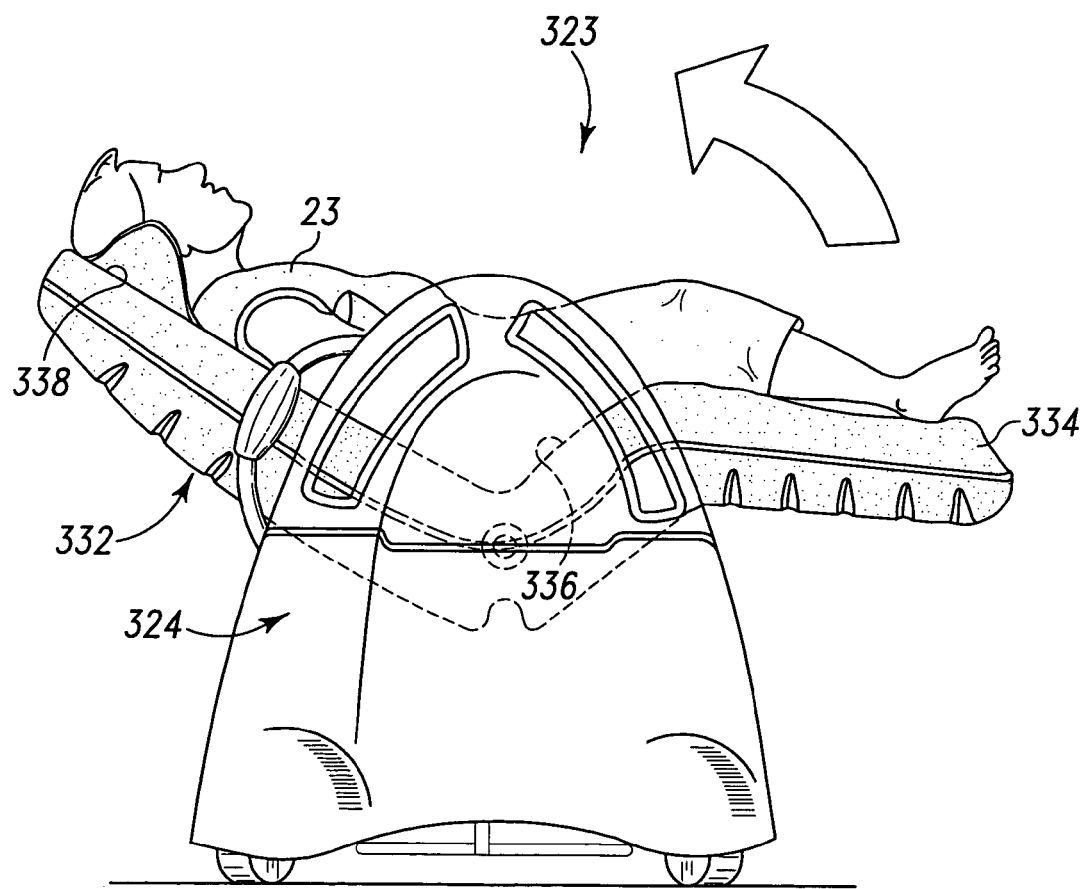
FIG. 40 is a side elevational view similar to FIG. 39, illustrating movement of the head section and leg section to move the patient to a reclined position.
Figure 41:
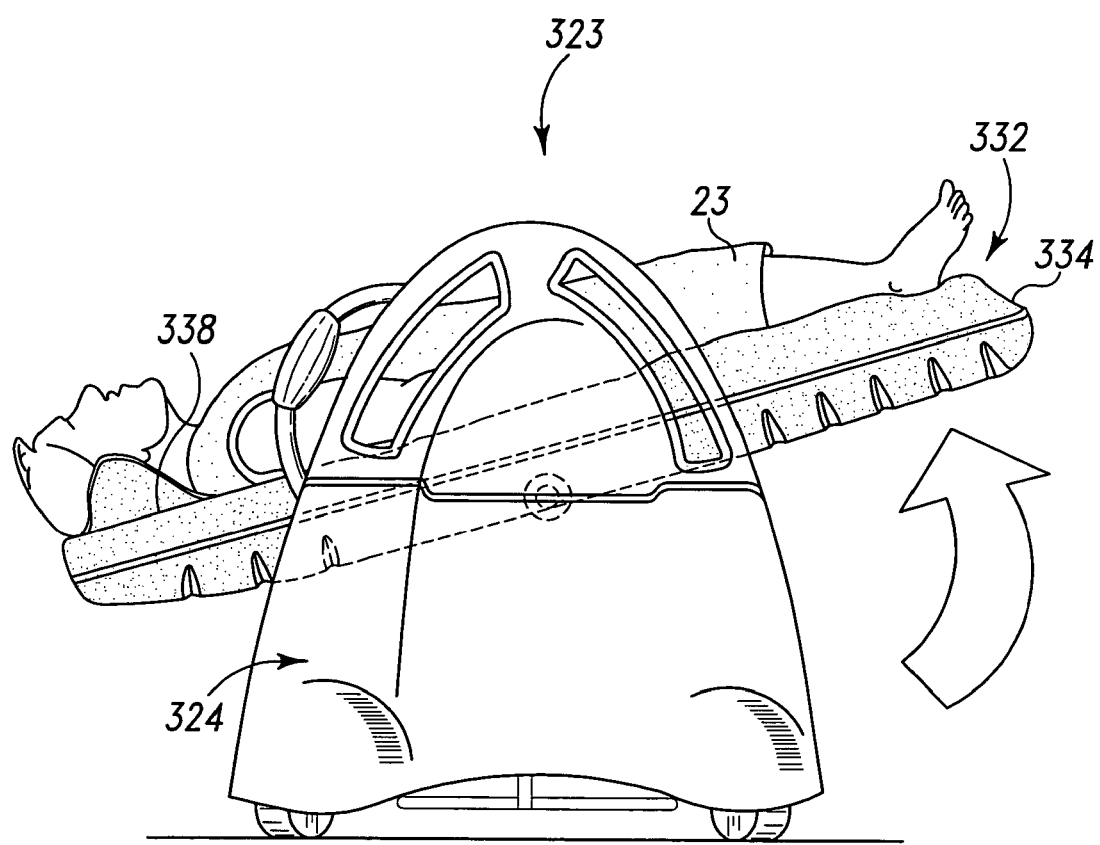
FIG. 41 is a side elevational view similar to FIG. 39, illustrating movement of the patient support surface to a Trendelenburg position.

FIG. 40 illustrates the support surface in an intermediate reclined position. FIG. 41 illustrates the support surface 332 in a flat bed position and pivoted about transverse axis 340 to a Trendelenburg position.

Figure 42:
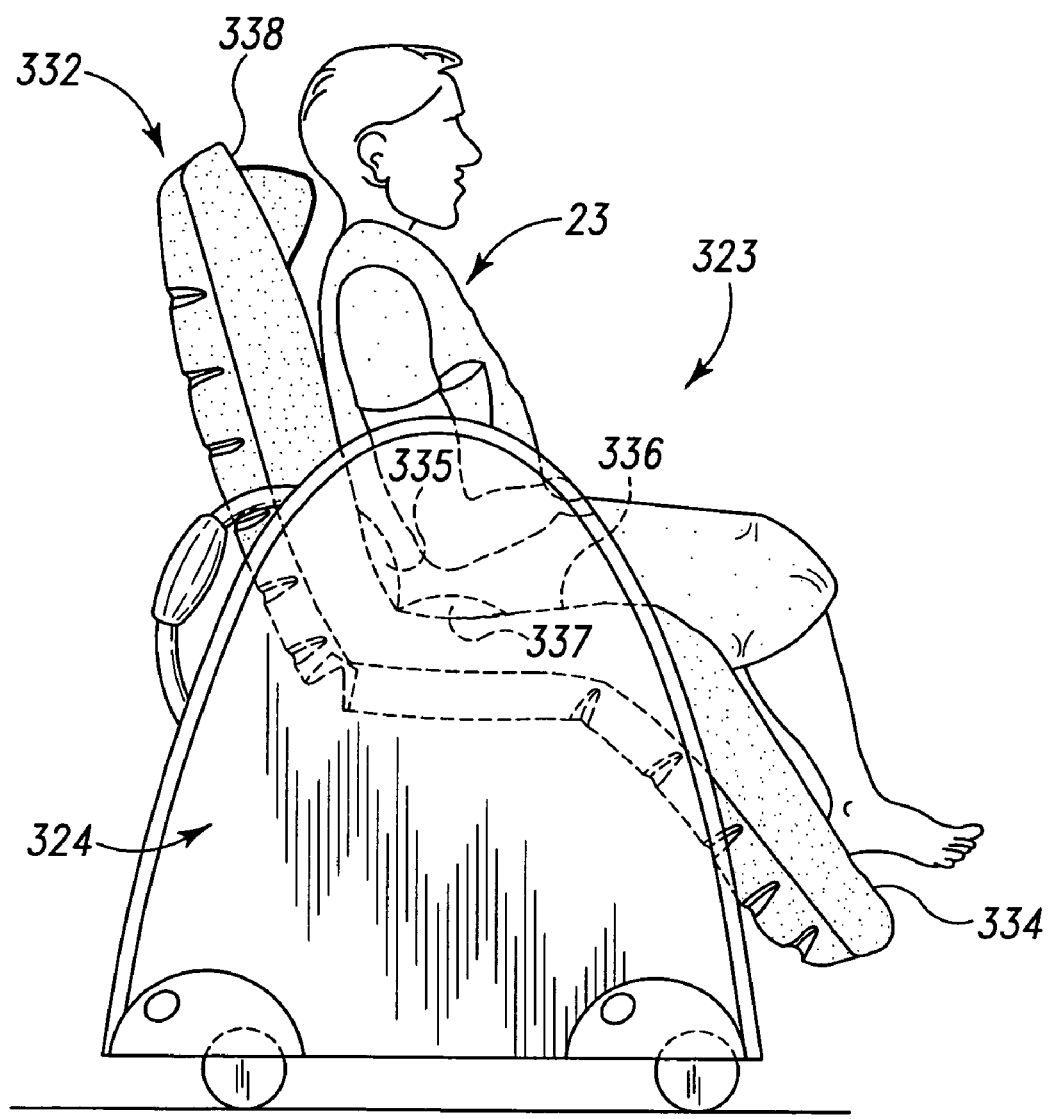
FIG. 42 is a side elevational view similar to FIG. 39, illustrating additional details of a patient support surface including bladders for the locating and retaining the patient on the support surface.
Figure 43:
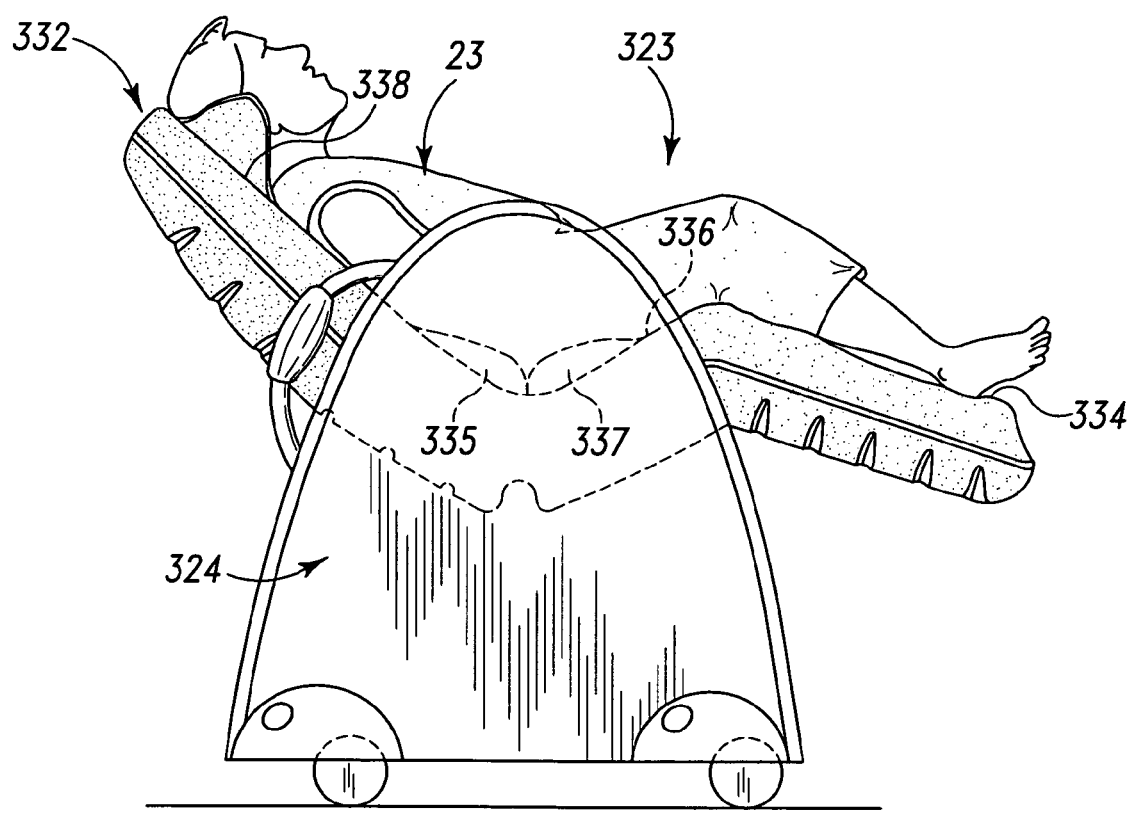
FIG. 43 is a side elevational view similar to FIG. 39, illustrating the patient support surface in a reclined position.
Figure 44:
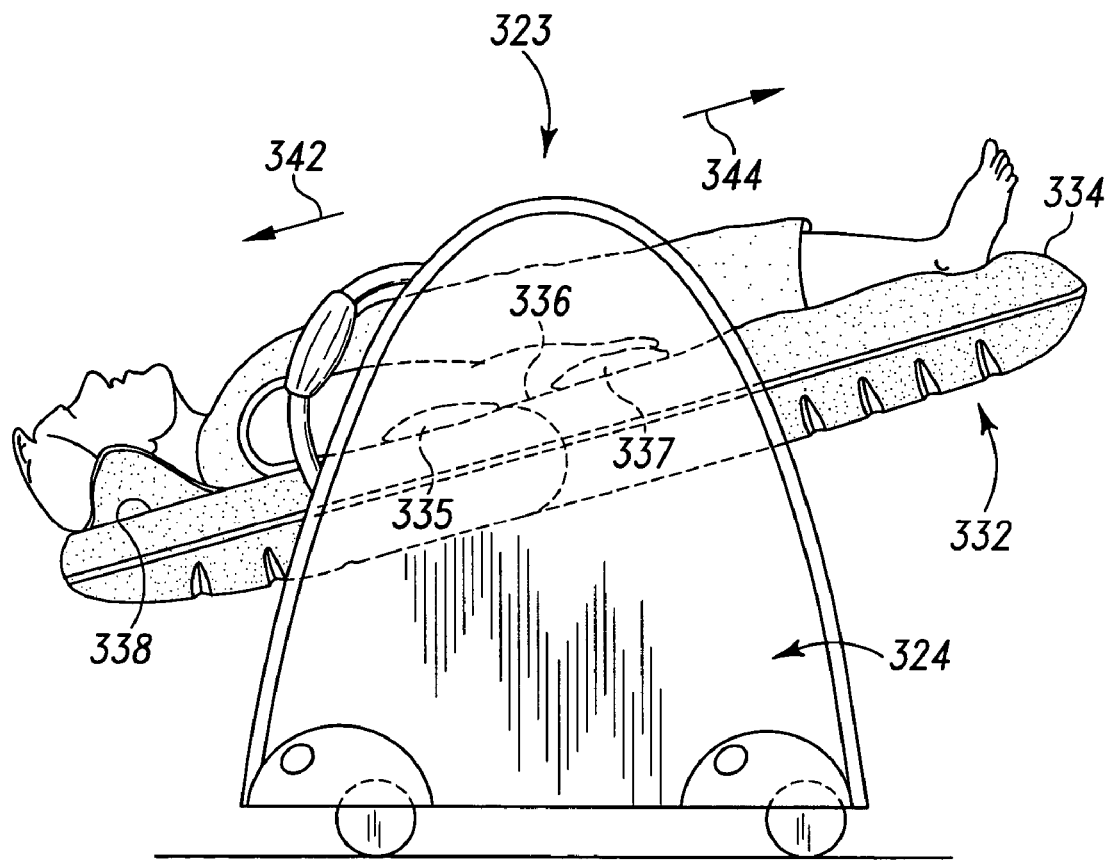
FIG. 44 is a side elevational view similar to FIG. 39, illustrating the patient retention bladders when the patient support surface is in the Trendelenburg position.

Illustratively, support surface 332 includes body locating and retention bladders 335 and 337 located adjacent to patient's lower back 341 and seat or thighs 343. Bladders 335 and 337 help locate the patient 23 on the chair as illustrated in FIG. 42. Bladder 335 helps prevent movement of the patient 23 toward a head end of the support surface 332 in the direction of arrow 342 when the support surface 332 is in the Trendelenburg position as shown and best illustrated in FIG. 44. Bladder 337 helps prevent movement of the patient toward the foot-end of the patient support surface 332 in the direction of arrow 344 when the support surface 334 is in the chair position or the reverse Trendelenburg position.

Figure 45:
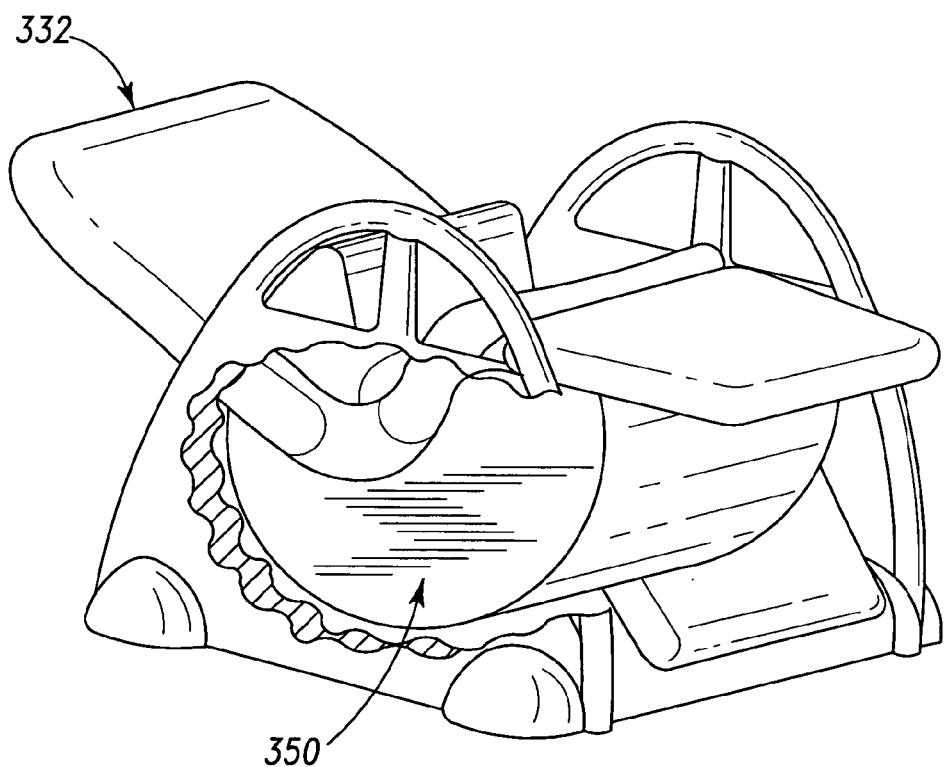
FIG. 45 is a perspective view, in partial schematic, of a drive mechanism for pivoting the patient support surface of FIG. 39.
Figure 46:
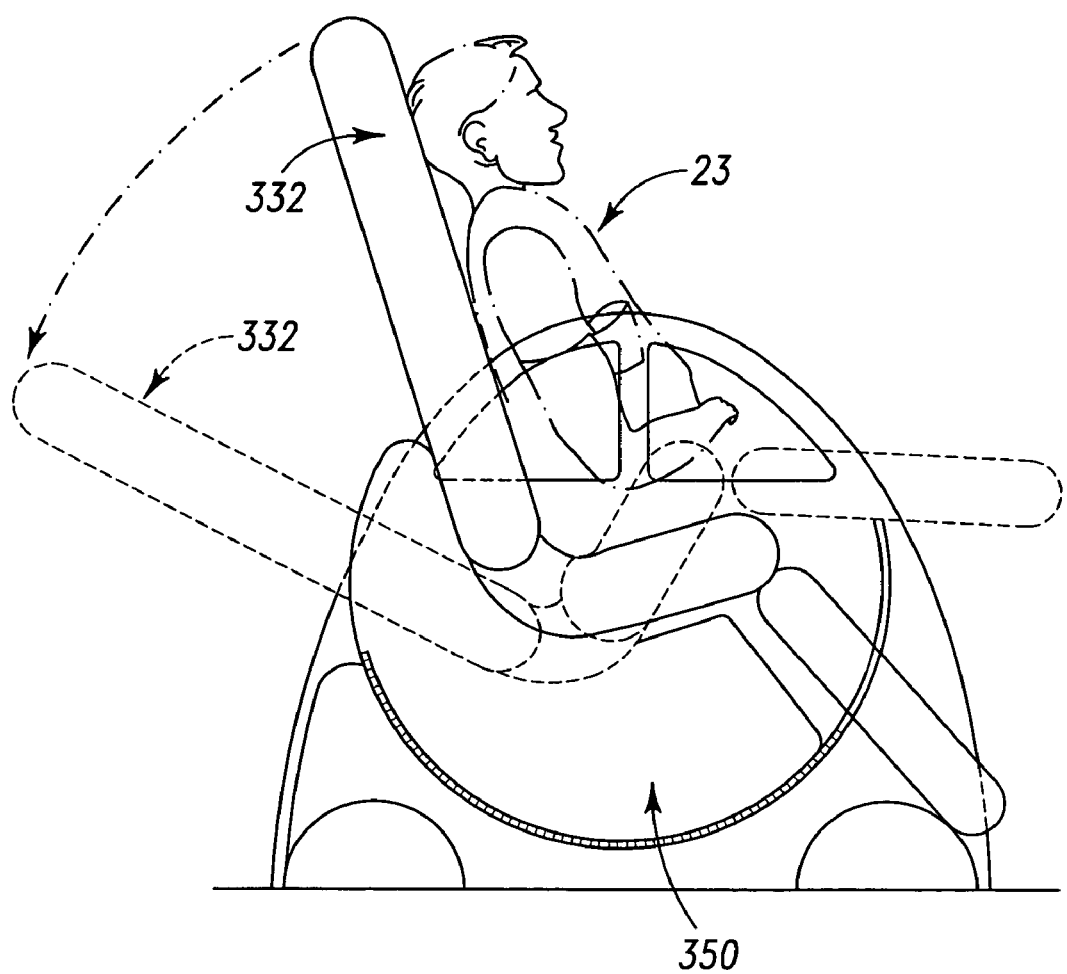
FIG. 46 is a side elevational view, in partial schematic, of the drive mechanism of FIG. 45.
Figure 47:
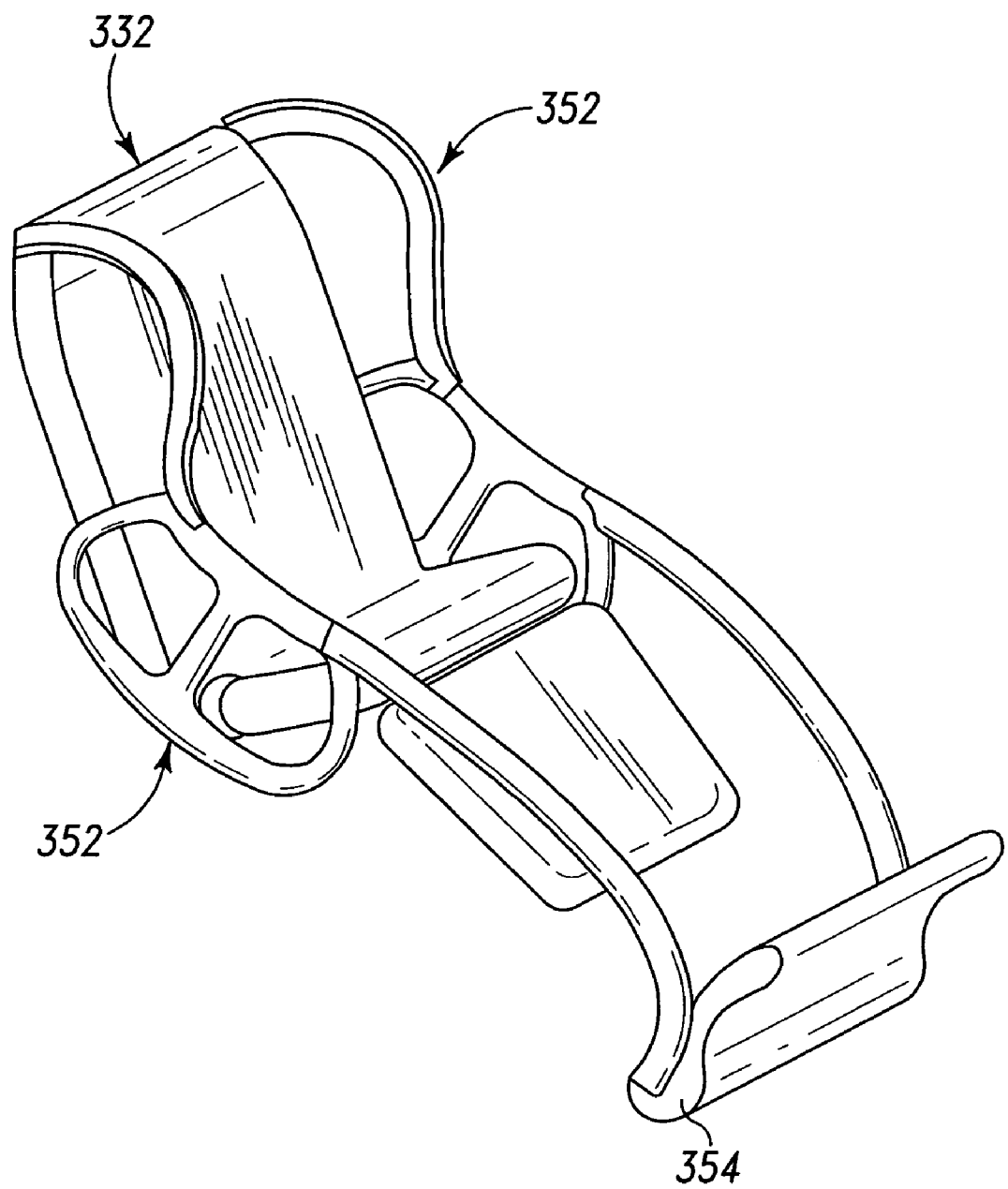
FIG. 47 is a perspective view of components positioned adjacent the patient support surface of FIG. 39.

FIGS. 45 and 46 illustrate a drive mechanism 350 for pivoting the support surface 332 about a transverse pivot axis. The drive mechanism 350 may be similar to the mover disclosed in U.S. Pat. No. 6,609,260 which is assigned to the assignee of the present invention and is incorporated herein by reference. FIG. 47 illustrates siderails 352 and a foot prop 354 located adjacent the support surface 332.

Figure 48:
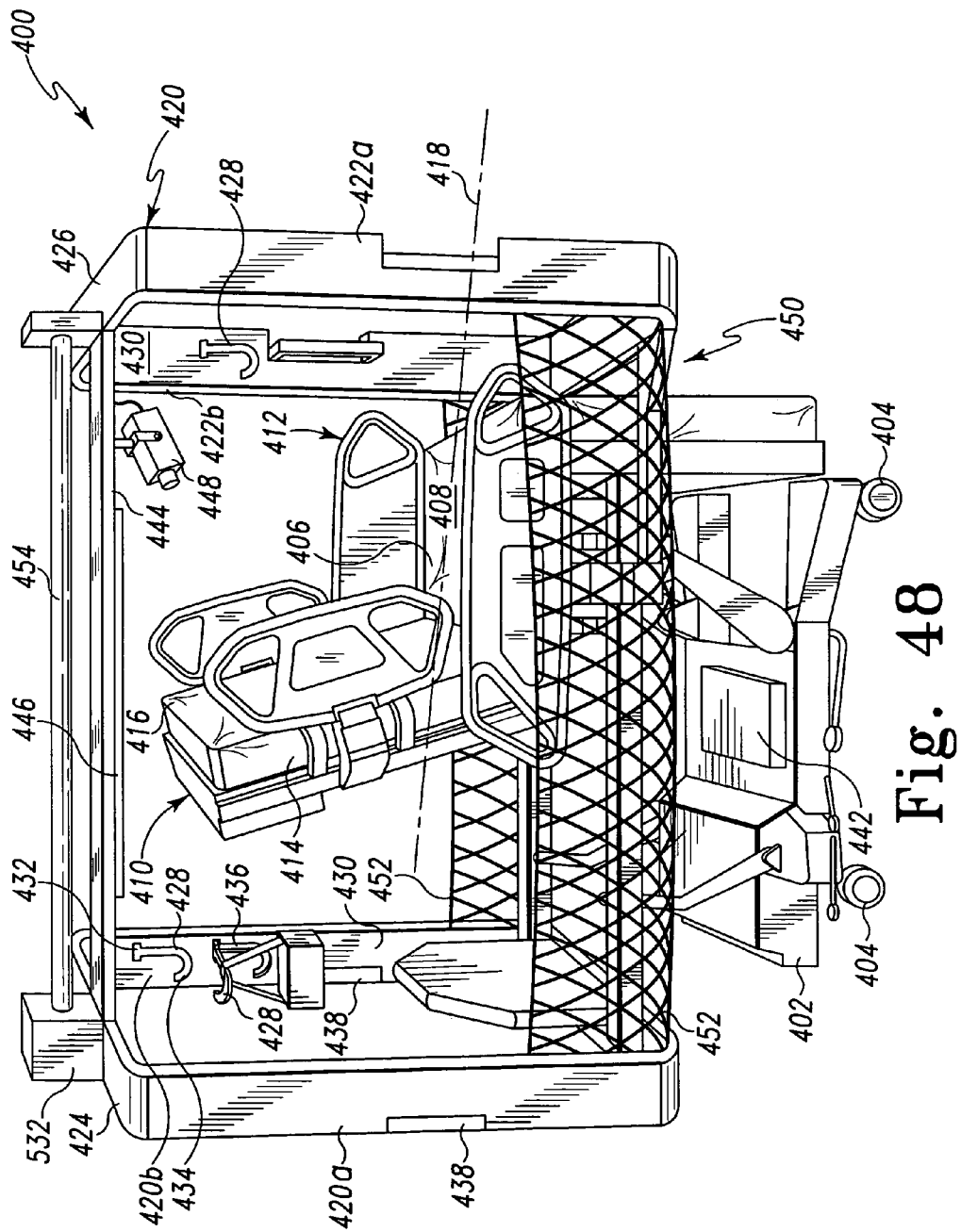
FIG. 48 is a perspective view of a bed configured to incorporate an embodiment of the proning apparatus of the present invention.

Referring now to FIG. 48, a further illustrative embodiment of the proning apparatus 400 of the present invention is illustrated as including a frame 402 supported by a plurality of casters 404. The frame 402 supports a patient platform or support 406 including an upwardly facing patient support surface 408. The patient support surface 408 includes a head end 410 and a foot end 412 and extends between first and second opposing side edges 414 and 416. A longitudinal axis 418 extends intermediate the first and second side edges 414 and 416.

An accessory frame 420 is supported by the bed frame 402 and includes a first pair of uprights 420a, 420b positioned proximate the head end 410 of the patient support surface 408 and a second pair of uprights 422a, 422b positioned proximate the head end 410 of the patient support surface 408. A first cross member 424 extends in a transverse direction and connects upper ends of the first uprights 420a and 420b. Likewise, a second cross member extends transversely relative to the patient support surface 408 and connects the upper ends of the second uprights 422a and 422b.

A plurality of accessory hooks 428 are pivotally supported by an inner surface 430 of each upright 420 and 422. As illustrated in FIG. 48, the hooks 428 may include first and second arms 432 and 434 defining a substantially "J" shape. When in a non-operative mode, the hooks 428 are received within a recess 436 formed within the inner surface 430 of the respective upright 420, 422. The hooks 428 are adapted to receive a plurality of accessories, including, but not limited to, intravenous (IV) bags, and monitoring equipment. It should be appreciated that the hooks 428 may be provided with a locking mechanism (not shown) to lock the hooks 428 in an operative position extending substantially perpendicular to the inner surface 430 of the respective upright 420, 422.

Referring further to FIG. 1, the first uprights 420*a* and 420*b* may each support a power assist handle 438 proximate a rear edge 440. The power assist handles 438 are operably connected to a drive motor 442 for propelling the apparatus 400. The power assist handles 438 may comprise those of the type disclosed in co-pending U.S. patent application Ser. No. 09/853,221, which is assigned to the assignee of the present invention and which is expressly incorporated herein by reference.

The first and second cross members 424 and 426 support a longitudinally extending accessory support 444. The accessory support 444 may be utilized to support a number of accessories including, but not limited to, an illumination source, such as a fluorescent light 446, and a camera, such as a video camera 448. The first and second uprights 420 and 422 together with the first and second cross members 424 and 426 may define a support structure for a bed enclosure 450. The enclosure 450 may include a pair of nets 452 guided for movement upwardly along the first and second uprights 420 and 422 and transversely along the first and second cross members 424 and 426 for containing the patient 23 within the apparatus 400. It may be further appreciated that the areas proximate the head end 410 and foot end 412 of the apparatus 400 may include netting supported by the first upright 420 and first cross member 424 and second uprights 422 and second cross member 426 in order to complete the enclosure 450.

A movable sleeve support member 454 is rotatably supported by the first and second uprights 420 and 422. More particularly, as illustrated in FIG. 48, the sleeve support member 454 is rotatably supported by the first and second cross members 424 and 426 and extends substantially longitudinally in parallel relation to the accessory support 444 and is substantially aligned above the horizontal axis 418 of the patient support surface 408. The sleeve support member 454 is configured to support a sleeve 456 to assist in the repositioning of a patient from a supine to a prone position. Additional details regarding the support of the sleeve 456 are provided below with reference to FIGS. 49-52.

Figure 49:
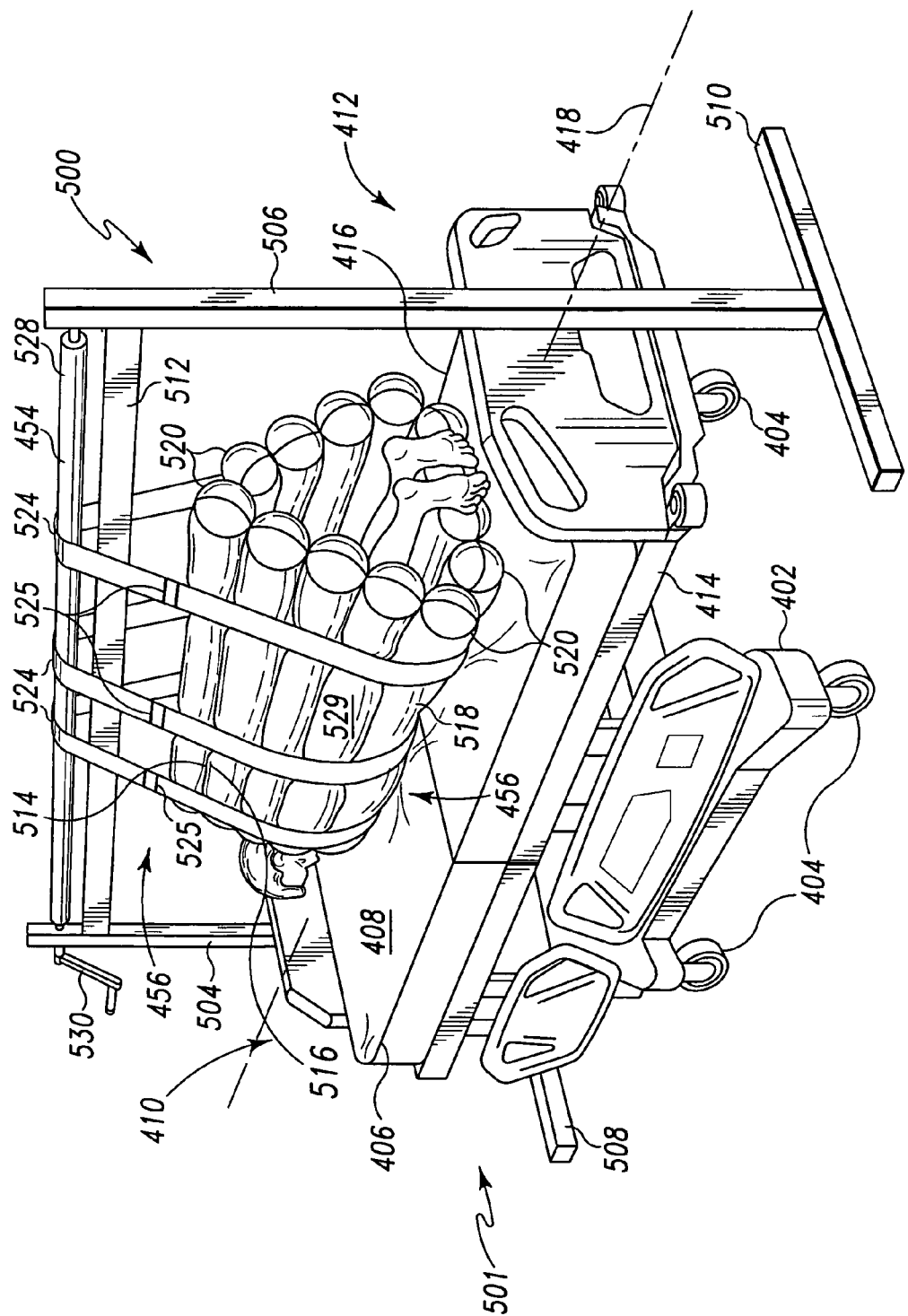
FIG. 49 is a perspective view of a proning apparatus according to a further embodiment of the present invention, including a rotatably mounted support member in substantial coaxial alignment with a longitudinal axis of a patient support surface.

With reference to FIG. 49, an illustrative embodiment proning apparatus 500 is illustrated as configured for independent support relative to a bed 501. As detailed above with respect to the embodiment of FIG. 48, a plurality of casters 404 support the bed frame 402. Likewise, a patient platform or support 406 is supported by the bed frame 402 and includes a patient support surface 408. As described above, the patient support surface includes a head end 410, foot end 412, and opposing first and second side edges 414 and 416. A longitudinal axis 418 extends intermediate the first and second side edges 414 and 416. The patient platform or support 406 is vertically moveable relative to the bed frame 402 through operation of a conventional drive mechanism, commonly referred to as a hi-lo mechanism.

In the embodiment of FIG. 49, the proning apparatus 500 includes an upright 504 positioned proximate the head end 410 and a second upright 506 positioned proximate the foot end 412. The first upright 504 is coupled to a first base member 508 and the second upright 506 is coupled to a second base member 510. It may be appreciated that both base members 508 and 510 may be supported on casters (not shown) to facilitate movement of the proning apparatus 500 relative to a conventional bed 501.

A strengthening member 512 extends intermediate the first and second uprights 504 and 506 and may be utilized in the manner described above with respect to the accessory support 444 for supporting accessories such as lights and cameras. The sleeve support member 454 is rotatably supported by the first and second uprights 504 and 506 in vertical spaced relation to the strengthening member 512. The sleeve support member 454 is substantially aligned in a transverse or horizontal direction with the longitudinal axis 418 of the patient support surface 408. The sleeve 456 includes first and second longitudinally extending side edges 514 and 516 defining an access opening therebetween and configured to receive the patient 23 in a set-up mode of operation, and to close the access opening in a turning mode of operation. The sleeve 456 of FIGS. 49-51 comprise a mattress 518 including a plurality of longitudinally extending fluid filled bladders 520. The bladders 520 combine to define an inner surface 522 for receiving and engaging a patient.

A plurality of straps 524 extend around an outer surface 526 of the mattress 518 and over the sleeve support member 454. Each strap 524 includes a fastener 525 for releasably securing opposing ends thereof. The straps 524 frictionally engage the sleeve support member 454 such that movement of the member 454 is transferred to the straps 524 and subsequently the mattress 518. An outer surface 528 of the sleeve support member 454 may be treated with a substance having a high coefficient of friction to facilitate frictional engagement with the straps 524. Further, the outer surface 529 of the mattress 518 may comprise a material with a lower coefficient of friction to facilitate movement relative to the patient support surface 408, while the inner surface 522 of the mattress 518 may comprise a material with a high coefficient of friction to prevent slipping between the patient 23 and the mattress 518.

A drive mechanism is coupled to the sleeve support member 454 in order to drive the member 454 in rotation. As illustrated in FIG. 49, the drive mechanism may comprise a hand crank 530 for manual operation by a caregiver. Alternatively, as illustrated in FIG. 48, the drive mechanism may comprise an electric motor 532.

Figure 51:
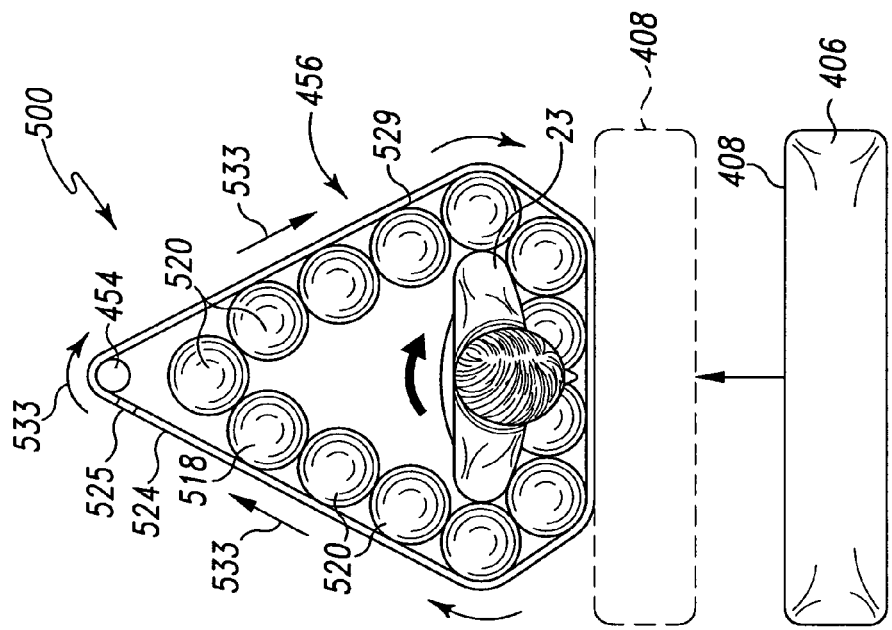
FIG. 51 is an end view, in partial schematic illustrating further operation of the proning apparatus of FIG. 49.
Figure 50:
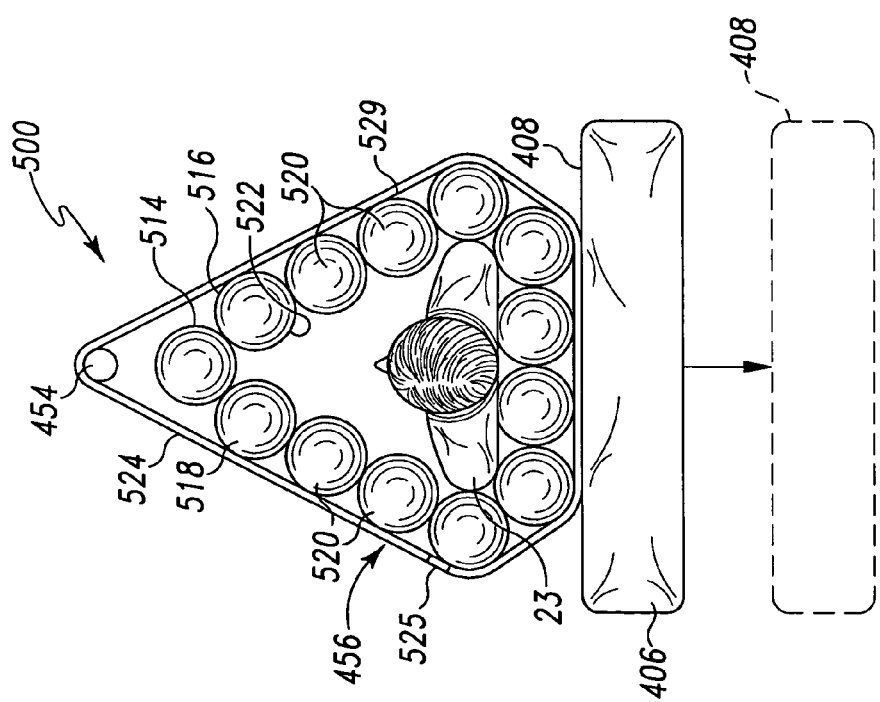
FIG. 50 is an end view, in partial schematic, illustrating operation of the proning apparatus of FIG. 49.

Referring now to FIGS. 50 and 51, operation of the proning apparatus 500 for turning a patient 23 from a supine to a prone position is illustrated. The process begins by placing the mattress 518 and the straps 524 intermediate the back of a patient 23 and the patient support surface 408. The first and second side edges 514 and 516 are then brought together to close the access opening, and opposing edges of the straps 524 are joined by fasteners 525 to form the sleeve about the patient 23. The straps 524 at this point are wrapped around the sleeve support member 454. Next, the patient support surface 408 is lowered to a position out of engagement with the outer surface 529 of the mattress 518. The hand crank 530 is then rotated that the sleeve support member 454 is rotated, thereby rotating the straps 524 and the mattress 518 as indicated by arrows 533 in FIG. 51. Movement of the sleeve 456 results in likewise rotational movement of the patient 23 from a supine to a prone position. At this point, the patient support surface 408 is raised into contact with the mattress 518 such that the weight of the patient 23 is transferred to the patient support 406. The straps 524 may then be disconnected and the mattress 518 removed from underneath the patient 23.

Figure 52:
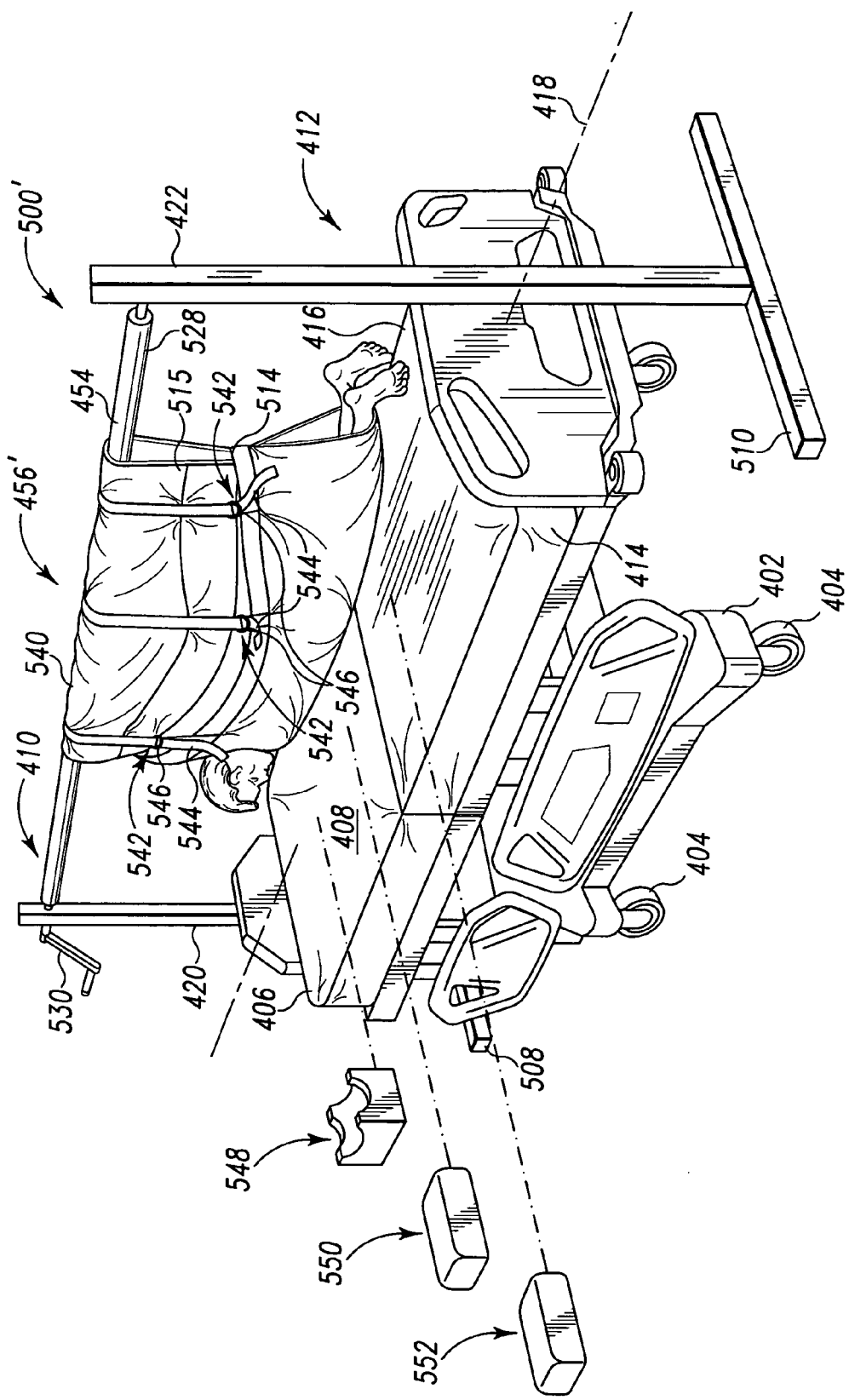
FIG. 52 is a perspective view of an alternative embodiment of the proning apparatus of FIG. 49.

A variation of the proning apparatus 500' is illustrated in FIG. 52 as including a sleeve 456' comprising a flexible sheet 540. The sheet 540 extends around an outer surface 528 of the sleeve support member 454 much in the same manner of the straps 524 of the mattress 518. The first and second side edges 514 and 516 of the sheet 540 overlap wherein the first side 514 of the sheet 540 is secured to a center portion 515 thereof through fasteners 542. In the embodiment of FIG. 52, the fasteners 542 include a strap 544 received within a conventional buckle 546.

Operation of the proning apparatus 500' of FIG. 52 is substantially similar to that of the mattress 518. It should be noted that conventional support cushions, such as a head cushion 548, a chest cushion 550 and a leg cushion 552 may be positioned intermediate the front of the patient 23 and the patient support surface 408 before the patient support surface 408 is raised into contact with the sleeve 456' following the turning of the patient 23.

Figure 53:
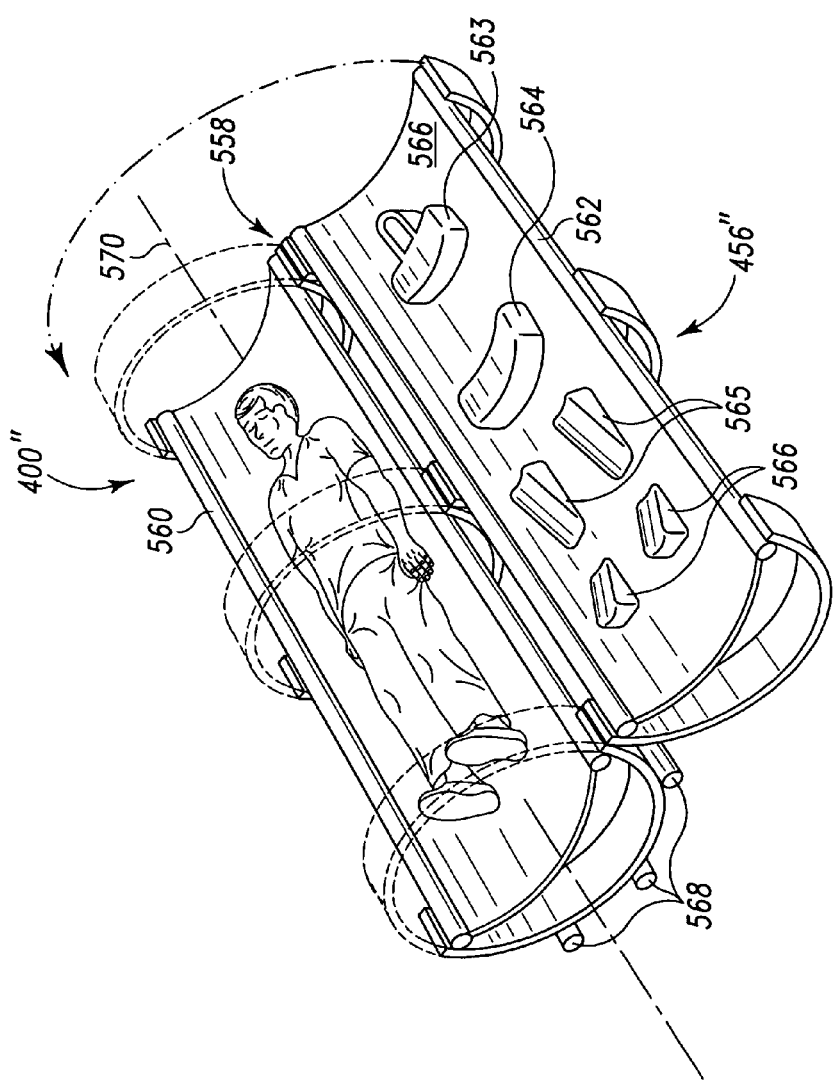
FIG. 53 is a perspective view of a proning apparatus according to another embodiment of the present invention.

FIG. 53 illustrates a further variation of the proning apparatus 400" wherein the sleeve 456" is formed as a substantially rigid shell 558 including a first portion 560 for supporting the patient 23 and a second portion 562 pivotally supported by the first portion 560. A plurality of cushions 563, 564, 565 and 566 are supported by an inside surface 567 of the second portion 562 of the shell 558 and are used to support the patient 23 in a prone position. These cushions 564 include a head cushion 563, a chest cushion 564, thigh cushions 565, and calf cushions 566. A plurality of rollers 568 provide a bearing surface to provide for rotation of the shell 558 about its longitudinal axis 570. The shell 558 may be driven in motion by a drive mechanism similar to the mover disclosed in copending U.S. patent application Ser. No. 09/810,376, which is assigned to the assignee of the present invention, and which is expressly incorporated herein by reference.

Figure 54:
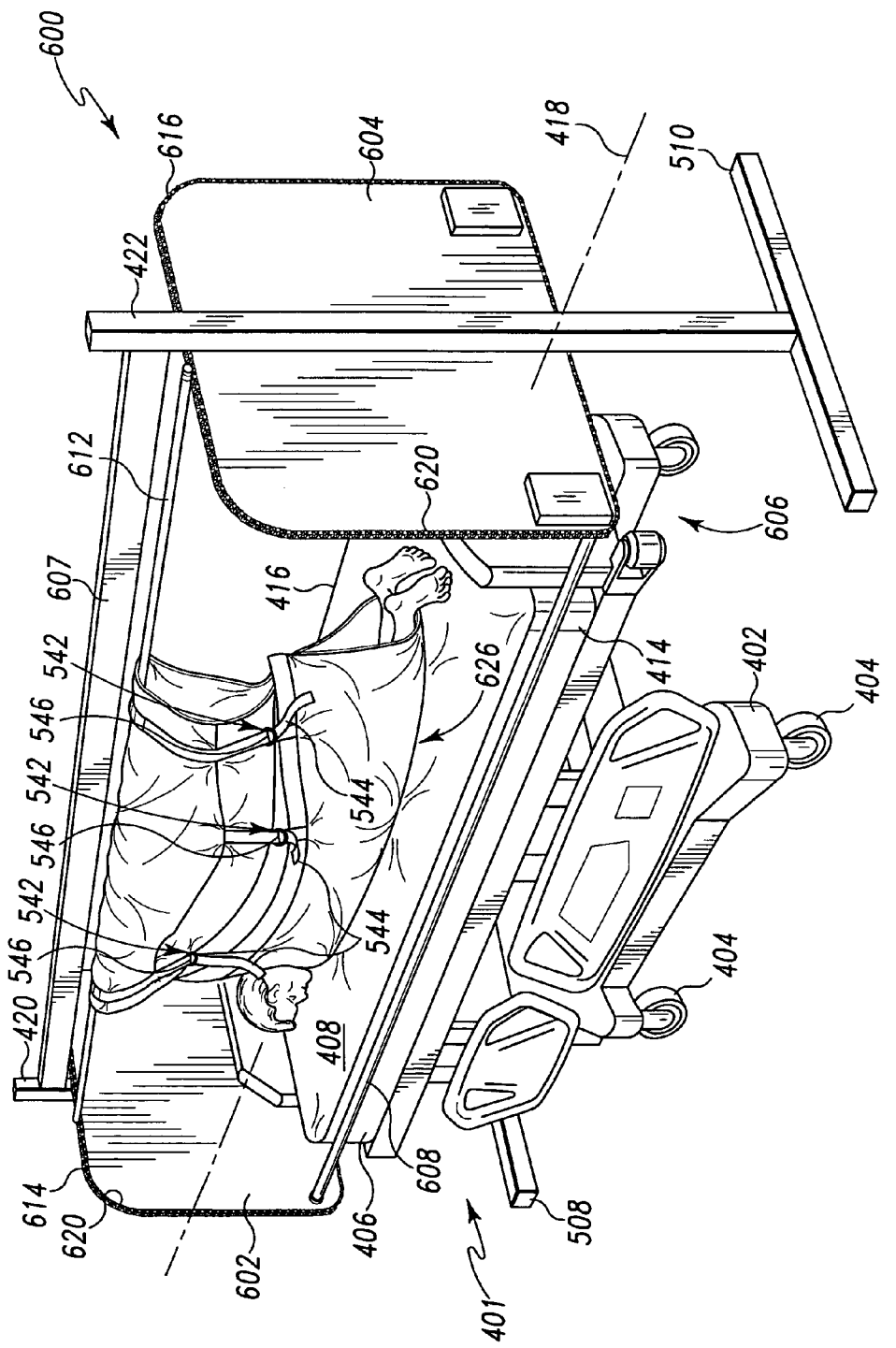
FIG. 54 is a perspective view of a proning apparatus according to a further embodiment of the present invention, the proning apparatus including a transversely moving support member.

Turning now to FIGS. 54-57, a further illustrative embodiment of a proning apparatus 600 is illustrated. Again, the proning apparatus 600 may be formed integral with a conventional bed 401 or may be movably supported adjacent thereto as illustrated in FIG. 54. The bed 401 is substantially similar to that described above and includes a frame 402 for supporting a patient platform or support 406. The patient support 406 includes a patient support surface 408. First and second uprights 420 and 422 support first and second drive support members 602 and 604, respectively. The first and second uprights 420 and 422 are supported by first and second base members 508 and 510. The base members 508 and 510 may be supported by casters (not shown) thereby facilitating movement of the proning apparatus 600 relative to the bed frame 402. A drive mechanism 606 is supported by the first and second drive support members 602 and 604. A strengthening member 607 may serve as an accessory support and extends between upper ends of the first and second uprights 420 and 422. Likewise, first and second braces 608 and 610 extend between the first and second drive support members 602 and 604 immediately adjacent to the opposing side edges 414 and 416 of the patient support surface 408.

A sleeve support member 612 is coupled to the drive mechanism for lateral movement above the patient support surface 408. The drive mechanism of FIGS. 54-57 includes first and second chains 614 and 616 coupled to the first and second drive support members 602 and 604, respectively. Moreover, each chain preferably travels along a path determined by a guide member, such as conventional tracks 620 supported by the first and second drive support members 602 and 604. Opposing ends 622 and 624 of the sleeve support member 612 are fixed to corresponding links in the first and second chain 614 and 616. The drive mechanism 606 further includes a driver, such as the manual crank 530 illustrated in FIG. 55-57. As may be readily appreciated, the manual crank 530 may be replaced by a conventional electric motor. The crank 530 is operably connected to the first and second chains 614 and 616 through a conventional mechanical linkage, such as a pair of sprockets 622 supported on opposing ends of a longitudinally extending drive shaft (not shown) extending beneath the patient support surface 408. As can be readily appreciated, operation of the hand crank 530 results in corresponding movement of the first and second chains 614 and 616 through the track 620 about the periphery of the first and second drive support members 602 and 604. A sleeve 626 is supported for movement with the sleeve support member 612. The sleeve 626 is substantially similar to the sleeve 456 described above with respect to FIG. 52.

Referring to FIGS. 55-57, the operation of the proning apparatus 600 is described in greater detail. Initially, as illustrated in FIG. 55, the patient 23 is wrapped in the sleeve 626 with the sleeve support member 612 positioned essentially horizontally level with the patient 23 adjacent the first side edge 414 of the patient support surface 408. As illustrated in FIG. 55, at this point the patient 23 is in a supine position. The drive mechanism 530 is then activated for driving the first and second chains 614 and 616 in a substantially counterclockwise direction around the first and second drive support member 602 and 604 as illustrated by arrows 628. Motion of the hand crank 530 is illustrated by arrow 630. The sleeve support member 612 is driven vertically upwardly and then transversely relative to the patient support surface 408. As this point, the patient 23 essentially rolls about a pivot point 632 defined by the sleeve 626. Continuous motion of the chains 614 and 616 in the counterclockwise direction cause the sleeve support member 612 to continue its motion to a horizontal or transverse position near the second side edge 416 of the patient support surface 408. The sleeve support member 612 then travels downwardly to a position adjacent the second side edge 416 of the patient support surface 408, thereby completing the turn of the patient 23 about his longitudinal axis. As illustrated in FIG. 57, the patient 23 is now in a prone position.

Figure 59:
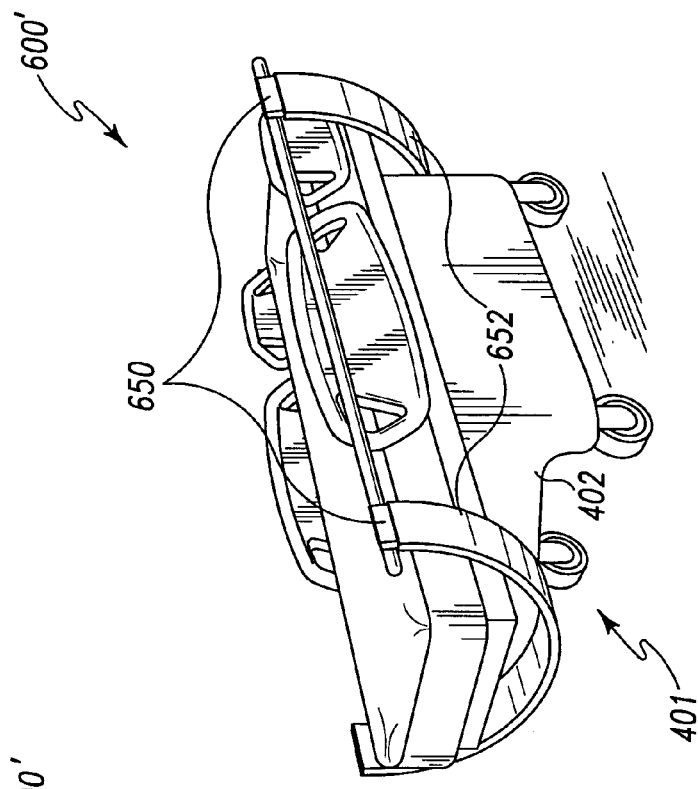
FIG. 59 is a perspective view similar to FIG. 58, illustrating the support member in a stored position.
Figure 58:
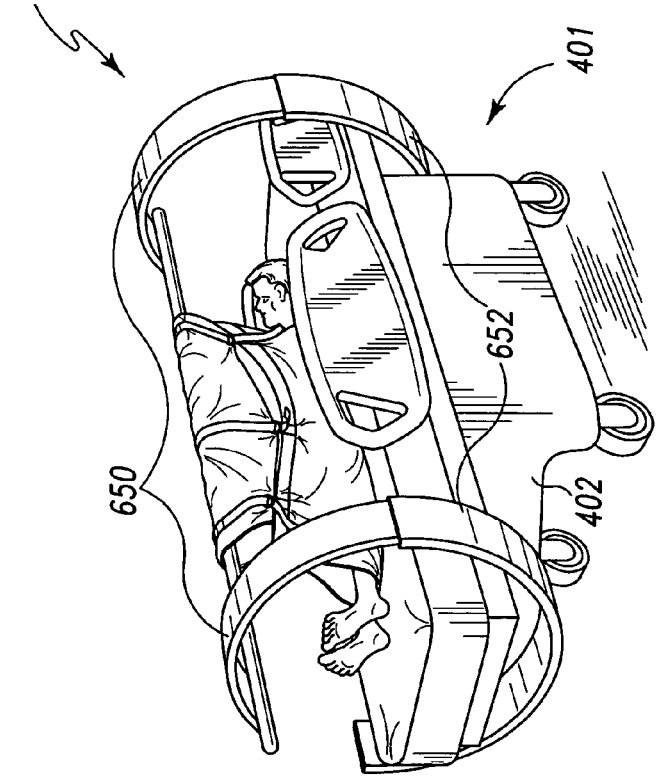
FIG. 58 is a perspective view of an alternative embodiment of the proning apparatus of FIG. 54, illustrating the support member in an operative position.

FIGS. 58 and 59 illustrate an alternative embodiment proning apparatus 600' which functionally turns a patient 23 from a supine position to a prone position in a manner substantially similar to the proning apparatus 600 described above with respect to FIGS. 54-57. The chains 614 and 616 of the proning apparatus 600 have been replaced in the proning apparatus 600' with arms 650 telescopingly received within arcuate housings 652 defining the first and second drive support members. The housings 652 are fixed to the frame 402 of the bed 401. A conventional drive mechanism may be utilized to move the arms 650 relative to the housings 652. Moreover, the drive mechanism may be similar to the mover disclosed in co-pending U.S. patent application Ser. No. 09/810,376, which is assigned to the assignee of the present invention and which is expressly incorporated herein by reference. It should be appreciated that other similar drive mechanisms may be readily substituted therefore.

Figure 60:
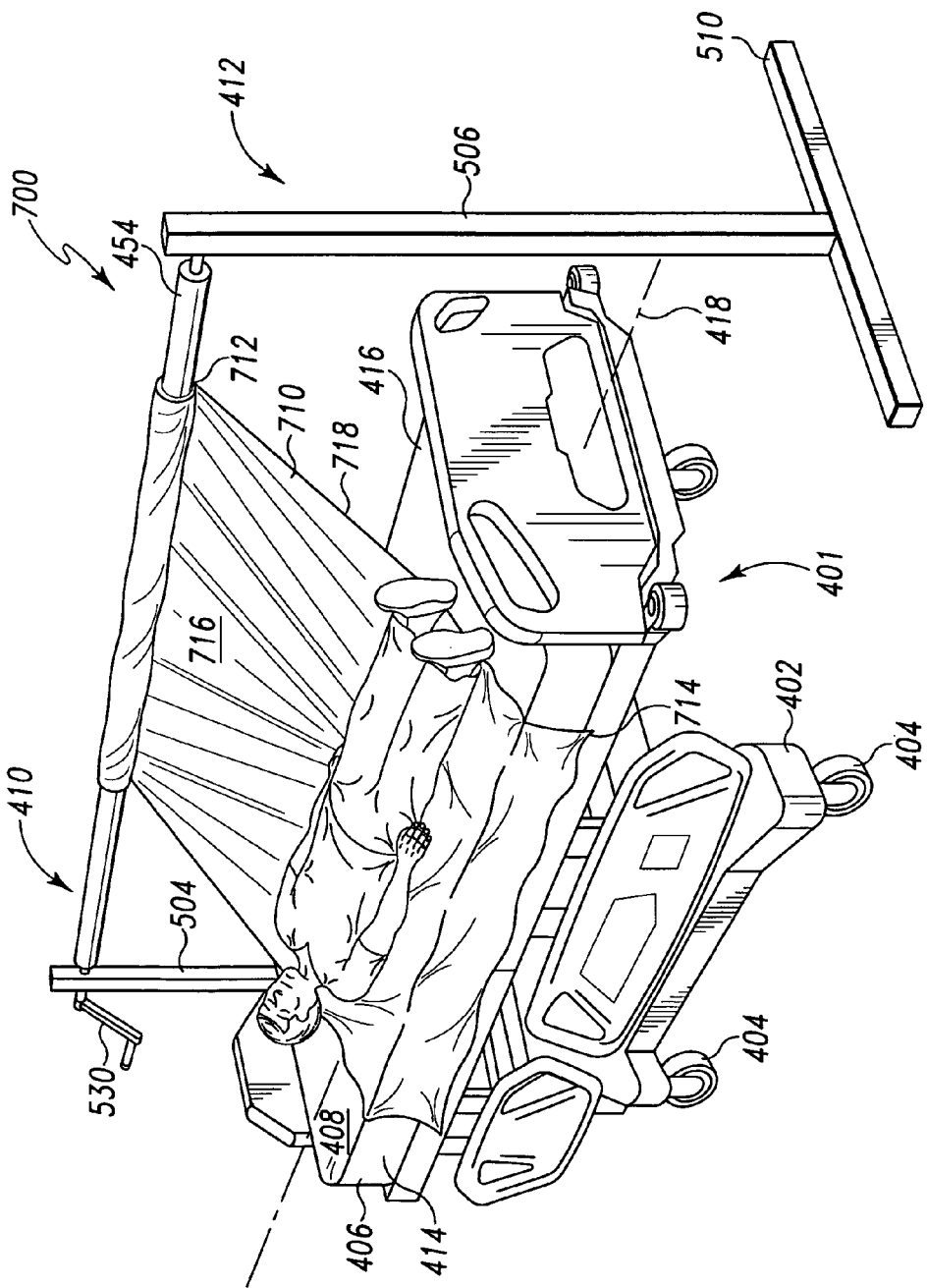
FIG. 60 is a perspective view of a proning apparatus according to a further embodiment of the present invention, including a rotational support member positioned substantially off-center from a longitudinal axis of a patient support surface.
Figure 66:
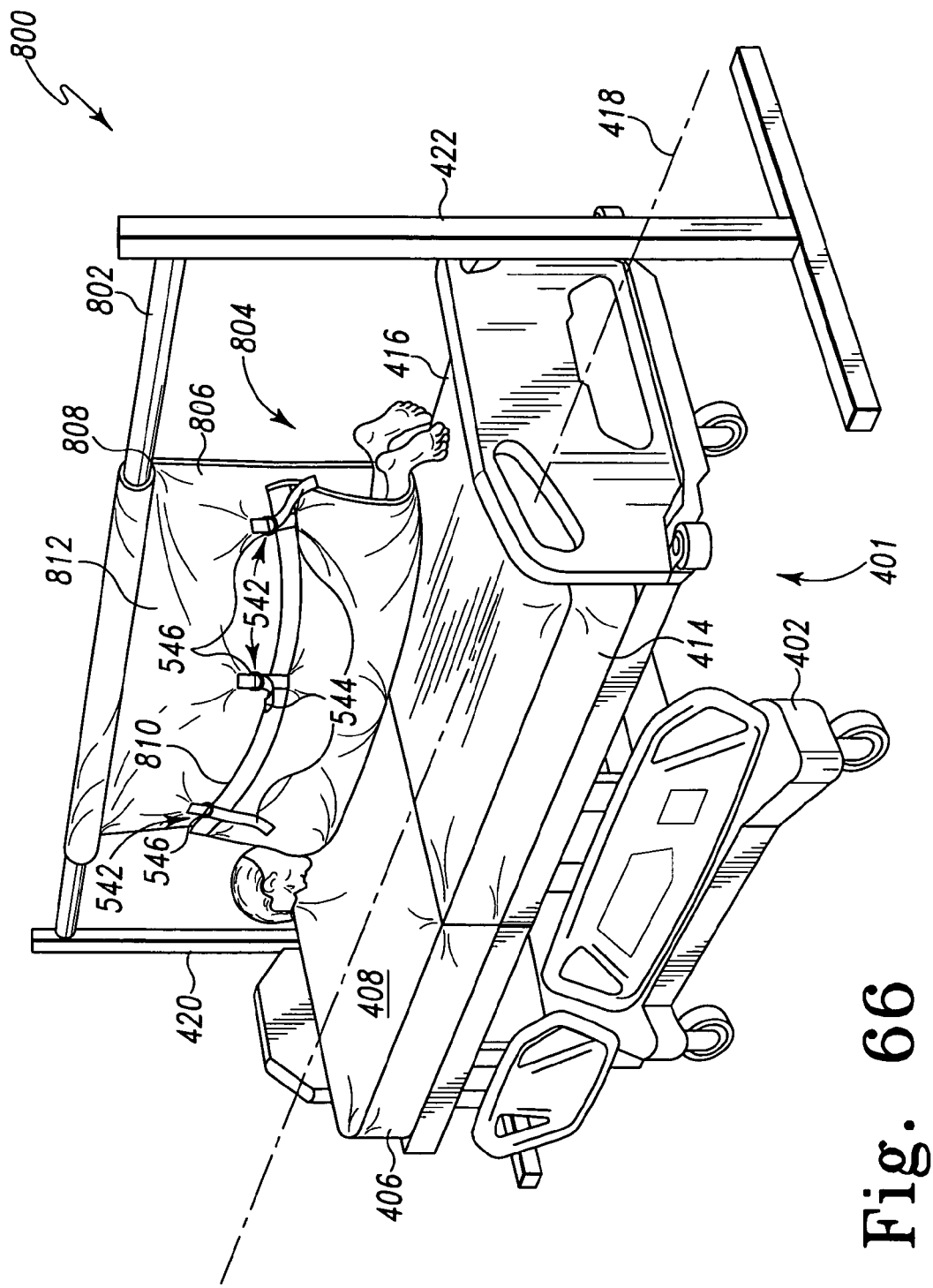
FIG. 66 is a perspective view of a proning apparatus according to a further embodiment of the present invention, including a wrap supported substantially off-center from a longitudinal axis of a patient support surface.
Figure 70:
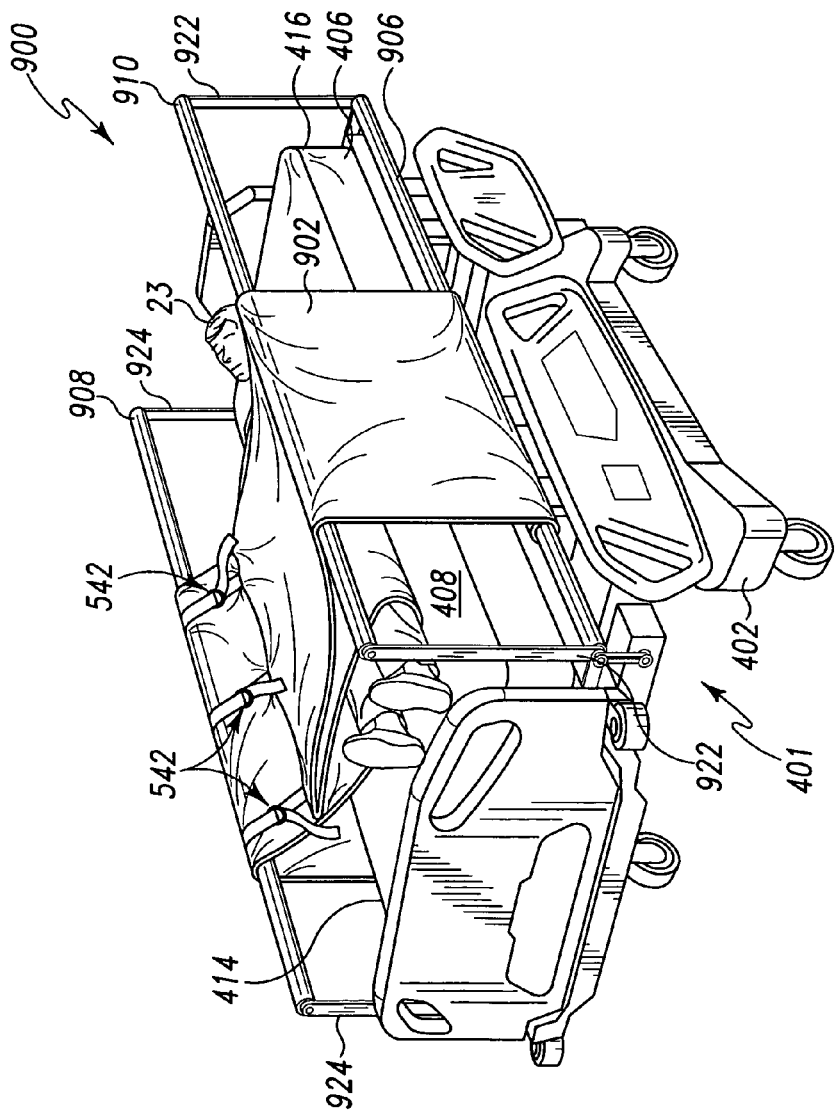
FIG. 70 is a perspective view of a proning apparatus according to a further embodiment of the present invention, including a sleeve supported for transverse movement relative to a patient support surface.

FIGS. 60-63 illustrate another illustrative embodiment of the proning apparatus 700 of the present invention. The proning apparatus 700 includes a bed 401 substantially the same as that described above with respect to the earlier embodiments. The proning apparatus 700 includes first and second uprights 420 and 422 positioned adjacent the head end 410 and the foot end 412 of the patient support surface 408, respectively. The support member 454 is rotatably supported proximate the upper ends of the first and second uprights 420 and 422 and laterally offset from the longitudinal axis 418. A drive mechanism, which may comprise a hand crank 530, as illustrated in FIG. 60, is provided adjacent one end of the support member 454 for providing rotational movement thereto. A sheet 710 including opposing first and second ends 712 and 714 is supported by the support member 454. Moreover, the first end 712 of the sheet 710 is fixed to the support member 454 while a second end 714 is positioned proximate the first side edge 416 of the patient support surface 408.

An upper surface 716 of the sheet 710 may be provided with a material having a higher coefficient of friction than the lower surface 718 in order to facilitate adhesion of the patient 23 to the sheet 710 while enhancing sliding between the sheet 710 and the patient support surface 408.

Referring now to FIGS. 61-63, operation of the proning apparatus 700 is described in greater detail. Initially, the proning apparatus 700 is positioned adjacent the bed 401 such that the sheet support 454 is positioned above the patient support surface 408 and is horizontally or laterally offset from the longitudinal axis 418. More particularly, the sheet support 454 is preferably positioned immediately above the second side edge 416 of the patient support surface 408. The second end 712 of the sheet 710 is then passed under the back of the patient 23 supported on the patient support surface 408. The drive mechanism is activated, typically by rotating the hand crank 530 in the direction of arrow 719. Such movement causes the sheet 710 to wrap upon the support member 454, resulting in the sheet moving transversely across the patient support surface 408 and upwardly toward the support member 454. As such, the patient 23 is caused to turn and rotate about a pivot point 720 defined by the sheet 710. As illustrated in FIG. 63, the patient 23 is then located in a prone position on the patient support surface 400. The sheet 710 may then be removed from underneath the front of the patient 23.

FIGS. 64 and 65 illustrate an alternative embodiment of the proning apparatus 700'. In the proning apparatus 700', the support member or sheet roll 454 may be fixed from rotation between the first and second uprights. The first and second uprights 420' and 422' include a first portion or housing 730 telescopingly receiving a second portion or arm 732. As such, a pulling device is defined by the arm 732 wherein vertical movement of the arm 732 results in the sheet 710 being pulled transversely across the patient support surface 408 and upwardly. As such, the patient 23 is caused to turn from a supine to a prone position in the manner described above with respect to FIGS. 61-63. The first and second uprights 420' and 422' may be supported on casters 404 to facilitate movement of the proning apparatus 700' relative to the bed 401.

Turning now to FIGS. 66-69, a further embodiment of the proning apparatus 800 of the present invention is illustrated for use with a bed 401 including a patient support surface 408 supported by a bed frame 402. The patient support 408 may be driven in vertical motion by a conventional drive mechanism.

First and second uprights 420 and 422 are connected to first and second base members 508 and 510 and extend generally vertically thereto. A support member 802 is fixed intermediate the first and second uprights 420 and 422 proximate the upper ends thereof. As such, the support member 802 is positioned vertically above the patient support surface 408 and is positioned horizontally off-center from the longitudinal axis 418 of the patient support surface 408. In a preferred embodiment, the support member 802 is positioned horizontally proximate one of the first and second sides 414 and 416 of the patient support surface 408. A sleeve 804 defined by a sheet 806 including first and second ends 808 and 810 and a center portion 812 intermediate the first and second ends 808 and 810. More particularly, the sleeve 804 is defined by a plurality of fasteners 542 securing the second end 810 of the sheet 806 to the center portion 812 thereof. The first end 808 of the sheet 806 is fixed to the support member 802.

In operation, as illustrated in FIGS. 67-69, a patient 23 is placed in a supine position with the sheet 806 positioned intermediate the back of the patient 23 and the patient support surface 408. The second end 810 of the sheet 806 then is wrapped around the front of the patient 23 and secured to a center portion 812 thereof through the fasteners 542. The fasteners 542 preferably include a strap 544 secured to the second end 810 of the sheet 806 and a buckle 546 secured to the center portion 812 thereof.

Next, as illustrated in FIG. 68, the patient support surface 408 is lowered in the direction of arrow 814. The patient support surface 408 is lowered until the sheet 806 no longer contacts the patient support surface 408. As such, the sleeve 804 and patient 23 are caused to rotate in the direction of arrow 816. Next, the patient support surface 408 is raised in the direction of arrow 818. Contact between the sleeve 804 and the patient support surface 408 again occurs proximate the shoulder of the patient 23 thereby defining a pivot point therebetween. The caregiver may then assist in causing pivoting movement of the patient 23 about the pivot axis by applying a force in the direction of arrow 820. The patient 23 is then placed in a prone position within the sleeve 804 as illustrated in FIG. 69. At that point, the fasteners 542 may be released and the sheet removed from underneath the chest of the patient 23.

Referring now to FIGS. 70-73, another exemplary embodiment of a proning apparatus 900 of the present invention is illustrated as including a sheet 902 extending between sides 414 and 416 of a patient support surface 408. Moreover, the sheet 902 is guided in motion by a pair of drive rollers 904 and 906 and a pair of idler rollers 908 and 910. The first drive roller 904 is supported adjacent the first side edge 414 of the patient support surface 408 while the second drive roller 906 is supported adjacent the second side edge 416 of the patient support surface 408. The first and second idler rollers 908 and 910 are positioned above the patient support surface 408 horizontally adjacent to the first and second drive rollers 904 and 906. The sheet 902 includes a first sleeve portion 912 configured to be placed adjacent the chest of the patient 23, a second sleeve portion 914 configured to be placed adjacent the back of the patient 23 and a connecting portion 916 extending between the first sleeve portion 912 and the first drive roller 904. The first and second sleeve portions 912 and 914 are releasably secured together by a plurality of fasteners 542 thereby defining a sleeve 920 for receiving the patient 23.

The first idler roller 908 is rotatably supported by a pair of uprights 922 and the second idler roller 910 is rotatably supported by a second pair of uprights 924. Both the first and second pair of uprights 922 and 924 are coupled to the bed frame 402 and extend upwardly from the first and second drive rollers 904 and 906.

The operation of the proning apparatus 900 is illustrated in FIGS. 71-73. In FIG. 71, the sheet 902 is placed intermediate the back of the patient 23 and the patient support surface 408. The first sleeve portion 912 is then secured to the second sleeve portion 914 by way of the fasteners 542. Next, the drive mechanism is operated to cause the sheet to move in the direction indicated by arrows 925. The first drive roller 904 pulls on the connecting portion 916 of the sheet 902 which, in turn, pulls the sleeve 920 upwardly and to the right in FIG. 24 and causing a rotation of the sleeve 920 and the patient 23 about a pivot point 926 in the direction of arrow 928. Continued movement of the sheet 902 causes the patient 23 to continue to rotate into a prone position as illustrated by FIG. 73.

As detailed above, proning has shown to be an effective intervention to increase oxygenation in the ARDS patient. Ease in attaining the prone position facilitates its utilization. The present invention reduces manpower required, increases caregiver efficiency, and improves line management. The present invention further provides a system solution through frame articulation.

Additionally, as described above chest binding may prove to be an effective method of alveolar recruitment. The present invention provides for ventilation of distant lung areas, portability, dynamic patient positioning, and alternative percussion and vibration.

Although the invention has been described in detail with reference to preferred embodiments, variations and modifications exist within the scope and spirit of the invention as described and defined in the following claims.

The invention claimed is:

1. A pulmonary therapy system for use with a ventilator for supplying air to the lungs of a patient, said system comprising:
   a chest binding apparel apparatus including a plurality of air bladders, said chest binding apparel apparatus configured to be supported proximate the chest of a patient;
   an air supply in fluid communication with said plurality of air bladders;
   a controller operably connected to said air supply;
   a ventilator pressure sensor adapted to be coupled to a ventilator for sensing a pressure of air supplied to the patient and generating a ventilator pressure signal indicative thereof, said ventilator pressure sensor in communication with said controller for supplying said ventilator pressure signal thereto;
   an apparel pressure sensor coupled to said binding apparel apparatus for sensing a pressure applied by said binding apparel apparatus to the chest of the patient and generating an apparel pressure signal indicative thereof, said apparel pressure sensor in communication with said controller for supplying said apparel pressure signal thereto; and
   wherein said controller controls air flow to said plurality of air bladders in response to said ventilator pressure signal.

2. The pulmonary therapy system of claim 1, wherein said apparel pressure sensor comprises a pressure sensing fabric.

3. The pulmonary therapy system of claim 1, further comprising a display in communication with said controller.

4. The pulmonary therapy system of claim 1, further comprising a switching valve coupled to said air supply for alternating between a first mode of operation wherein air is supplied to said air bladders and a second mode of operation wherein air is evacuated from said air bladders.

5. The pulmonary therapy system of claim 4, further comprising an exhaust line coupled to said switching valve for exhausting evacuated air from said air bladders to atmosphere, and a bladder supply line for supplying air from said air supply to said air bladders, said switching valve alternatively connecting said air supply to said exhaust line and said bladder supply line.

6. The pulmonary therapy system of claim 1, wherein said chest binding apparel comprises a vest including a front portion, a rear portion, and a head receiving aperture intermediate said front portion and said rear portion, said plurality of air bladders including at least one front bladder supported by said front portion and at least one rear bladder supported by said rear portion.

7. The pulmonary therapy system of claim 6, wherein each of said at least one front and rear bladders include a plurality of independently inflatable zones.

8. A pulmonary therapy system for use with a ventilator for supplying air to the lungs of a patient, said system comprising:
   a chest binding apparel apparatus including a plurality of air bladders, said chest binding apparel apparatus configured to be supported proximate the chest of a patient;
   an air supply in fluid communication with said plurality of air bladders;
   a ventilator pressure sensor adapted to be coupled to a ventilator for sensing a pressure of air supplied to the patient from the ventilator and generating a ventilator pressure signal indicative thereof, said ventilator pressure sensor in communication with a controller for supplying said ventilator pressure signal thereto, said controller being configured to control air flow to said plurality of air bladders in response to said ventilator pressure signal;
   a switching valve coupled to said air supply;
   wherein the controller is operably coupled to said switching valve, said controller is configured to move said switching valve between a first mode of operation wherein air is supplied to said air bladders and a second mode of operation wherein air is evacuated from said air bladders.

9. The pulmonary therapy system of claim 8, further comprising an apparel pressure sensor coupled to said binding apparel apparatus for sensing a pressure applied by said binding apparel apparatus to the chest of the patient and generating an apparel pressure signal indicative thereof, said apparel pressure sensor in communication with said controller for supplying said apparel pressure signal thereto.

10. The pulmonary therapy system of claim 9, wherein said apparel pressure sensor comprises a pressure sensing fabric.

11. The pulmonary therapy system of claim 8, further comprising a display in communication with said controller.

12. The pulmonary therapy system of claim 8, further comprising an exhaust line coupled to said switching valve for exhausting evacuated air from said air bladders to atmosphere, and a bladder supply line for supplying air from said air supply to said air bladders, said switching valve alternatively connecting said air supply to said exhaust line and said bladder supply line.

13. The pulmonary therapy system of claim 8, wherein said chest binding apparel comprises a vest including a front portion, a rear portion, and a head receiving aperture intermediate said front portion and said rear portion, said plurality of air bladders including at least one front bladder supported by said front portion and at least one rear bladder supported by said rear portion.

14. The pulmonary therapy system of claim 13, wherein each of said at least one front and rear bladders include a plurality of independently inflatable zones.

15. The pulmonary therapy system of claim 8, wherein the controller is configured to activate the first mode of operation when the ventilator pressure signal indicates that air is being supplied to the patient.

* * * * *